(12) United States Patent
Napier et al.

(10) Patent No.: US 10,017,796 B2
(45) Date of Patent: Jul. 10, 2018

(54) TRANSGENIC MICROALGAE WITH INCREASED PRODUCTION OF AT LEAST ONE OMEGA-3 LONG CHAIN POLYUNSATURATED FATTY ACID

(71) Applicant: ROTHAMSTED RESEARCH LIMITED, Harpenden (GB)

(72) Inventors: Jonathan A. Napier, Harpenden (GB); Olga Sayanova, Harpenden (GB); Mary Hamilton, Harpenden (GB); Royah Vaezi, Harpenden (GB)

(73) Assignee: ROTHAMSTED RESEARCH LIMITED (GB)

( * ) Notice: Subject to any disclaimer, the term of this patent is extended or adjusted under 35 U.S.C. 154(b) by 170 days.

(21) Appl. No.: 14/432,579

(22) PCT Filed: Oct. 1, 2013

(86) PCT No.: PCT/GB2013/052553
§ 371 (c)(1),
(2) Date: Mar. 31, 2015

(87) PCT Pub. No.: WO2014/053821
PCT Pub. Date: Apr. 10, 2014

(65) Prior Publication Data
US 2015/0275243 A1    Oct. 1, 2015

(30) Foreign Application Priority Data

Oct. 1, 2012 (GB) .................................. 1217524.6

(51) Int. Cl.
| | |
|---|---|
| *C12N 1/00* | (2006.01) |
| *C12P 7/64* | (2006.01) |
| *A61K 36/02* | (2006.01) |
| *C12N 9/02* | (2006.01) |
| *C12N 9/10* | (2006.01) |
| *C12N 1/12* | (2006.01) |
| *C12N 15/79* | (2006.01) |
| *C12N 15/82* | (2006.01) |
| *C11B 1/00* | (2006.01) |
| *C12N 9/00* | (2006.01) |
| *A23L 33/12* | (2016.01) |

(52) U.S. Cl.
CPC ............. *C12P 7/6427* (2013.01); *A23L 33/12* (2016.08); *A61K 36/02* (2013.01); *C11B 1/00* (2013.01); *C12N 1/12* (2013.01); *C12N 9/0071* (2013.01); *C12N 9/1025* (2013.01); *C12N 9/93* (2013.01); *C12N 15/79* (2013.01); *C12N 15/8247* (2013.01); *C12P 7/6472* (2013.01); *C12Y 114/19003* (2013.01); *C12Y 602/01003* (2013.01)

(58) Field of Classification Search
None
See application file for complete search history.

(56) References Cited

U.S. PATENT DOCUMENTS 7,842,852 B2 * 11/2010 Cirpus ................. C12N 9/0006
530/350
2008/0076166 A1    3/2008 Cirpus et al.

FOREIGN PATENT DOCUMENTS

WO    2005012316    2/2005

OTHER PUBLICATIONS

Domergue et al, Eur. J. Biochem. 269: 4105-4113, 2002.*
Harwood et al., "The versatility of algae and their lipid metabolism," Biochimie, 91: 679-684 (2009).
Huang et al., "Enzymes for transgenic biosynthesis of long-chain polyunsaturated fatty acids," Biochimie, 86: 793-798 (2004).
Meyer et al., "Novel fatty acid elongases and their use for the reconstitution of docosahexaenoic acid biosynthesis," Journal of Lipid Research, 45: 1899-1909 (2004).
Rubio-Rodriguez et al., "Production of omega-3 polyunsaturated fatty acid concentrates: A review," Innovative Food Science and Emerging Technologies, 11:1-12 (2010).
Ward et al., "Omega-3/6 fatty acids: Alternative sources of production," Process Biochemistry, 40: 3627-3652 (2005).
Zhou et al., "Isolation and characterization of genes from the marine microalga *Pavlova salina* encoding three front-end desaturases involved in docosahexaenoic acid biosynthesis," Phytochemistry, 68: 785-796 (2007).
Radakovits et al., Genetic engineering of fatty acid chain length in *Phaeodactylum tricornutum*, Metabolic Engineering, 13:89-95, 2011.

* cited by examiner

*Primary Examiner* — Elizabeth McElwain
(74) *Attorney, Agent, or Firm* — Tarolli, Sundheim, Covell & Tummino LLP

(57) ABSTRACT

The invention relates to genetically modified organisms with enhanced production of omega-3 long chain polyunsaturated fatty acids.

12 Claims, 15 Drawing Sheets

Dark grown plates +/- glucose 10 days after single colonies were streaked on to plates
WT cells cannot grow in the dark (top of plates)

TRANSGENIC MICROALGAE WITH INCREASED PRODUCTION OF AT LEAST ONE OMEGA-3 LONG CHAIN POLYUNSATURATED FATTY ACID

CROSS-REFERENCE TO RELATED APPLICATIONS

This application is a U.S. national phase application filed under 35 U.S.C. § 3.71 of International Application No. PCT/GB2013/052553, filed Oct. 1, 2013, which claims the benefit of the priority date of United Kingdom Application No. 1217524.6, filed Oct. 1, 2012. The content of these earlier-filed applications is hereby incorporated by reference in the present application in its entirety.

SEQUENCE LISTING

A Sequence Listing is incorporated in this patent document as a .txt file entitled "SequenceListing5D108002US1." The .txt file was created on Mar. 31, 2015and is 72.7 KB in size).

FIELD OF THE INVENTION

The invention relates to transgenic organisms, in particular trancgenic microalgae,with enhanced production of omega-3 long chain polyunsaturated fatty acids,related methods and uses.

INTRODUCTION

Long chain polyunsaturated fatty acids (LC-PUFAs) have a carbon backbone of at least 20 carbons in length and contain multiple double-bond desaturations. Long chain polyunsaturated fatty acids can be grouped into either an omega-3 (ϖ-3) or omega-6 (ϖ-6) category based on the position of the first double bond from the methyl, or ϖ, fatty acid terminus.

It is now well established that omega-3 LC-PUFAs, especially eicosapentaenoic acid (EPA; 20:5Δ5,8,11,14,17) and docosahexaenoic acid (DHA; 22:6Δ4,7,10,13,16,19) are essential constituents of human nutrition and have key roles in growth and development of infants and children and in maintaining health through their effects on immune system (Voigt et al., 2000; Calder, 2003). There is growing evidence from clinical studies that the presence of omega-3 LC-PUFAs in the human diet has therapeutic effect in conditions such as cardiovascular diseases, obesity, metabolic syndrome and eczema (Navarro et al., 2000; Nugent, 2004; Das, 2002).

Although marine fish is the main dietary source of EPA and DHA, the depletion of fish stocks and pollution of the marine environment indicate an urgent need for an alternative and sustainable source of LC-PUFAs. Marine microorganisms are the primary producers of LC-PUFAs in the aquatic food chain and EPA- and DHA-rich microalgae have been demonstrated to be a promising alternative source to fish oils for human consumption. Thus, commercial cultivation of *Crypthecodinium cohnii* and *Schizochytrium* sp. have been successfully developed for DHA production and some marine microorganisms have demonstrated potential for the industrial production of EPA (*Nannochloropsis* species, *Phaeodactylum* species, *Nitzshia* spp.) (Harwood and Guschina, 2009). However, commercial production of highly valuable products like omega-3 LC-PUFAs is expensive to maintain and represents a substantial technological challenge.

One of the approaches to increase the levels of LC-PUFAS is to use acyl-CoA dependent desaturases (Venegas-Caleron et al., 2010). In recent years, considerable focus has been placed on engineering higher plants for the production of very long chain polyunsaturated fatty acids (VLC-PUFAs) in their seed oils. Recently, the advantages of using an acyl-CoA-dependent Δ6-desaturase from *Ostreococcus tauri* (OtD6) to synthesize LC-PUFAs in transgenic *Arabidopsis* and Camelina plants have been demonstrated (Sayanova O., et al, 2012, Ruiz-Lopez N., et al., 2012). These studies indicate that the first step in the LC-PUFA pathway, the Δ6-desaturation, is rate-limiting.

As an alternative way of producing LC-PUFAs, there is increasing interest in the metabolic engineering of microalgae and genetic modification of algal strains represents a promising strategy to produce sustainable omega-3 oils. Effective recombinant engineering of microalgae to produce increased levels of LC-PUFAs for commercial production would address a global need and microalgae manipulated in this way would be useful as food additives and animal feed, including aquaculture, to meet global demand.

*Phaeodactylum tricornutum* is an unicellular diatom which accumulates up to 30% EPA and only traces of DHA and is considered a good source for the industrial production of EPA (Molina Grima et al., 1996). The first labelling experiments with [14C]acetate suggested that *P. tricornutum* synthesized EPA de novo by elongation and aerobic desaturation of fatty acids (Moreno et al., 1979). In pulse-chase experiments Arao and Yamada have demonstrated that EPA can be synthesized by 4 different routes and that the preferred route involved intermediates of both omega-6 and omega-3 pathways (Arao and Yamada, 1994). The majority of the EPA was found in galactolipids as opposed to neutral lipids such as triacylglycerol (Arao et al., 1987; Yongmanitchai and Ward, 1993). Recently, the genes encoding the Δ5- and Δ6-desaturases involved in EPA biosynthesis in *P. tricornutum* have been cloned and characterized (Domergue et al., 2002). It was shown that both desaturases were microsomal enzymes contributing equally to both pathways and they supported the preferred route acting simultaneously in omega-6 and omega-3 pathways. This suggests that Δ6- and Δ5 -desaturation and Δ6 -elongation involved in biosynthesis of EPA in *P. tricornutum* take place in the endoplasmic reticulum (ER) and newly synthesized EPA is imported after into the plastids. The presence of only minor amounts of all the intermediates of EPA biosynthetic pathway indicates that *P. tricornutum* have developed highly efficient mechanism towards the accumulation of EPA as a single end-product (Arao and Yamada, 1994). In several microalgae DHA can be synthesized by the elongation of EPA to docosapentaenoic acid (DPA; 22:5Δ7,10, 13, 16, 19) by a specific Δ5-elongase, with DPA then converted to DHA by a Δ4-desaturase.

The present invention is aimed at mitigating the shortcomings in the production of LC-PUFAs in various organisms, in particular in algae.

SUMMARY OF THE INVENTION

The invention generally relates to transgenic organisms, in particular transgenic microalgae, with enhanced production of LC-PUFAs, in particular omega-3 LC-PUFAs such as DHA and/or EPA. The transgenic organisms, in particular transgenic microalgae, express one or more heterologous nucleic acid encoding for a polypeptide involved in the LC-PUFAs biosynthesis pathway. The invention also relates to methods for making transgenic organisms, in particular transgenic microalgae, uses of the transgenic organisms, in particular transgenic microalgae, and methods for increasing the production of LC-PUFAs, in particular omega-3 LC-PUFAs, more particular DHA and/or EPA in an organism, in particular microalgae. The invention also relates to isolated nucleic acids and their uses in methods for the enhanced production of LC-PUFAs, in particular omega-3 LC-PUFAs, in transgenic organisms.

The inventors have shown that microalgae can be manipulated using recombinant methods to produce an increased amount of LC-PUFAs, in particular EPA and DHA using heterologous gene expression. The inventors have surprisingly demonstrated that heterologous expression of Δ5-elongase from *Ostreococcus tauri* alone results in increased accumulation of DHA in *P. tricornutum* with DHA levels in transgenic strains reaching up to 13% of total fatty acids. The inventors have also shown that overexpression of OtD6 in *P. tricornutum* has a positive effect on EPA levels. These findings provide evidence for the efficacy of expressing heterologous genes and enhancing the LC-PUFAs biosynthetic pathway through metabolic engineering in transgenic microalgae. Furthermore, other organisms that make EPA/DHA, including animals and plants, can be manipulated in the same way by overexpression of Δ5-elongase from *Ostreococcus tauri*.

Accordingly, in one aspect, the invention relates to a transgenic microalgae with increased production of one or more omega-3 LC-PUFA. In one embodiment, the omega-3 LC-PUFA is selected from DHA and/or EPA. In another aspect, the invention relates to the use of a transgenic microalgae in producing omega-3 LC-PUFAs. In another aspect, the invention relates to a method for producing transgenic microalgae with increased omega-3 LC-PUFAs content. In another aspect, the invention relates to a method for increasing production of one of more omega-3 LC-PUFA in microalgae comprising a) introducing and expressing in a microalgae a heterologous nucleic acid,
b) cultivating said microalgae and
c) obtaining said one of more omega-3 LC-PUFA from the transgenic microalgae.

In another aspect, the invention relates to a method for increasing production of DHA in microalgae. In another aspect, the invention relates to a method for increasing production of EPA in microalgae.

The invention also relates to an oil isolated from a microalgae described herein or a composition comprising a transgenic microalgae described or product therefrom herein and uses thereof.

In another aspect, the invention relates to a method for making a feedstuff comprising
a) cultivating a transgenic microalgae described herein and
b) obtaining said one of more omega-3 LC-PUFA from the transgenic microalgae.

In another aspect, the invention relates to an isolated nucleic acids comprising SEQ ID No. 7 or 9 encoding a Δ6-desaturase (Ost809Δ6) comprising SEQ ID No. 8 or 10, a functional variant thereof or a Δ6-desaturase that has at least 75%, at least 80%, at least 85%, at least 90%, at least 95%, at least 96%, at least 97%, at least 98%, at least 99% homology to SEQ ID No. 8 or 10 and uses thereof. The invention also relates to an isolated nucleic acid comprising SEQ ID No. 15 or 17 encoding a Δ4-desaturase (Ost809Δ4) comprising SEQ ID No. 16 or 18, a functional variant thereof or a Δ4-desaturase that has at least 75%, at least 80%, at least 85%, at least 90%, at least 95%, at least 96%, at least 97%, at least 98%, at least 99% homology to SEQ ID No. 16 or 18 and uses thereof. In another aspect, the invention relates to an isolated nucleic acid comprising SEQ ID No. 19 encoding Δ6-elongase (FcELO6) comprising SEQ ID No. 20, a functional variant thereof or a Δ6-elongase that has at least 75%, at least 80%, at least 85%, at least 90%, at least 95%, at least 96%, at least 97%, at least 98%, at least 99% homology to SEQ ID No. 20 and an isolated nucleic acid comprising SEQ ID No. 21 encoding Δ5-desaturase comprising SEQ ID No. 22, a functional variant thereof or a Δ5-desaturase that has at least 75%, at least 80%, at least 85%, at least 90%, at least 95%, at least 96%, at least 97%, at least 98%, at least 99% homology to SEQ ID No. 22 and uses thereof.

In another aspect, the invention relates to the use of an isolated nucleic described herein in increasing the production of omega-3 LC-PUFAs, in particular DHA and/or EPA, in microalgae or higher plants.

Further, the invention relates to a transgenic organism, preferably a microalgae, with increased DHA levels expressing a heterologous Δ5-elongase.

BRIEF DESCRIPTION OF THE DRAWINGS

The invention is further described in the following non-limiting figures.

Figure 5A:
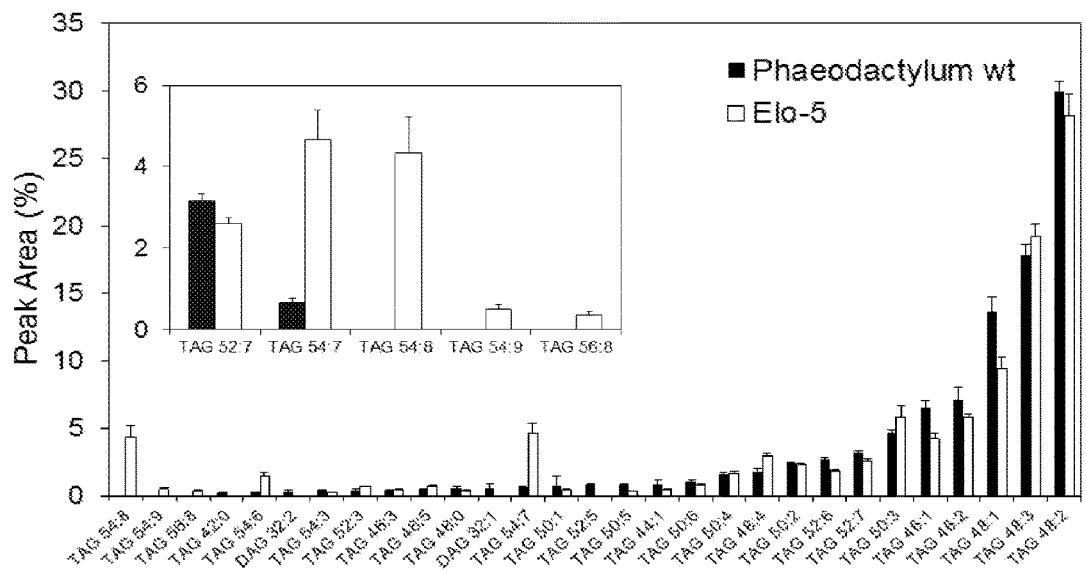
FIG. 5: The distribution of TAG species from WT and transgenic *P. tricornutum* at stationary phase of growth (FIG. 5a).
Figure 5B:
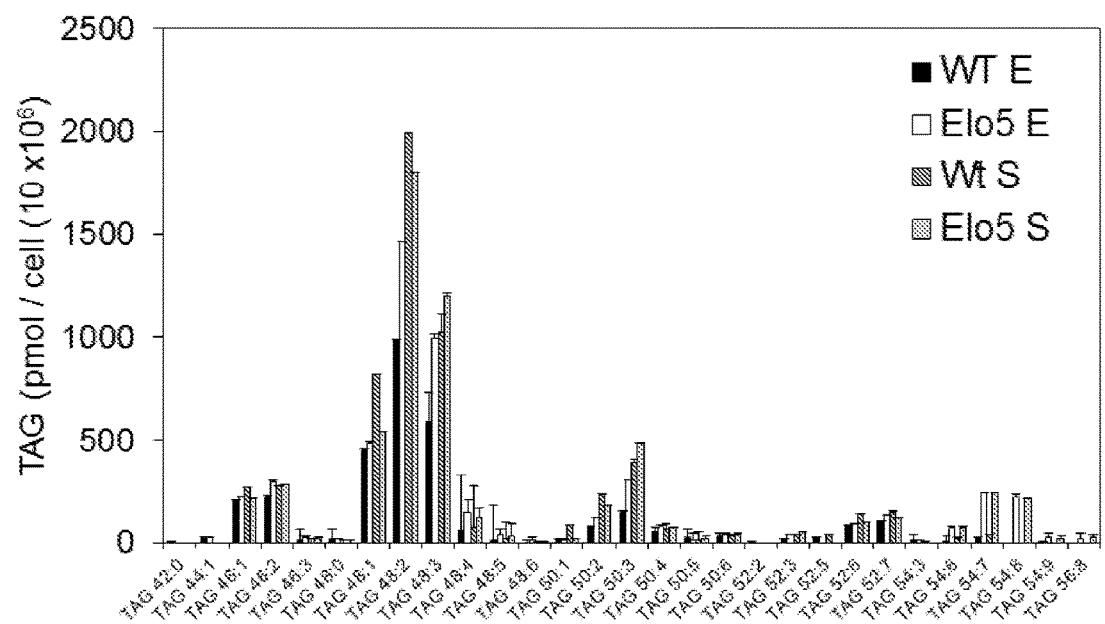

The distribution of TAG species from WT and transgenic *P. tricornutum* at different stages of growth (FIG. 5b).

Figure 6A:
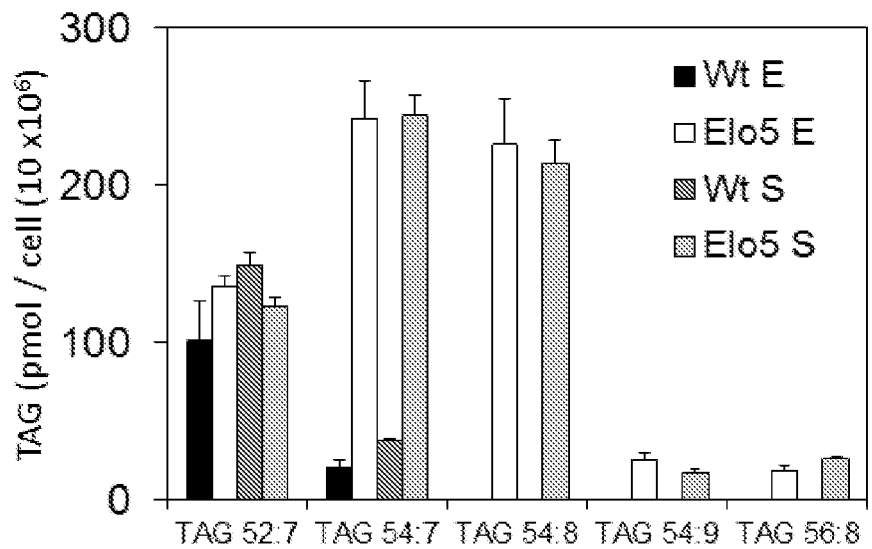
Figure 6B:
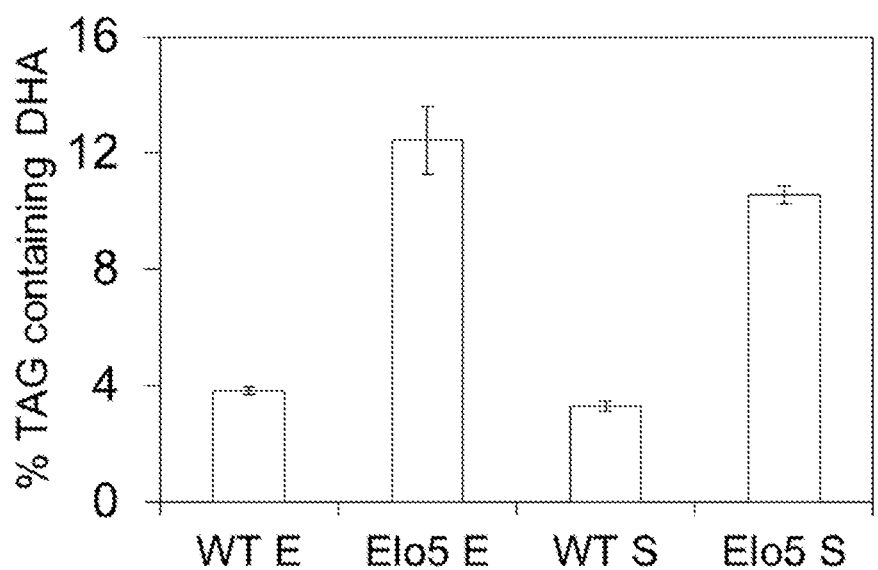

FIG. 6: The distribution of DHA in TAG species from WT and transgenic *P. tricornutum* expressing OtElo5 at different stages of the growth cycle: DHA in specific TAGs (FIG. 6a); % of TAG containing DHA (FIG. 6b).

Figure 7:
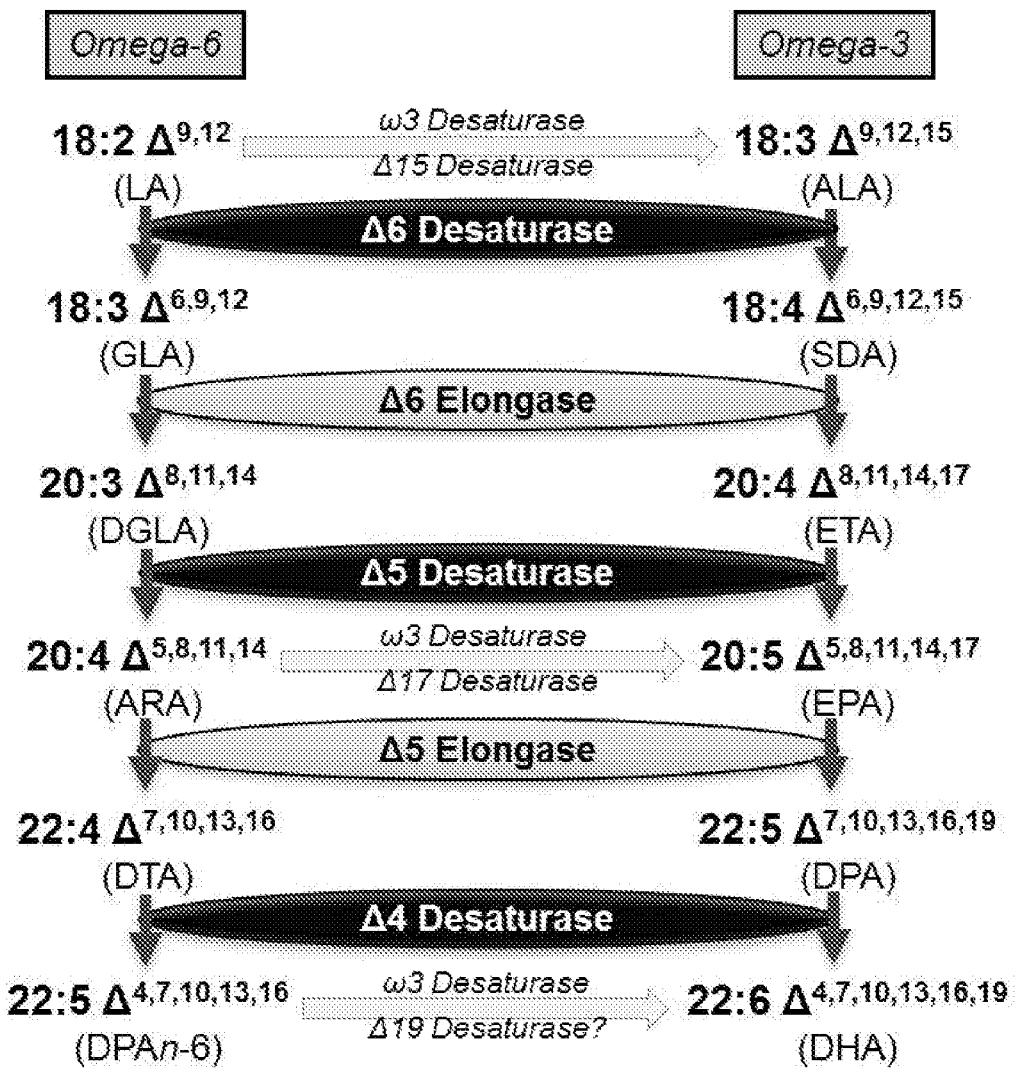

FIG. 7: Omega-3 PUFA biosynthetic pathway (schematic representation).

Figure 8:
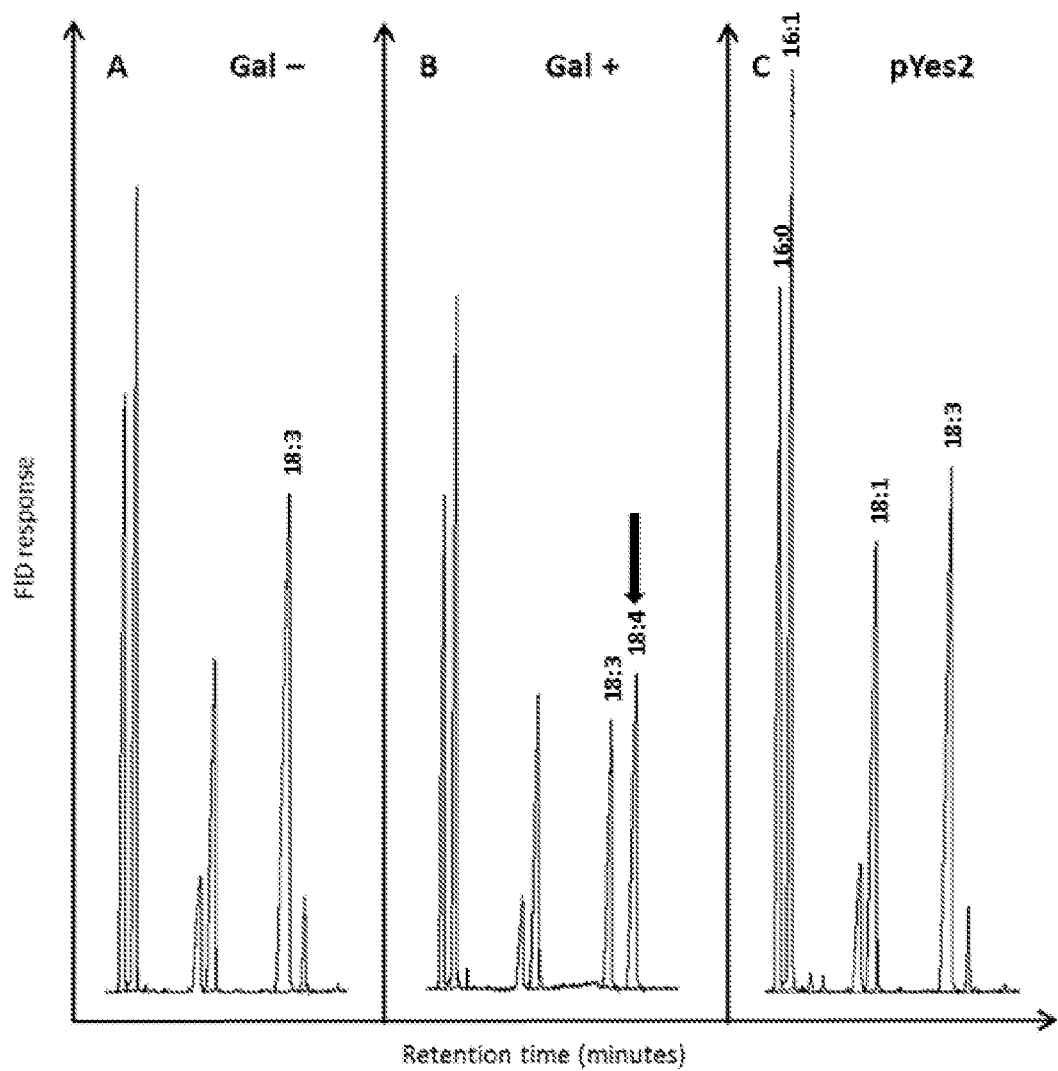

FIG. 8: Expression of Ost809Δ6-desaturase in transgenic yeast in the presence of the exogenous substrate 18:3n-3 (ALA). (BPX72 column). Note the conversion of ALA to the higher unsaturated form (SDA—arrowed). No conversion occurs with yeast strains containing the empty vector (pYES2- C), and only when the expression of the Ost809 desaturase is induced by the addition of galactose (Gal+; B)

Figure 9:
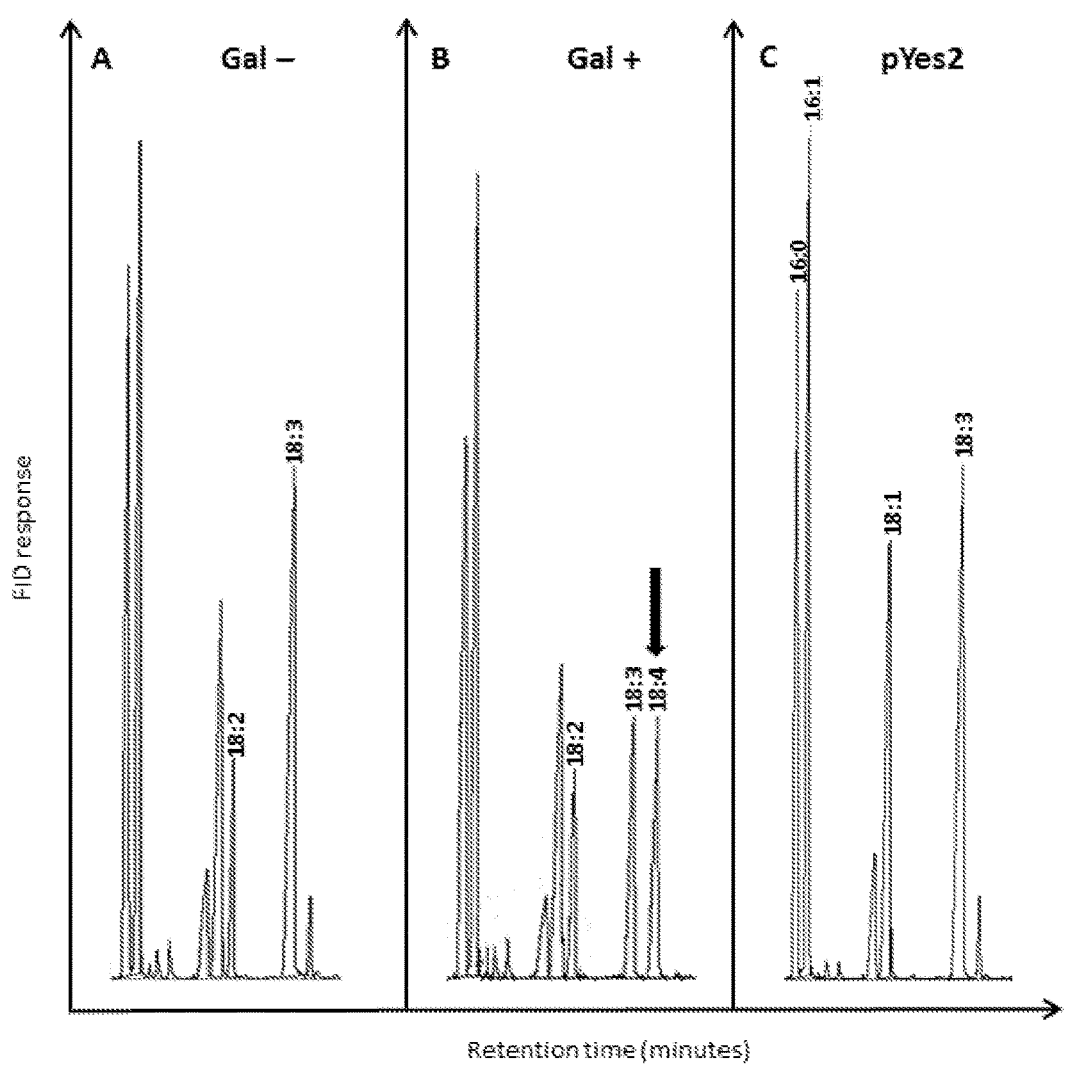

FIG. 9: Functional characterization of Ost809Δ6 in yeast (BPX72 column). Yeast cells supplemented with LA and ALA. Expression of *Ostreococcus* 809 Δ6 in yeast, supplemented with both 18:2 (LA) and 18:3 (ALA). Note the specific conversion of ALA, but not LA, to a higher unsaturated. No conversion occurs with yeast strains containing the empty vector (pYES2- C), and only when the expression of the Ost809 desaturase is induced by the addition of galactose (Gal+; B)

Figure 10:
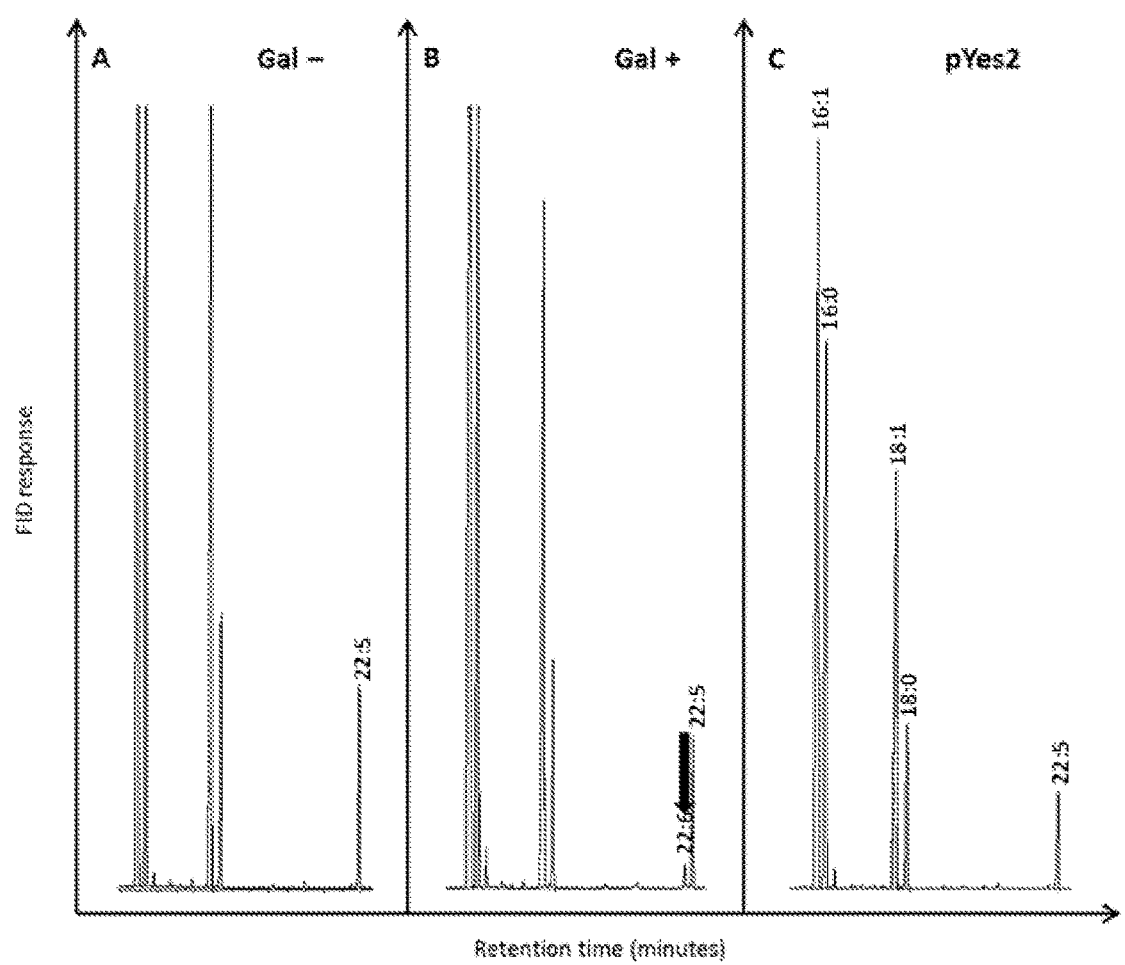

FIG. 10: FAMEs profile of transgenic yeast expressing Ost809Δ4 desaturase in the presence of DPA (C22:5n-3). Expression of *Ostreococcus* 809 Δ4 in yeast cells supplemented with exogenous 22:5 (DPA). Note the conversion of 22:5n-3 to the higher unsaturated form (22:6n-3; DHA—arrowed). No conversion occurs with yeast strains containing the empty vector (pYES2- C), and only when the expression of the Ost809 D4 desaturase is induced by the addition of galactose (Gal+; B). NB. These C22 PUFAs are best resolved on a HP1 GC column—in this case, the (poly)unsaturated fatty acids eluted earlier than less saturated forms—this is the inverse compared to BPX72 column used above.

Figure 11:
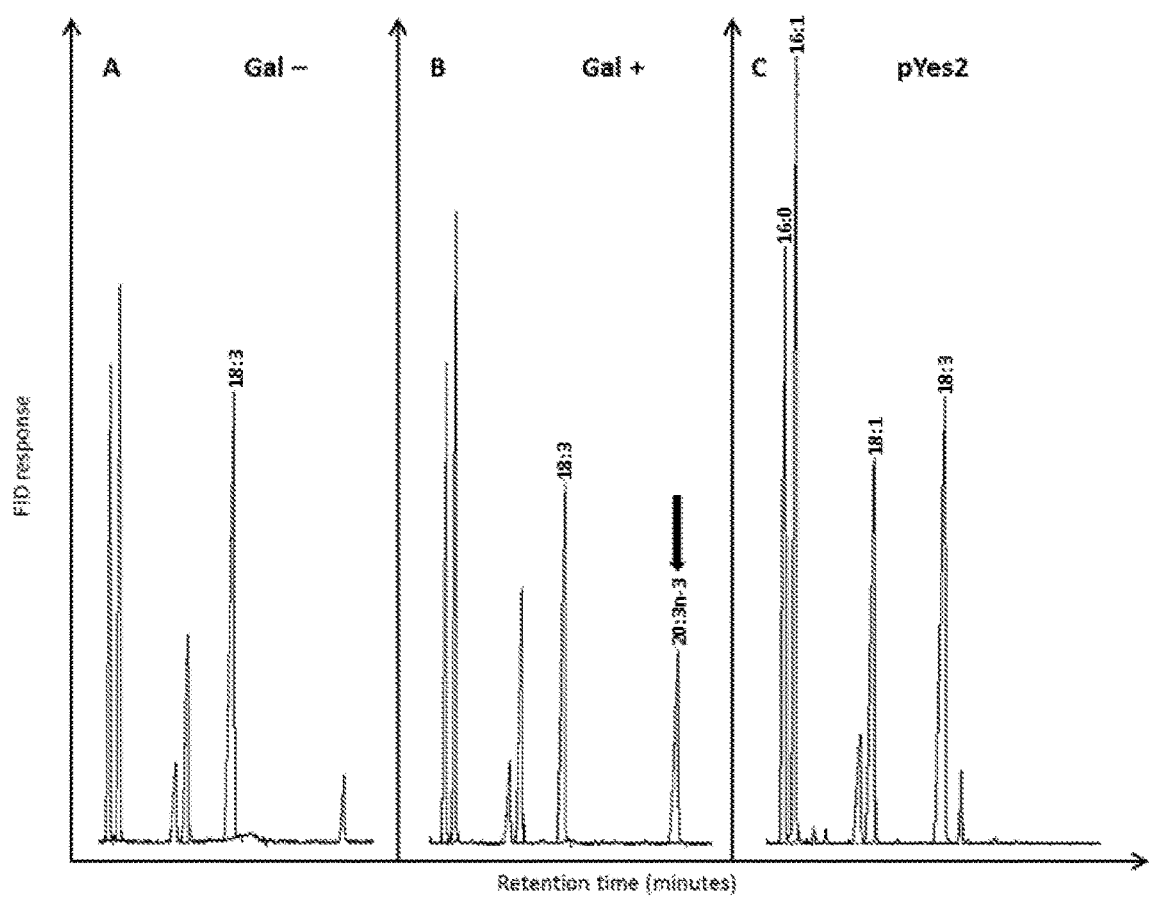

FIG. 11: FAMEs profile of transgenic yeast expressing FcElo6 (BPX72 column). Yeast were supplemented with 18:3n-6 (GLA). Expression of *Fragilariopsis cylindrus* Elo6 in yeast cells supplemented with exogenous 18:3 (GLA). Note the conversion of 18:3 ALA to the elongated form 20:3n-3 (arrowed). No conversion occurs with yeast strains containing the empty vector (pYES2- C), and only when the expression of the *Fragilariopsis* Elo6 is induced by the addition of galactose (Gal+; B).

Figure 12:
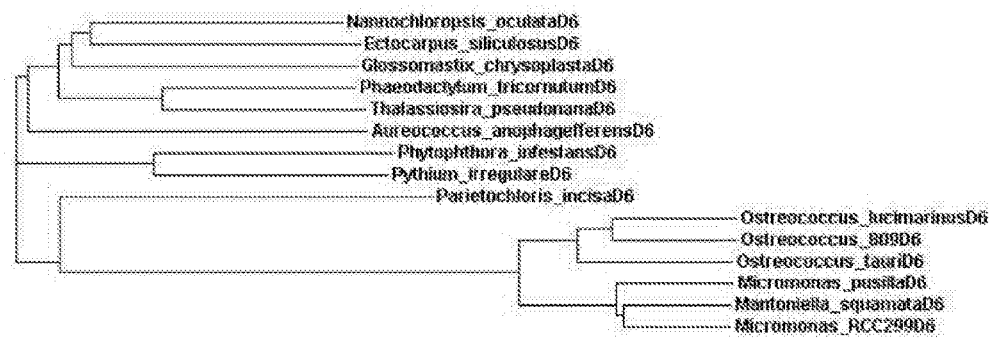

FIG. 12: Phylogenetic tree showing relationship between n-3 specific Ost809Δ6 desaturase and other Δ6-desaturases.

Figure 13:
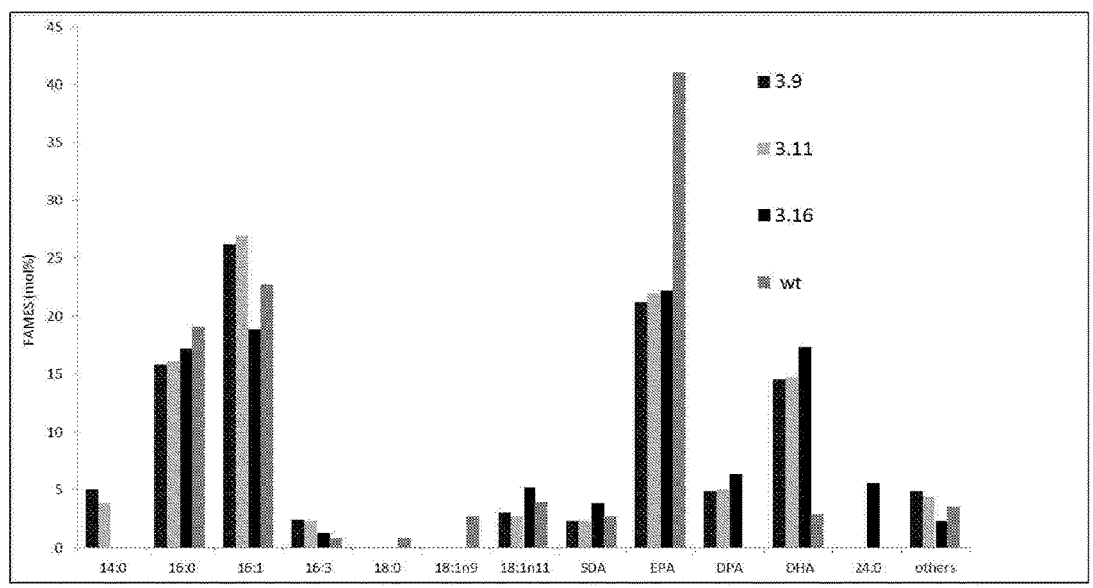

FIG. 13: Expression of FcElo6 resulted in increase of DHA levels up to 14-17%. GC-MS analysis of total FA profiles from Pt cells expressing FcElo6.

Figure 14:
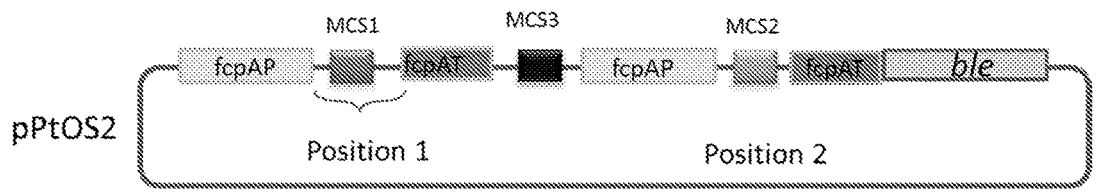

FIG. 14: Schematic representation of vector system pPTOS2.

Figure 15:
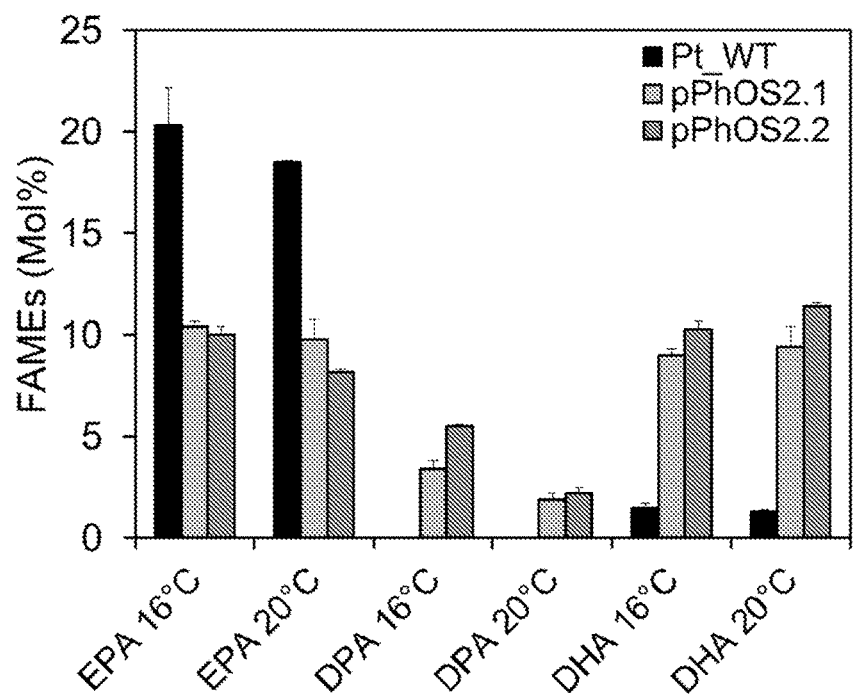

FIG. 15: Co-expression of two heterologous omega-3 LC-PUFA biosynthetic activities in *P. tricornutum*. Fatty acid composition of Pt_WT, pPhOS2.1 (expressing OtElo5) and pPhOS2.2 (expressing OtD6Pt and OtElo5) cells during the S phase of growth at 16° C. and 20° C. Values are the average of three experiments (+/− standard error).

Figure 16:
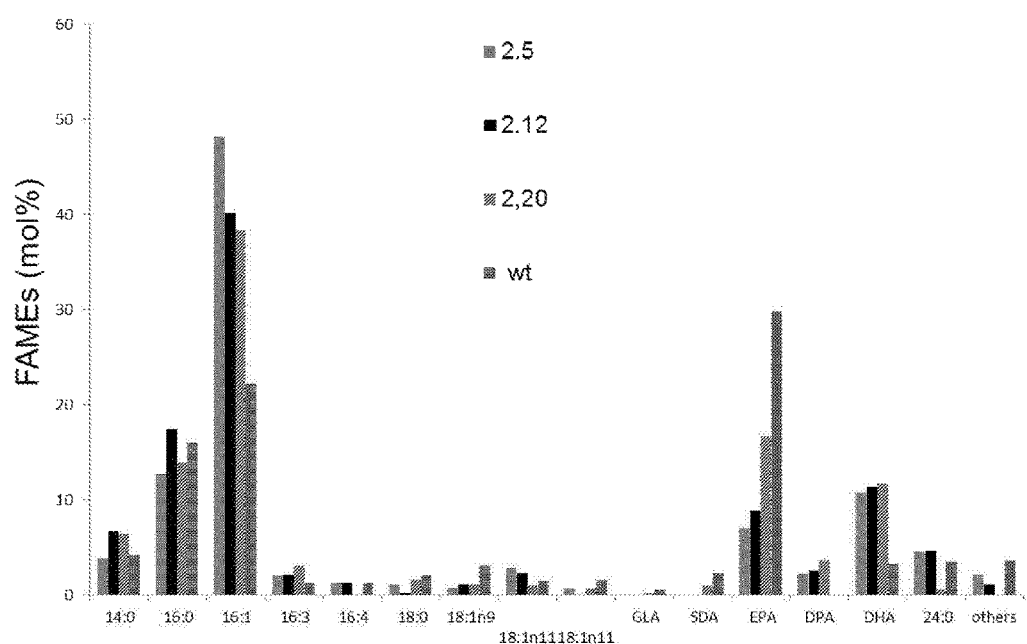

FIG. 16: Fatty acid composition of pPhOS_Ppglut (expressing OtElo5 and Ppglucose transporter) cells during the S phase of growth at 20° C., 100 μmol m$^{-2}$s$^{-1}$ under constant agitation at 70 rpm. N=1.

Figure 17:
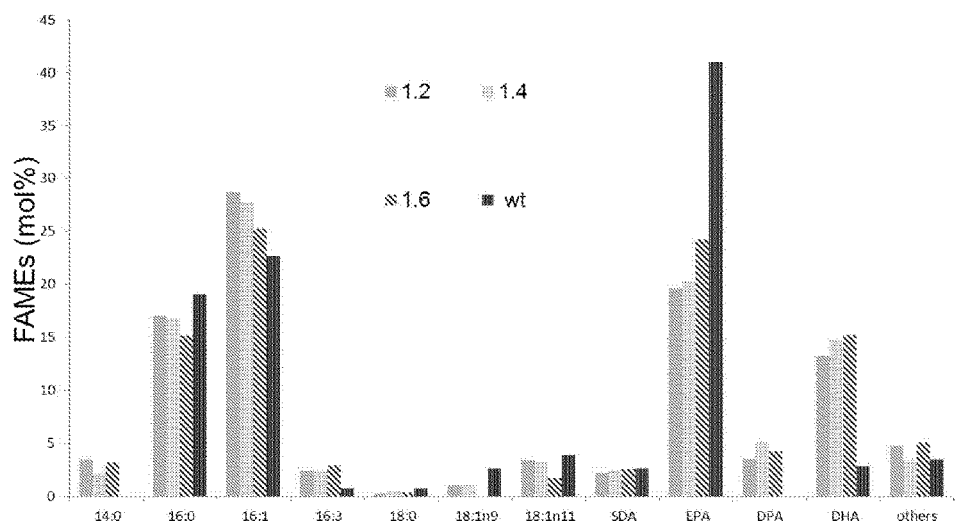

FIG. 17: Fatty acid composition of pPhOS_Hsglut (expressing OtElo5 and human glucose transporter) cells during the S phase of growth at 20° C., 100 μmol m$^{-2}$s$^{-1}$ under constant agitation at 70 rpm. N=1.

Figure 18:
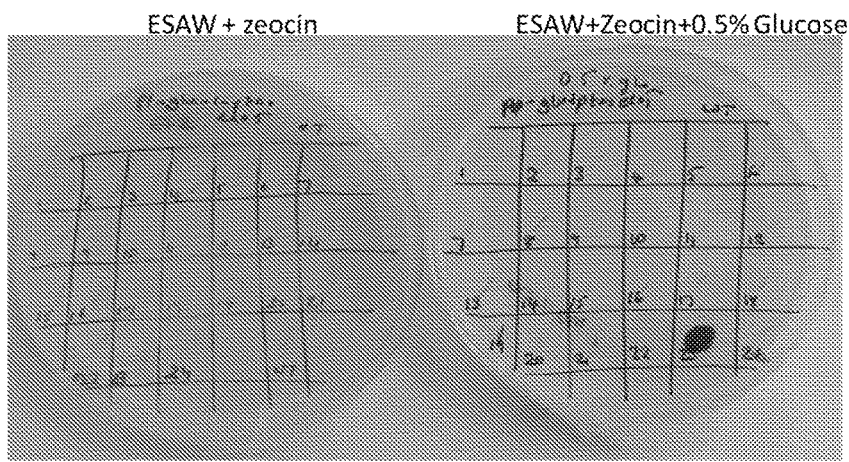

FIG. 18: Growth of Wt and pPhOS_Ppglut Pt cells in the dark.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of microbiology, tissue culture, molecular biology, chemistry, biochemistry and recombinant DNA technology, which are within the skill of the art. Such techniques are explained fully in the literature.

The invention relates to the genetic manipulation of the fatty acid biosynthetic pathway in microalgae. In particular, the invention relates to methods for increasing the production of LC-PUFAs, in particular omega-3 LC-PUFAs, for example one of more omega-3 LC-PUFA in an organism, in particular in microalgae.

Polyunsaturated fatty acids can be classified into two major families, depending on the position (n) of the first double bond nearest the methyl end of the fatty acid carbon chain. Thus, the omega-6 fatty acids ($\varpi$ -6) have the first unsaturated double bond six carbon atoms from the omega (methyl) end of the molecule and additionally have a total or two or more double bonds, with each subsequent unsaturation occurring 3 additional carbon atoms toward the carboxyl end of the molecule. In contrast, the omega-3 fatty acids ($\varpi$ -3) have the first unsaturated double bond three carbon atoms away from the omega end of the molecule and additionally have a total of three or more double bonds with each subsequent unsaturation occurring 3 additional carbon atoms towards the carboxyl end of the molecule.

Table I summarizes the common names of omega-3 fatty acids and the abbreviations that will be used throughout the specification:

TABLE I

| Common Name | Abbreviation | Shorthand notation |
|---|---|---|
| oleic acid | OA | 18:1$^{\Delta 9}$ |
| Linoleic acid | LA | 18:2$^{\Delta 9,12}$ |
| γ-Linolenic acid | GLA | 18:3$^{\Delta 6,9,12}$ |
| di-homo γ-linolenic acid | DGLA | 20:3$^{\Delta 8,11,14}$ |
| Arachidonic acid | ARA | 20:4$^{\Delta 5,8,11,14}$ |
| α-linolenic acid | ALA | 18:3$^{\Delta 9,12,15}$ |
| stearidonic acid | SDA | 18:4$^{\Delta 6,9,12,15}$ |
| eicosatetraenoic acid | ETA | 20:4$^{\Delta 8,11,14,17}$ |
| eicosapentaenoic acid | EPA | 20:5$^{\Delta 5,8,11,14,17}$ |
| docosapentaenoic acid | DPA | 22:5$^{\Delta 7,10,13,16,19}$ |
| docosahexaenoic acid | DHA | 22:6 $^{\Delta 4,7,10,13,16,19}$ |

There are a number of enzymes that are involved in the omega-3 PUFA biosynthetic pathway as shown in FIG. 7. These include desaturases and elongases.

A variety of genes involved in oil production have been identified through genetic means in different organisms and the DNA sequences of some of these genes are publicly available. Non-limiting examples are shown below:
Accession No. Description
AY131238 *Argania spinosa* Δ6-desaturase
Y055118 *Echium pitardii* var. *pitardii* Δ6-desaturase
AY055117 *Echium gentianoides* Δ6-desaturase
AF296076 *Mucor rouxii* Δ6-desaturase
AF007561 *Borago officinalis* Δ6-desaturase
L11421 *Synechocystis* sp Δ6-desaturase
NM_031344 *Rattus norvegicus* Δ6 fatty acid desaturase
AF465283, *Moritierella alpine* Δ6 fatty acid desaturase
AF465282 *Moritierella isabellina* Δ6 fatty acid desaturase
AF419296 *Pythium irregulare* Δ6 fatty acid desaturase
AB052086 *Mucor circinelloides* D6d mRNA for Δ6 fatty acid desaturase AJ250735 *Ceratodon purpureus* mRNA for Δ6 fatty acid desaturase
AF126799 *Homo sapiens* Δ6 fatty acid desaturase
AF126798 *Mus musculus* Δ6 fatty acid desaturase
AF199596, *Homo sapiens* Δ5 desaturase
AF320509 *Rattus norvegicus* liver Δ5 desaturase
AB072976 *Mus musculus* D5D mRNA for Δ5 desaturase
AF489588 *Thraustochytrium* sp. ATCC21685 Δ5 desaturase
AJ510244 *Phytophthora megasperma* mRNA for Δ5 fatty acid desaturase
AF419297 *Pythium irregulare* Δ5 fatty acid desaturase
AF07879 *Caenorhabditis elegans* Δ5 fatty acid desaturase
AF067654 *Mortierella alpina* Δ5 fatty acid desaturase
AB022097 *Dictyostelium discloideum* mRNA for Δ5 fatty acid desaturase
AF489589.1 *Thraustochytrium* sp. ATcc21685 Δ4 fatty acid desaturase
AY332747 *Pavlova lutheri* Δ4 fatty acid desaturase (des1) mRNA
AAG36933 *Emericella nidulans* oleate Δ12 desaturase
AF110509, *Mortierella alpina* Δ12 fatty acid desaturase mRNA
AAL13300 *Mortierella alpina* Δ12 fatty acid desaturase mRNA
AF417244 *Mortierella alpine* ATCC 16266 Δ12 fatty acid desaturase
AF161219 *Mucor rouxii* Δ12 desaturase mRNA
X86736 S *Piruline platensis* Δ12 desaturase
AF240777 *Caenorhabdtitis elegans* Δ12 desaturase
AB007640 *Chlamydomonas reinhardtii* Δ12 desaturase
AB075526 *Chorella vulgaris* Δ12 desaturase
AP002063 *Arabidopsis thaliana* microsomal Δ12 desaturase
NP_441622, *Synechocystis* sp. PCC6803 Δ15 desaturase
AAL36934 *Perilla frutescens* Δ15 desaturase All references to sequence IDs herein are specifically incorporated by reference.

Additionally, the patent literature provides many additional DNA sequences of genes (and/or details concerning several of the genes above and their methods of isolation) involved in polyunsaturated fatty acid production (see, for example: U.S. Pat. No. 5,968,809 (Δ5-desaturases); U.S. Pat. Nos. 5,972,664 and 6,075,183 (Δ5 desaturases); WO 91/13972 and U.S. Pat. No. 5,057,419 (Δ9-desaturases); WO 93/11245 (Δ15-desaturases); WO 94/11516. U.S. Pat. No. 5,443,974 and WO 03/099216 (Δ12-desaturases); U.S. 2003/0196217 A1 (Δ17-desaturase); WO 02/090493 (Δ4-desaturases); and WO 00/12720 and U.S. 2002/0139974A1 (elongases)).

The term "desaturases" as used herein refers to a polypeptide component of a multi-enzyme complex that can desaturate, i.e. introduce a double bond in one or more fatty acids to produce a mono- or polyunsaturated fatty acid or precursor of interest. Some desaturates have activity on two or more substrates. It may be desirable to empirically determine the specificity of a fatty acid desaturase by transforming a suitable host with the gene for the fatty acid desaturase and determining its effect on the fatty acid profile of the host. Nucleic acids that encode for desaturases are isolated from various organisms can be used according to the various aspects of the invention and examples are described herein, including *Ostreococcus* sp.

Desaturases include omega-3-desaturase, Δ6-desaturase, Δ5-desaturase, Δ12-desaturase, Δ19-desaturase, Δ17-desaturase and Δ4-desaturase.

The term "elongase" as used herein refers to a polypeptide that can elongate a fatty acid carbon chain to produce an acid two carbons longer than the fatty acid substrate that the elongase acts upon. Nucleic acids that encode for elongases isolated from various organisms can be used according to the various aspects of the invention and examples are described herein, including *Ostreococcus* sp.

Examples of reactions catalyzed by elongase systems are the conversion of GLA to DGLA, SDA to ETA, ARA to DTA and EPA to DPA. In general, the substrate selectivity of elongases is somewhat broad but segregated by both chain length and the degree and type of unsaturation.

For example, a C14/16 elongase will utilize a C14 substrate (e.g., myristic acid), a C16/18 elongase will utilize a C16 substrate (e.g., palmitate), a C18/20 elongase will utilize a C18 substrate (e.g., GLA, SDA, LA, ALA) and a C20/22 elongase (also referred to as a Δ5-elongase) will utilize a C20 substrate (e.g., ARA, EPA).

Since some elongases have broad specificity, a single enzyme may be capable of catalyzing several elongase reactions (e.g., thereby acting as both a C16/18 elongase and C18/20 elongase). It may be desirable to empirically determine the specificity of a fatty acid elongase by transforming a suitable host with the gene for the fatty acid elongase and determining its effect on the fatty acid profile of the host.

Elongases include Δ6-, Δ5- and Δ9-elongases. Δ5-elongase is not generally viewed as rate limiting in the production of DHA and it is generally assumed that the first step in the LC-PUFA pathway, the D6-saturation, is rate-limiting.

Embodiments of the invention relating to the production of omega-3 LC-PUFAs in transgenic microalgae are described below. A skilled person would understand that these embodiments are not limited to transgenic microalgae, but can be applied to other organisms to produce omega-3 LC-PUFAs. The organism may be an animal, for example a mammal. In one embodiment, humans are specifically excluded. In another embodiment, the organism is a plant, for example a crop plant.

In a first aspect, the invention relates to a transgenic microalgae with increased production of omega-3 LC-PUFAs, for example one or more omega-3 LC-PUFA or total omega-3 LC-PUFA content. According to the various aspects of the invention, the omega-3 LC-PUFAs may be selected from SDA, ETA, EPA, DPA or DHA. In one embodiment, the omega-3 LC-PUFAs is DHA. In another embodiment, the omega-3 fatty acid is EPA.

According to the various aspects of the invention described herein, the increase in the production of DHA or EPA is measured as an individual content of different omega-3 LC-PUFAs in total fatty acids (TFA). In other words, the increase is measured as a percentage of the total fatty acid content. Preferably, the increase is at least 2%, 3%, 4%, 5%, 6%, 7%, 8%, 9%, 10%, 11%, 12%, 13%, 14%, 15% or more compared to a control microalgae (mol %).

In one embodiment, the omega-3 LC-PUFAs is DHA. In the transgenic microalgae of the invention, the DHA content is increased by at least 1%, 2%, 3%, 4%, 5%, 6%, 7%, 8%, 9%, 10%, 11%, 12%, 13%, 14%, 15% or more compared to a control microalgae. In one embodiment, the omega-3 LC-PUFAs is DHA. In the transgenic microalgae of the invention, the DHA content is at least 2, at least 3, at least 4, at least 5, at least 6, at least 7, at least 8, at least 9 or at least 10 fold higher than in a control microalgae. Preferably, the total DHA content is at least 10% of the total fatty acid content (mol %).

In another embodiment, the omega-3 LC-PUFAs is EPA. In the transgenic microalgae according to the various aspects of the invention, the EPA content is increased by at least 2%, 3%, 4%, 5%, 6%, 7%, 8%, 9%, 10%, 11%, 12%, 13%, 14%, 15%. Preferably, the total EPA content is at least 20% of the total fatty acid content (mol %).

According to the various aspects of the invention, the total fatty acid content, LC-PUFAs content, omega-3 LC-PUFAs content or the content of individual fatty acids such as DHA is increased compared to a control microalgae. A control microalgae as used herein is a microalgae which has not been modified according to the methods of the invention. Accordingly, the control microalgae has not been genetically modified to express a nucleic acid as described herein to alter LC-PUFA content. In one embodiment, the control microalgae is a wild type microalgae. In another embodiment, the control microalgae is a microalgae that does not carry a transgene according to the methods described herein, but expresses a different transgene. The control microalgae is typically of the same algae species.

The term "total fatty acids content" herein refers to the sum of all cellular fatty acids that can be derivitized to fatty acid methyl esters by the base transesterification method in a given sample (known as the art, for example as described in Sayanova et al., (1997); Sayanova et al., (2003) FEBS Lett. 2003 May 8;542(1-3):100-4).

According to the various aspects of the invention, the increase is measured in the stationary phase.

According to the various aspects of the invention, the term microalgae encompasses all microalgae which have the capacity to make LC-PUFAs. The algae may be a heterotrophic or autothrophic algae.

A skilled person would know that the term "microalgae" includes unicellular, photosynthetic microorganisms from several distinct biological groups, comprising, for example, eukaryotic chlorophyta, rhodophyta, heterokont, haptophyta divisions of algae and prokaryotic cyanobacteria.

EPA has been found in a wide variety of marine microalgae including in the classes Bacillariophyceae (diatoms), Chlorophyceae, Chrysophyceae, Cryptophyceae, Eustigamatophyceae and Prasinophyceae (see Table II). Accordingly, according to the various aspects of the invention, the microalgae may be selected from these orders, classes or species.

According to the various aspects of the invention, the microalgae may be selected from a microalgae listed in Table II.

TABLE II

Proportions of PUFAs in marine microalgae
*Emiliania huxleyiis the now accepted name for Coccolithus huxleyi
Omega-3 LC-PUFAs (% of Total Fatty acids)

| Mircoalgae sp. (Order/class/sp.) | EPA | DHA | References |
|---|---|---|---|
| Chlorophyta (green algae) Chlorophyceae | | | |
| Chlorella minutissima | 45.0 | — | Seto et al., (1984) |
| Prasinophyceae | | | |
| Ostreococcus tauri | 2.0 | 12.0 | Wagner M. et al., (2010) |
| Ostreococcus lucimarinus | 2.1 | 3.8 | Ahmann et al., (2011) |
| Hetermastrix rotundra | 28 | 7 | Yongmanitchai and Ward, (1989) |
| Haptophyta Pavlovophyceae | | | |
| Pavlova lutheri | 11.6 | 9.1 | Tonon et al., (2002) |
| Prymnesiophyceae | | | |
| Isochrysis galbana | 22.6 | 8.4 | Molina Grima et al., (1995) |
| Emilinaia huxleyi * | 17 | — | Yongmanitchai and Ward, (1989) |
| Cryptophyceae Cryptomonadaceae | | | |
| Cryptomonas maculate | 17 | — | Yongmanitchai and Ward, (1989) |
| Chromonas sp. | 12 | 6.6 | Renaud et al., (1999) |
| Cryptomonas sp. | 16 | 10 | Yongmanitchai and Ward, (1989) |
| Rhodomonas sp. | 8.7 | 4.6 | Renaud et al., (1999) |
| Heterokont Bacillariophyceae (diatoms) | | | |
| Asterionella japonica | 20 | — | Yongmanitchai and Ward, (1989) |
| Amphora coffeaformis | 1.39 | 0.39 | Renaud et al., (1999) |
| Bidduiphia sinensis | 24.0 | 1.0 | Yongmanitchai and Ward, (1989) |
| Chaetoceros sp. | 16.7 | 0.8 | Renaud et al., (1999) |
| Cylindrotheca fusiformis | 18.8 | — | Tan and Johns, (1996) |
| Fragilaria pinnata | 6.8 | 1.0 | Renaud et al., (1999) |
| Nitzchia angularis | 21 | — | Kyle et al., (1992) |
| Navicula incerta | 25.2 | — | Tan and Johns, (1996) |
| Navicula pelliculosa | 9.4 | — | Tan and Johns, (1996) |
| Navicula saprophila | 16.0 | — | Kitano et al., (1997) |
| Nitzschia closterium | 15.2 | — | Renaud et al., (1994) |
| Nitzschia frustulum | 23.1 | — | Renaud et al., (1994) |
| Nitzschia laevis | 19.1 | — | Wen and Chen, (2001) |
| Phaeodactylum tricornutum | 34.5 | — | Yongmanitchai and Ward, (1991) |
| Skeletonema costatum | 29.2 | 3.4 | Blanchemain and Grizeau, (1999) |
| Thalassiosira pseudonana | 12.2 | — | Tonon et al., (2002) |
| Chrysophyceae (golden algae) | | | |
| Monochrysis lutheri | 19 | — | Yongmanitchai and Ward, (1989); Kyle, (1992) |
| Pseudopedinella sp. | 27 | — | Yongmanitchai and Ward, (1989) |
| Crisosphaera carterae | 20 | — | Yongmanitchai and Ward, (1989) |
| C.elongate | 28 | — | Yongmanitchai and Ward, (1989) |
| Eustigmatophyceae | | | |
| Nannochioropsis salina | 15 | — | Yongmanitchai and Ward, (1989) |
| Nannochioropsis sp. | 35 | — | Sukenik, (1991) |
| Nannochioris sp. | 27 | — | Yongmanitchai and Ward, (1989) |
| Monodus subterraneus | 32.9 | — | Quiang et al., (1997) |

In one embodiment, autotrophic microalgae which are as the primary producers of PUFAs are preferred. For example, the microalgae may be selected from *Phaeodactylum, Nannochloropsis, Thraustochytrium* or *Schizochytrium*. Other genera include *Spirulina, Dunaliella, Chlorella, Thalassiosira, Isochrysis, Porphyridium, Nannochloropsis, Pavlova, Chaetoceros, Crypthecodinium, Fraigilariopsi* and *Nitzshia*.

For example, the microalgae may be selected from *Chaetoceros calcitrans, Isochrysis galbana, Pavlova lutheri, Pseudoisochrysis paradoxa, Tetraselmis suecica* and *Skeletonema costatum, Nannochloropsis oculata, Thalassio-* sira pseudonana, Pavlova lutheria, Porphyridium irregular, Crypthecodinium Porphyridium purpureum and Porphyridium cruentum.

In one embodiment, the microalgae is a diatom. Diatoms are brown algae found throughout marine and freshwater ecosystems that are responsible for around 20% of global primary productivity. A defining feature of diatoms is their ornately patterned silicified cell wall (known as frustule), which display species-specific nanoscale-structures.

The diatom may be a centric diatoms or a pennate diatom. In one embodiment, the diatom belongs to the order of Naviculales. In one embodiment, the diatom is *P. tricornutum* or *Thalassiosira pseudonana*. In a preferred embodiment, the diatom is *P. tricornutum*. In another embodiment, the diatom is *Fragilariopsis* sp. for example *Fragilariopsis cylindrus*.

A skilled person would understand that the aspects of the invention are not limited to *P. tricornutum*. Indeed, a skilled person would understand that the invention can be applied to any microalgae that has the capacity to synthesise EPA and/or DHA.

The transgenic microalgae according to the various aspects of the invention expresses one or more heterologous transgenes which encode for one or more nucleic acid involved in the biosynthesis of LC-PUFAs. "Heterologous" with respect to sequence means a sequence that originates from a foreign species, or, if from the same species, is substantially modified from its native form in composition and/or genomic locus by deliberate human intervention. The heterologous transgene is preferably derived or isolated from a microalgae. In one embodiment, the heterologous transgene is derived or isolated from *Prasinophyceae*, for example *Ostreococcus* sp. Sequences of heterologous transgenes may be modified to be codon optimised for expression in the target organism. Thus, the invention relates to transgenic organisms obtained through recombinant methods.

For example, the heterologous transgene may encode for one or more of a Δ15-desaturase, a Δ6-desaturase, a Δ5-desaturase, a Δ4-desaturase, a Δ12-desaturase, a Δ5-elongase, Δ6-elongase or combinations thereof.

In one embodiment, the transgenic microalgae expresses a heterologous nucleic acid encoding a Δ5-elongase. Thus, in one aspect, the invention relates to a transgenic microalgae expressing a nucleic acid encoding a Δ5-elongase. For example, the transgenic microalgae expresses a nucleic acid encoding a Δ5-elongase, but does not express any other transgene encoding for a polypeptide involved in the regulation of the LC-PUFAs biosynthetic pathway. In other embodiments, the transgenic microalgae expresses a nucleic acid encoding a Δ5-elongase and one or more additional heterologous transgene involved in the regulation of the LC-PUFAs biosynthetic pathway, for example a Δ6-desaturase such as OtD6 as shown in example 4. Thus, embodiments where nucleic acids encoding a Δ5-elongase and a Δ6-desaturase are co-expressed are specifically part of the invention. Δ5-elongases and Δ6-desaturases are as defined herein.

In one embodiment, the transgenic microalgae described herein co-expresses a heterologous nucleic acid which is not involved in the regulation of the LC-PUFAs biosynthetic pathway, for example a glucose transporter gene as shown in example 5 together with a heterologous nucleic acid involved in the regulation of the LC-PUFAs biosynthetic pathway such as OtElo5. As shown in the example, a vector can be used allowing co-expression of two heterologous nucleic acids involved in the regulation of different traits—one for omega-3s, and one which allows the alga to be grown in the dark, by the expression of a glucose transporter. If the cells are then provided with an exogenous carbon source such as glucose, they can grow in the dark. Thus, in one embodiment, an exogenous carbon source such as glucose is provided when culturing algae expressing a gene involved in the regulation of the LC-PUFAs biosynthetic pathway such as OtElo5 and a glucose reporter. Examples of nucleic acids that can be used according to the invention encoding a glucose reporter are shown in SEQ ID No. 23 and SEQ ID No. 25. Respective peptides are shown in SEQ ID No. 24 and SEQ ID No. 26.

As used herein, the words "nucleic acid", "nucleic acid sequence", "nucleotide", or "polynucleotide" are intended to include DNA molecules (e.g. cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in genomic sequence, or may comprise only a coding sequence as in cDNAs, and/or may include cDNAs in combination with regulatory sequences. In one embodiment of the various aspects of the invention, cDNA sequences synthetic (deduced) open reading frames, analogous to cDNA are preferred.

For the purposes of the invention, "transgenic", "transgene" or "recombinant" means with regard to, for example, a nucleic acid sequence, an expression cassette, gene construct, a vector or an autonomous replicating element such as an artificial chromosome comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, such as mutagenesis, it being possible for the modification to take the form of, for example, a substitution, addition, deletion, inversion or insertion of one or more nucleotide residues. The natural genetic environment is understood as meaning the natural genomic or chromosomal locus in the original microalgae or the presence in a genomic library.

A transgenic microalgae for the purposes of the invention is thus understood as meaning a microalgae which comprises within its nuclear and or plastidial genome a heterologous polynucleotide. The heterologous polynucleotide is preferably stably integrated within the genome such that the polynucleotide is passed on to successive generations. The heterologous polynucleotide may be integrated into the genome alone or as part of a recombinant DNA construct.

In the context of the present invention, a Δ5-elongase catalyzes the conversion of EPA to DPA. Thus, any nucleic acid that encodes a Δ5-elongase that catalyzes the conversion of EPA to DPA may be used according to the various aspects of the invention as a transgene. In one embodiment, the Δ5-elongase used in the present invention is derived or isolated from *Ostreococcus*, preferably *Ostreococcus tauri*. Preferably, the Δ5-elongase is OtElo5 derived or isolated from *Ostreococcus tauri*. In one embodiment, the transgenic microalgae according to the invention expresses a nucleic acid comprising SEQ ID No. 1, a functional variant thereof or a sequence that encodes for a Δ5-elongase wherein said elongase has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to SEQ ID No. 2. In a preferred embodiment, the microalgae is *P. triconutum* and the nucleic acid encodes a Δ5-elongase comprising or consisting of SEQ ID No. 2.

A functional variant as used according to the aspects of the invention is a biologically active variant. For example, a biologically active variant of SEQ ID No. 1 is a nucleic acid sequence, which, when expressed in a microalgae such as *P. tricornutum*, increases production of DHA. The term variant includes sequences which have been altered for codon optimisation for expression in the target organism for example for expression in *P. tricornutum*.

Thus, it is understood, as those skilled in the art will appreciate, that the aspects of the invention, which use certain polynucleotides including the methods and uses, encompasses more than the sequence specified, but also include alterations in the peptide that do not affect the biological function. For example, alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

In one embodiment, the said nucleic acid according to the various aspects of the invention is operably linked to a regulatory sequence.

The terms "regulatory element" is used interchangeably herein with "control sequence" and "promoter" and all terms are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

Suitable promoters are identified in the examples. For example, if the microalgae is *P. tricornutum*, the promoter may be the *P. tricornutum* promoter fcpA. However, a skilled person would understand that other promoters can also be used. For example, suitable promoters may also be selected from inducible promoters which respond to specific environmental or chemical stimuli.

The term "operably linked" as used herein refers to a functional linkage between the promoter sequence and the gene of interest, such that the promoter sequence is able to initiate transcription of the gene of interest.

The transgene may be part of a vector which, in addition to one or more regulatory sequences also comprises selection markers. These are known in the art. Transformation of microalgae may be carried out by standard procedures known in the art, for example by particle bombardment or electroporation.

The transgenic microalgae expressing a nucleic acid encoding a Δ5-elongase is characterised by an increase in DHA and DPA compared to a control microalgae. In particular, the increase, as measured as a percentage of the total fatty acid content is at least 2, at least 3, at least 4, at least 5, at least 6, at least, at least 8, at least 9 or at least 10 fold higher than in a control microalgae. Specifically, the DHA content is at least 2, at least 3, at least 4, at least 5, at least 6, at least, at least 8, at least 9 or at least 10 fold higher than in a control microalgae. Preferably, the total DHA content is at least 10% of the total LC-PUFAs content (% mol). In one embodiment, the transgenic microalgae expressing a nucleic acid encoding a Δ5-elongase does not express a second transgene encoding for another polypeptide involved in the regulation of the LC-PUFAs pathway, preferably in the regulation of the omega-3 LC-PUFAs pathway.

In one embodiment of the various aspects of the invention, the transgenic microalgae expressing a heterologous nucleic acid encoding a Δ5-elongase may further express one or more additional heterologous nucleic acid encoding for one or more polypeptide involved in the regulation of the LC-PUFAs pathway, preferably in the regulation of the omega-3 LC-PUFAs pathway. In other words, the transgenic microalgae comprises one or more further transgene encoding for one or more polypeptide involved in the regulation of the LC-PUFAs pathway. The polypeptide is preferably selected from any desaturase or elongase involved in the omega-3 PUFA biosynthetic pathway as shown in FIG. 7. Any combination of desaturase and elongase may also be used. Thus, the nucleic acid may encode for one or more of a Δ15-desaturase, a Δ6-desaturase, a Δ5-desaturase, a Δ4-desaturase, a Δ6-desaturase, a Δ5-elongase, Δ6-elongase or combinations thereof.

In one embodiment, the nucleic acid encodes a Δ6-desaturase. In the context of the present invention, a Δ6-desaturase catalyzes the conversion of ALA to SDA and also LA to GLA. Δ6-Desaturases are described in WO 93/06712, U.S. Pat. Nos. 5,614,393, 5,614,393, WO 96/21022, WO 02/1557 and WO 99/27111 and their application to production in transgenic organisms is also described, e.g. in WO 98/46763, WO 98/46764 and WO 98/46765. In one embodiment, the Δ6-desaturase used in the present invention is derived or isolated from *Ostreococcus*, preferably OtD6 from *Ostreococcus tauri* (Domergue et al (2005), AY746357). In one embodiment, the nucleic acid comprises SEQ ID No. 3 or 5 and encodes a 6Δ-desaturase comprising or consisting of SEQ ID No. 4 or 6, a functional variant thereof or a polypeptide that encodes for a 6Δ-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to SEQ ID No. 4 or 6.

In another embodiment, the Δ6-desaturase is from the microalgae *Ostreococcus* RCC 809. Preferably, the nucleic acid comprises SEQ ID No. 7 or 9 and encodes a 6Δ-desaturase from the microalgae *Ostreococcus* RCC 809 comprising or consisting of SEQ ID No. 8 or 10, a functional variant thereof or a sequence that encodes for a 6Δ-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to SEQ ID No. 8 or 10.

In another embodiment, the nucleic acid encodes for a Δ4-desaturase. According to the various aspects of the invention, a Δ4-desaturase may be derived or isolated from *E. huxleyi*. Thus, in one embodiment, the nucleic acid comprises SEQ ID No. 11 encoding a Δ4-desaturase comprising or consisting of SEQ ID No. 12, a functional variant thereof or a Δ4-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to SEQ ID No. 12.

In another embodiment, the Δ4-desaturase is derived or isolated from *T. pseudonana*. Thus, in one embodiment, the nucleic acid comprises SEQ ID No. 13 encoding a Δ4-desaturase comprising or consisting of SEQ ID No. 14, a functional variant thereof or a Δ4-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to SEQ ID No. 14.

In another embodiment, the Δ4-desaturase is derived or isolated from *Ostreococcus* RCC809. In one embodiment, the nucleic acid comprises SEQ ID No. 15 or 17 encoding a Δ4-desaturase comprising or consisting of SEQ ID No. 16 or 18, a functional variant thereof or a Δ4-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to SEQ ID No. 16 or 18.

In another embodiment, a Δ6-elongase is from *Fragilariopsis cylindrus*. In one embodiment, the nucleic acid comprises SEQ ID No 19 encoding a Δ6-elongase comprising or consisting of SEQ ID No. 20, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to SEQ ID No. 20.

In another embodiment, a Δ5-desaturase is from *Fragilariopsis cylindrus*. In one embodiment, the nucleic acid comprises SEQ ID No 21 encoding a Δ5-desaturase comprising or consisting of SEQ ID No. 22, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology to SEQ ID No. 22.

In another aspect, the transgenic microalgae of the invention expresses a heterologous nucleic acid encoding a Δ6-desaturase, a Δ5-desaturase, a Δ4-desaturase, Δ6-elongase or combinations thereof. These enzymes are defined herein.

In one aspect, a transgenic microalgae of the invention expresses a heterologous nucleic acid encoding a Δ6-desaturase. Thus, in another aspect, the invention also relates to transgenic microalgae expressing a heterologous nucleic acid encoding a Δ6-desaturase. For example, the transgenic microalgae expresses a nucleic acid encoding a Δ6-desaturase, but does not express any other transgene involved in the regulation of the LC-PUFAs biosynthetic pathway. In other embodiments, the transgenic microalgae expresses a Δ6-desaturase and additional transgenes involved in the regulation of the LC-PUFAs biosynthetic pathway, for example a Δ5-elongase such as OtElo5 as shown in the examples.

In one embodiment, the microalgae is *P. triconutum*. In one embodiment, the nucleic acid comprising or consisting of SEQ ID No. 3 or 5 encodes a Δ6-desaturase or a sequence that encodes for a Δ6-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 4 or 6. In a preferred embodiment, the microalgae is *P. triconutum* and the nucleic acid encodes a Δ6-desaturase comprising or consisting of SEQ ID No. 4 or 6.

The transgenic microalgae expressing a nucleic acid encoding a Δ6-desaturase is characterised in that the total fatty acids content, specifically the omega 3 LC-PUFA content, is altered compared to a control microalgae. In particular, the omega-3 LC-PUFA content is increased by at least 2%, 3%, 4%, 5%, 6%, 7%, 8%, 9%, 10%, 11%, 12%, 13%, 14%, 15% or more. Specifically, the EPA content is increased by at least 2%, 3%, 4%, 5%, 6%, 7%, 8%, 9%, 10%, 11%, 12%, 13%, 14%, 15% compared to a control microalgae. Preferably, the total EPA content is at least 20% of the total LC-PUFAs content (mol %). Moreover, the DHA content in the transgenic algae is also increased by at least 0.5%.

In one embodiment, the various aspects of the invention exclude embodiments that relate to the production of biofuels.

In another aspect, the invention relates to a method for producing transgenic microalgae with increased omega-3 LC-PUFA content comprising introducing and expressing in a microalgae a heterologous nucleic acid which encodes for a polypeptide involved in the LC-PUFAs biosynthetic pathway. The omega-3 fatty acid may be selected from ALA, SDA, ETA, EPA, DPA or DHA. In one embodiment, the omega-3 LC-PUFAs is DHA. In another embodiment, the omega-3 fatty acid is EPA. The nucleic acid may encode Δ6-desaturase, Δ5-desaturase, Δ4-desaturase, Δ5-elongase, Δ6-elongase or combinations thereof.

In one embodiment, the method relates to producing transgenic microalgae with increased DHA levels said method comprising transforming a microalgae with a heterologous nucleic acid encoding a Δ5-elongase. According to this embodiment, the method may further comprise transforming said microalgae with one or more additional heterologous nucleic acid that regulates the production of omega-3 fatty acids, for example transforming with a nucleic acid encoding a Δ6-desaturase. In another embodiment, no additional nucleic acid that regulates the production of omega-3 fatty acids is introduced into said microalgae and expressed as heterologous nucleic acids.

In another embodiment, the invention relates to a method for producing transgenic microalgae with increased EPA levels said method comprising transforming a microalgae with a nucleic acid encoding a Δ6-desaturase. According to this embodiment, the method may further comprise transforming said microalgae with one or more additional nucleic acid that regulates the production of omega-3 LC-PUFAs. In another embodiment, no additional nucleic acid that regulates the production of omega-3 fatty acids is introduced into said microalgae.

In one embodiment, the method comprises transforming said microalgae with one or more additional nucleic acid that does not regulates the production of omega-3 LC-PUFAs, for example a glucose transporter gene.

Microalgae obtained or obtainable by those methods are also within the scope of the invention.

In another aspect, the invention relates to a method for increasing production of one of more omega-3 LC-PUFA in microalgae comprising
a) cultivating a transgenic microalgae described herein and
b) obtaining said one of more omega-3 LC-PUFA from the transgenic microalgae.

Specifically, the invention relates to a method for increasing the production of one or more omega-3 LC-PUFAs in microalgae comprising:
a) introducing and expressing in a microalgae a heterologous nucleic acid which encodes for a polypeptide involved in the LC-PUFAs biosynthetic pathway,
b) cultivating a transgenic microalgae expressing said heterologous nucleic acid and
c) obtaining one or more omega-3 fatty acid from the transgenic microalgae.

The transgenic microalgae is as described herein and is cultivated under conditions which allow for the production of one or more omega-3 LC-PUFAs. The nucleic acid may encode a Δ15-desaturase, a Δ6-desaturase, a Δ5-desaturase, a Δ4-desaturase, a Δ12-desaturase, Δ5-elongase, Δ6-elongase or combinations thereof as described herein.

In one embodiment, the method relates to increasing DHA production in microalgae comprising
a) introducing and expressing in a microalgae a heterologous nucleic acid encoding a Δ5-elongase,
b) cultivating a transgenic microalgae expressing said heterologous nucleic acid and
c) obtaining DHA from the transgenic microalgae.

The microalgae as described herein. The Δ5-elongase is as described herein. In one embodiment, the microalgae does not include and express a second heterologous nucleic acid encoding an enzyme involved in the regulation of the synthesis of omega-3 LC-PUFAs. In another embodiment, the microalgae includes and expresses a second heterologous nucleic acid encoding a polypeptide involved in the regulation of the synthesis of omega-3 LC-PUFAs. In another embodiment, the microalgae includes and expresses a second heterologous nucleic acid encoding a polypeptide not involved in the regulation of the synthesis of omega-3 LC-PUFAs, for example a glucose transporter. The transgenic microalgae is cultivated under conditions which allow for the production of DHA.

In one embodiment, the method relates to increasing DHA production in microalgae comprising
a) introducing and expressing in *P. triconutum* a heterologous nucleic acid encoding a Δ5-elongase,
b) cultivating *P. triconutum* expressing said heterologous nucleic acid and
c) obtaining said DHA from *P. triconutum*.

The microalgae as described herein. The Δ5-elongase is as described herein. In one embodiment, the microalgae does not include and express a second heterologous nucleic acid encoding an enzyme involved in the regulation of the synthesis of omega-3 LC-PUFAs. In another embodiment, the microalgae includes and expresses a second heterologous nucleic acid encoding an enzyme involved in the regulation of the synthesis of omega-3 LC-PUFAs. In another embodiment, the microalgae includes and expresses a second heterologous nucleic acid encoding a polypeptide not involved in the regulation of the synthesis of omega-3 LC-PUFAs, for example a glucose transporter.

*P. triconutum* is cultivated under conditions which allow for the production of DHA. These conditions will be apparent to the skilled person. For example, preferred culture conditions for *P. triconutum* are about 20° C. under constant illumination in about 60-80 µmol photons $m^{-2}$ $s^{-1}$. In one embodiment, the method comprises transforming said microalgae with one or more additional nucleic acid that does not regulates the production of omega-3 LC-PUFAs, for example a glucose transporter gene and supplying an exogenous carbon source. The algae can be grown in the dark.

In another embodiment, the method relates to increasing EPA in microalgae comprising:
a) introducing and expressing in a microalgae a heterologous nucleic acid encoding a 6Δ-desaturase,
b) cultivating the transgenic microalgae and
c) obtaining said EPA from the transgenic microalgae.

The microalgae as described herein The 6Δ-desaturase is as described herein. The microalgaeis cultivated under conditions which allow for the production of EPA.

In one embodiment, the method relates to increasing EPA production in microalgae comprising
a) introducing and expressing in *P. triconutum* a heterologous nucleic acid encoding a 6Δ-desaturase,
b) cultivating *P. triconutum* and
c) obtaining said EPA from *P. triconutum*.

The microalgae as described herein The Δ6-desaturase is as described herein. *P. triconutum* is cultivated under conditions which allow for the production of EPA.

These conditions will be apparent to the skilled person. For example, preferred culture conditions for *P. triconutum* are about 20° C. under constant illumination in about 0-80 µmol photons $m^{-2}$ $s^{-1}$ or preferably about 18° C. under constant illumination in about 25 µmol photons $m^{-2}$ $s^{-1}$. In one embodiment, the method comprises transforming said microalgae with one or more additional nucleic acid that does not regulates the production of omega-3 LC-PUFAs, for example a glucose transporter gene and supplying an exogenous carbon source. The algae can be grown in the dark.

In another aspect, the invention relates to a method for the manufacture of an oil, lipid or fatty acid composition comprising
a) cultivating a transgenic microalgae as described herein under conditions which allow for the production one or more omega-3 LC-PUFAs and
b) obtaining said one or more omega-3 LC-PUFAs from the transgenic microalgae.

In preferred embodiment, the omega-3 LC-PUFAs is DHA or EPA.

In another aspect, the invention relates to an omega-3 LC-PUFAs or oil isolated from a transgenic microalgae as described herein.

The fatty acids produced by the processes of the present invention can be isolated from the microalgae in the form of an oil, a lipid or a free fatty acid. One embodiment of the invention is therefore oils, lipids or fatty acids or fractions thereof which have been produced by the methods of the invention, especially preferably oil, lipid or a fatty acid composition comprising EPA or DHA and being derived from the transgenic microalgae.

The term "oil", or "lipid" is understood as meaning a fatty acid mixture comprising unsaturated, preferably esterified, fatty acid(s). The oil or lipid is preferably high in omega-3 polyunsaturated or, advantageously, esterfied fatty acid(s). In a particularly preferred embodiment the oil or lipid has a high ALA, ETA, EPA, DPA and/or DHA content, preferably a high EPA and/or DHA content.

For the analysis, the fatty acid content can, for example, be determined by gas chromatography after converting the fatty acids into the methyl esters by transesterification of the lipids such as triacylglycerides and/or phospholipids.

The omega-3 polyunsaturated acids produced in the method of the present invention, for example EPA and DHA, may be in the form of fatty acid derivatives, for example sphingolipids, phosphoglycerides, lipids, glycolipids, phospholipids, monoacylglycerol, diacylglycerol, triacylglycerol or other fatty acid esters.

The omega-3 and other polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example $H_2SO_4$. The fatty acids can also be liberated directly without the above-described processing step.

If further purification is necessary, standard methods can be employed. Such methods may include extraction, treatment with urea, fractional cyrstallization, HPLC, fractional distillation, silica gel chromatography, high-speed centrifugation or distillation, or combinations of these techniques. Protection of reactive groups, such as the acid or alkenyl groups, may be done at any step through known techniques (e.g. alkylation, iodination, use of butylated hydroxytoluene (BHT). Methods used include methylation of the fatty acids to produce methy esters. Similarly, protecting groups may be removed at any step. Desirably, purification of fractions containing, for example, ALA, STA, ETA, EPA, DPA and DHA may be accomplished by treatment with urea and/or fractional distillation.

Large scale purification methods of fatty acids from algae are known in the art. For example, a microalgae strain is cultivated to increase cell density using photobioreactors, open ponds, race ways or hybrid systems. Algal cells are separated from culture media by filtration, flocculation or centrifugation, followed by drying to improve extraction. Lipid extraction is then commonly performed using a non-water miscible organic solvent. Larger scale extraction is typically carried out with hexane as a solvent. Subsequently, unsaturated fatty acids are separated from the total lipids by fractional (molecular) distillation or winterization, whereby oil temperature is reduced to precipitate the more saturated lipids. Further processing to improve the quality, shelf-life and quantity of PUFA oil can include filtration, bleaching, deodorization, polishing and antioxidant addition. These methods are all known to a person skilled in the art.

In another aspect, the invention also relates to the use of the transgenic organism, preferably microalgae, as described herein in the production of fatty acids, preferably a omega-3 fatty acids. The invention encompasses the use of a transgenic organism, preferably microalgae, as described herein or of the oil, lipid, the fatty acids obtained from a transgenic organism, preferably microalgae, as described herein in feedstuffs, foodstuffs, cosmetics, nutriceutical or pharmaceuticals. The invention encompasses the use of a transgenic organism, preferably microalgae as described herein, in producing feedstuffs, foodstuffs, cosmetics, nutriceutical or pharmaceuticals. In another aspect, the invention also relates to the use of the transgenic microalgae, as described herein as a feedstuff for animals, preferably fish.

In another aspect, the invention also relates to a composition comprising the transgenic microalgae as described herein or a fatty acid, preferably a omega-3 fatty acid, oil, or lipid obtained from said microalgae. In a preferred embodiment, the composition comprises the transgenic microalgae as described herein or a product obtained or obtainable therefrom, such as an oil. In one embodiment, the composition may be a pharmaceutical composition, a cosmetic, a foodstuff, including food supplements, or feedstuff for animals. In particular, the invention relates to a foodstuff comprising the transgenic microalgae as described herein or fatty acid, preferably a omega-3 fatty acid, oil, or lipid obtained from said algae. This can be in the form of a dietary supplement, including fish oils. The invention also relates to an animal feed, especially for aquaculture, comprising the transgenic microalgae as described herein or fatty acid, preferably a omega-3 fatty acid, oil, or lipid obtained from said algae.

In another aspect, the invention relates to a composition comprising the transgenic microalgae as described herein, a fatty acid, preferably a omega-3 fatty acid, oil, or lipid obtained from said microalgae for use in medicine. In particular, the composition may be used to lower both blood pressure and heart rate in hypertensive individuals reducing the risk of sudden death, reduce inflammation, and to reduce the long-term risk of atherosclerosis and ischemic heart disease. The composition may also be used to treat eczema or metabolic syndrome. Also, a DHA rich diet is associated with increased cognitive abilities and depression and has a positive effect on arthritis and type II diabetes (Horrocks et al, 1999). Thus, the invention also relates to a composition comprising the transgenic microalgae as described herein or fatty acid, preferably a omega-3 fatty acid, oil, or lipid obtained from said microalgae for use in the treatment or prevention of cardiovascular conditions, including atherosclerosis, thrombosis, high blood pressure, myocardial infarction and atherosclerosis, inflammatory conditions, depression, cognitive decline, arthritis, and type II diabetes. Also encompassed in the scope of the invention are methods of treating or preventing cardiovascular and inflammatory conditions, depression, cognitive decline, arthritis and type II diabetes administering a composition comprising a therapeutic amount of the transgenic microalgae as described herein, a fatty acid, preferably a omega-3 fatty acid, oil, or lipid obtained from said microalgae to a patient in need thereof. The invention also relates to the use of a composition comprising the transgenic microalgae as described herein in the manufacture of a medicament for treating cardiovascular conditions, including atherosclerosis, thrombosis, high blood pressure, myocardial infarction and atherosclerosis, inflammatory conditions, depression, cognitive decline, arthritis, and type II diabetes.

In preferred embodiments, the composition may comprise or be obtained from a transgenic microalgae expressing a nucleic acid encoding a Δ6-desaturase and/or a transgenic microalgae expressing a nucleic acid encoding a Δ5-elongase as described herein.

The inventors have shown that microalgae can be manipulated using recombinant methods to produce an increased amount of LC-PUFAs, in particular EPA and DHA using heterologous gene expression. The inventors have surprisingly demonstrated that heterologous expression of Δ5-elongase from *Ostreococcus tauri* alone results in increased accumulation of DHA in *P. tricornutum* with DHA levels in transgenic strains reaching up to 13% of total fatty acids. A skilled person would understand that the invention is not restricted to algae and can indeed be applied to any organism that makes EPA/DHA. Thus, the invention also relates to a transgenic organism with increased DHA levels expressing a heterologous Δ5-elongase, preferably a Δ5-elongase from *Ostreococcus tauri*. In one embodiment, no other transgenes are expressed in the transgenic organism. In another embodiment, further transgenes may be expressed as described herein. Furthermore, the invention also relates to methods for increasing the production of DHA in a transgenic organism. This is achieved by expressing a heterologous Δ5-elongase, preferably a Δ5-elongase from *Ostreococcus tauris* in said organism. Details of said methods are described herein.

The organism may be an animal, for example a mammal. In one embodiment, humans are specifically excluded. In another embodiment, the organism is a plant, for example a monocot or dicot plant, for example crop plant. Crop plants include but are not limited to maize, rice, wheat, oilseed rape/canola, sorghum, soybean, sunflower, alfalfa, potato, tomato, tobacco, grape, barley, pea, bean, field bean, lettuce, cotton, sugar cane, sugar beet, broccoli or other vegetable brassicas or poplar.

In another aspect, the invention relates to isolated nucleic acids encoding for novel forms of the desaturases and elongases which may be useful in the heterologous reconstitution of the omega-3 long chain polyunsaturated fatty acid biosynthetic pathway in algae and higher plants. Specifically, the invention relates to isolated nucleic acids encoding Δ6-desaturase (Ost809Δ6), Δ4-desaturase (Ost809Δ4) and Δ6-elongase (FcELO6) and their corresponding polypeptides.

In one embodiment, the invention relates to an isolated nucleic acids comprising SEQ ID No. 7 or 9 encoding Δ6-desaturase (Ost809Δ6) comprising or consisting of SEQ ID No. 8 or 10, a functional variant thereof or a Δ6-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 8 or 10. The sequence may also be codon optimised for expression the target organism.

In one embodiment, the invention relates to an isolated nucleic acid comprising SEQ ID No. 15 or 17 encoding a Δ4-desaturase (Ost809Δ4) comprising or consisting of SEQ ID No.16 or 18, a functional variant thereof or a Δ4-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 16 or 18. The sequence may also be codon optimised for expression the target organism.

In one embodiment, the invention relates to an isolated nucleic acid comprising SEQ ID No. 19 encoding Δ6-elongase (FcELO6) comprising or consisting of SEQ ID No. 20, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 20. The sequence may also be codon optimised for expression the target organism.

In one embodiment, the invention relates to an isolated nucleic acid comprising SEQ ID No. 21 encoding a Δ5-desaturase comprising or consisting of SEQ ID No. 22, a functional variant thereof or a Δ5-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 22. The sequence may also be codon optimised for expression the target organism.

The invention also relates to a vector comprising one or more of the isolated nucleic acids as specified above. The vector may further comprise a regulatory sequence.

The invention also relates to a transgenic microalgae with increased production of omega-3 LC-PUFAs wherein said microalgae expresses a nucleic acid comprises SEQ ID No. 7, 9, 15, 17, 19 or 21 or a sequence that encodes for a peptide that has at least 75%, at least 80%, at least 85%, at least 90%, at least 91%, at least 92%, at least 93%, at least 94%, at least 95%, at least 96%, at least 97%, at least 98%, at least 99% homology to SEQ ID No. 8, 10, 16, 18, 20 or 22. Compositions comprising the transgenic microalgae, oil or lipids isolated therefrom and uses of as described herein in medicine or the formulation of a medicament, methods of treatment or feedstuff, foodstuff, pharmaceuticals or nutriceutical are also within the scope of the invention.

Without wishing to be bound by theory, the inventors believe that the activities of these nucleotides will prove useful in the heterologous reconstitution of the omega-3 long chain polyunsaturated fatty acid biosynthetic pathway in algae and plants. For example, the superior substrate-preference of the Ost809Δ6 enzyme distinguishes it from other *Ostreococcus* D6-desaturases, and can be used to maximise the flux of substrate through the n-3 pathway. Similarly, the Ost809Δ4 activity will prove useful in the specific conversion of DPA to DHA in transgenic photosynthetic organisms, whilst the FcELO6 activity provides a means by which GLA can be elongated to 20:3n-6.

In another embodiment, the invention therefore relates to the use of an isolated nucleic acid selected from a nucleic acid comprising or consisting of SEQ ID No. 7 or 9 encoding Δ6-desaturase (Ost809Δ6) comprising or consisting of SEQ ID No. 8 or 10, a functional variant thereof or a Δ6-desaturase that has at least 50%, at least 55%, at least 60%, at least 65%, at least 70%, at least 75%, at least 80%, at least 85%, at least 90%, at least 95%, at least 96%, at least 97%, at least 98%, at least 99% homology to SEQ ID No. 8 or 10, a nucleic acid comprising or consisting of SEQ ID No.16 or 18, a functional variant thereof or a Δ4-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 16 or 18, a nucleic acid comprising or consisting of SEQ ID No. 19 encoding Δ6-elongase (FcELO6) comprising or consisting of SEQ ID No. 20, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 20 or a nucleic acid comprising or consisting of SEQ ID No. 21 encoding a Δ5-desaturase comprising or consisting of SEQ ID No. 22, a functional variant thereof or a Δ5-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 22 in the production of a transgenic organism with increased omega-3 fatty acid content. In particular, the invention relates to the use of isolated nucleic acids encoding a Δ6-desaturase (Ost809Δ6) to maximise the flux of substrate through the n-3 pathway and produce enhanced levels of EPA and/or DHA. In another embodiment, the invention relates to the use of an isolated nucleic acid encoding a Δ4-desaturase (Ost809Δ4) to convert DPA to DHA. In another embodiment, the invention relates to the use of an isolated nucleic acid encoding a Δ6-elongase to elongate GLA to 20:3.

In another embodiment, the invention relates to the use of an isolated nucleic acid selected from a nucleic acid comprising or consisting of SEQ ID No. 19 encoding Δ6-elongase (FcELO6) comprising or consisting of SEQ ID No. 20, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 20 or a nucleic acid comprising or consisting of SEQ ID No. 21 encoding Δ5-desaturase comprising or consisting of SEQ ID No. 22, a functional variant thereof or a Δ5-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 22 in increasing DHA content. As shown in the examples and FIG. 13, DHA is increased by at least 10%, for example 14-17%.

In another embodiment, the invention relates to a method for producing a transgenic organism with increased of omega-3 LC-PUFAs production, in particular DHA and/or EPA, comprising transforming an organism with an isolated nucleic acid comprising or consisting of SEQ ID No. 7 or 9 encoding Δ6-desaturase (Ost809Δ6) comprising or consisting of SEQ ID No. 8 or 10, a functional variant thereof or a Δ6-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 8 or 10, a nucleic acid comprising or consisting of SEQ ID No.16 or 18, a functional variant thereof or a Δ4-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 16 or 18, a nucleic acid comprising or consisting of SEQ ID No. 19 encoding Δ6-elongase (FcELO6) comprising or consisting of SEQ ID No. 20, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 20 or a nucleic acid comprising or consisting of SEQ ID No. 21 encoding a Δ5-desaturase comprising or consisting of SEQ ID No. 22, a functional variant thereof or a Δ5-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 22.

In one embodiment, the invention relates to a method for producing a transgenic organism with increased of DHA production, comprising transforming an organism with an isolated nucleic acid nucleic acid selected from a nucleic acid comprising or consisting of SEQ ID No. 19 encoding Δ6-elongase (FcELO6) comprising or consisting of SEQ ID No. 20, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 20 or a nucleic acid comprising or consisting of SEQ ID No. 21 encoding a Δ5-desaturase comprising or consisting of SEQ ID No. 22, a functional variant thereof or a Δ5-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 22 in increasing DHA content. As shown in the examples and FIG. 13, DHA is increased by at least 10%, for example 14-17%.

In another embodiment, the invention relates to a method for increasing the production of omega-3 fatty acid transforming an organism with an isolated nucleic acid comprising or consisting of SEQ ID No. 7 or 9 encoding Δ6-desaturase (Ost809Δ6) comprising or consisting of SEQ ID No. 8 or 10, a functional variant thereof or a Δ6-desaturase that has at least 50%, at least 55%, at least 60%, at least 65%, at least 70%, at least 75%, at least 80%, at least 85%, at least 90%, at least 95%, at least 96%, at least 97%, at least 98%, at least 99% homology to SEQ ID No. 8 or 10, a nucleic acid comprising or consisting of SEQ ID No. 16 or 18, a functional variant thereof or a Δ4-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 16 or 18, a nucleic acid comprising or consisting of SEQ ID No. 19 encoding Δ6-elongase (FcELO6) comprising or consisting of SEQ ID No. 20, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 20 or a nucleic acid comprising or consisting of SEQ ID No. 21 encoding a Δ5-desaturase comprising or consisting of SEQ ID No. 22, a functional variant thereof or a Δ5-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 22.

In one embodiment, the invention relates to a method for increasing the production of omega-3 fatty acid transforming an organism with an isolated nucleic acid nucleic acid selected from a nucleic acid comprising or consisting of SEQ ID No. 19 encoding Δ6-elongase (FcELO6) comprising or consisting of SEQ ID No. 20, a functional variant thereof or a Δ6-elongase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 20 or a nucleic acid comprising or consisting of SEQ ID No. 21 encoding a Δ5-desaturase comprising or consisting of SEQ ID No. 22, a functional variant thereof or a Δ5-desaturase that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% homology to SEQ ID No. 22 in increasing DHA content. As shown in the examples and FIG. 13, DHA is increased by at least 10%, for example 14-17%.

In one embodiment of the methods, method may further comprise transforming said microalgae with one or more additional nucleic acid that regulates the production of omega-3 fatty acids. In another embodiment, no additional nucleic acid that regulates the production of omega-3 fatty acids are introduced into said microalgae. Other heterologous nucleic acids, for example encoding a glucose transporter may be included.

In another aspect, invention relates to a host cell transformed with a vector comprising one or more of the isolated nucleic acids defined herein, specifically an isolated nucleic acid comprising SEQ ID No. 1, 3, 5, 7, 9, 15, 17, 19 or 21. In one embodiment, the host cell is transformed with a vector comprising one of the isolated nucleic acids defined herein and no other heterologous transgenes involved in the regulation of the LC-PUFAs biosynthetic pathway are expressed in said organism.

The host cell may be an algae or a higher plant cell. For example, the host cell is a microalgae. In one embodiment, the host cell is a diatom. The host cell may also comprise one or more additional transgene. For example, the host cell may be a transgenic microalgae described herein expressing a nucleic acid encoding for a Δ5-elongase.

The transgenic organism according to the methods described above may a microalgae or a higher plant. Preferably, the transgenic organism according to the methods described is a microalgae. The term microalgae is defined elsewhere herein and includes a diatom. In one embodiment, the microalgae is P. tricornutum. The term higher plant includes monocot and dicot plants. In one embodiment, the plant is a crop plant as described herein.

All references cited in this disclosure are herewith incorporated by reference with respect to their entire disclosure content and the disclosure content specifically mentioned in this application.

"and/or" where used herein is to be taken as specific disclosure of each of the multiple specified features or components with or without the other at each combination unless otherwise dictated. For example "A, B and/or C" is to be taken as specific disclosure of each of (i) A, (ii) B, (iii) C, (iv) A and B, (v) B and C or (vi) A and B and C, just as if each is set out individually herein.

Unless context dictates otherwise, the descriptions and definitions of the features set out above are not limited to any particular aspect or embodiment of the invention and apply equally to all aspects and embodiments which are described.

The invention is further described in the following non-limiting examples.

EXAMPLES

Example 1

Generation of Transgenic Algae Over-expressing Δ6-Desaturases and Generation of Transgenic Algae Over-expressing Δ5-Elongase Materials and Methods
Strains and Growth Conditions P. tricornutum UTEX 646 was grown in ESAW medium (Harrison et al., 1980) at 18° C. and 20° C. with moderate shaking under white fluorescent lights in constant illumination (30 μmol and 60 μmol photons $m^{-2}$ $s^{-1}$). Analysis of the wild-type and transgenic algae have been performed during exponential and stationary growth phases.

Plasmid Design and Cloning

The coding sequences for Δ6-desaturase from Ostreococcus tauri, OtD6 (Domergue et al., 2005) and O.tauri Δ5-elongase OtElo5 (Meyer et al., 2004) were inserted as Kpn-Xba and EcoRV-SacI fragments, respectively, into pPha-T1 vector (Zaslayskaia et al., 2000), kindly provided by Dr. P. G. Kroth, (Universitat Konstanz, Germany). The coding region of OtD6 was used as a template to chemically synthesize (Genscript Corporation, N.J.) codon-optimized nucleotide sequence OtD6PT for expression in P. tricornutum. This codon-optimized Δ6-desaturase sequence was cloned into pPha-T1 vector, using EcoRV-SacI sites. The coding sequences for Δ6-desaturase from P. tricornutum, PtD6 (Domergue et al., 2002) was inserted as BamHI-XbaI fragment into pPha-T1 vector (Zaslayskaia et al., 2000).

Biolistic Transformation

Biolistic transformation of P. tricornutum was performed according to previously described (Zaslayskaia et al., 2000; Kroth 2007). Bombarded cells were transferred onto ESAW agar plates containing 75 μg/ml zeocin. The zeocin plates were placed in 24 h light under fluorescent lights (50 μmol $m^{-2}$ $s^{-1}$) and incubated at 20° C. for 3 weeks. Selected zeocin-resistant colonies were transferred to fresh zeocin plates and 2 ml ESAW+ zeocin cultures before being transferred to liquid medium minus antibiotic for lipid analysis.

Fatty Acid Analysis

Algae or yeast cells were harvested by centrifugation. Fatty acids were extracted and methylated as described (Garces and Mancha, 1993) with minor modifications. A 15 ml aliquot of algal culture was harvested; following methylation the heptane fraction was concentrated and re-suspended in 40 μl solvent prior to injection of 1 μl on to the GC column. Methyl ester derivatives of total fatty acids extracted were analysed by GC using an Agilent DB-225 column and identified using known standards.

Acyl-CoA Profiling

Algal cells were harvested by centrifugation, frozen in liquid nitrogen and extracted after Larson and Graham (2001), for reverse-phase LC with either quantitative analysis of fluorescent acyl-etheno-CoA derivatives or with electrospray ionization tandem mass spectrometry (multi reaction monitoring) in positive on mode For the analysis of etheno-CoA derivatives HPLC (Agilent 1200 LC system; Phenomenex LUNA 150·2 mm C18(2) column) was performed using the methodology and gradient conditions described previously (Larson and Graham 2001); whilst LC-MS/MS +MRM analysis followed the methods described by Haynes et al. 2008 (Agilent 1200 LC system; Gemini C18 column, 2 mm inner diameter, 150 mm with 5 mm particles). For the purpose of identification and calibration, standard acyl-CoA esters with acyl chain lengths from C14 to C20 were purchased from Sigma as free acids or lithium salts.

Lipid Profiling

The molecular species of TAGs and PLs were analysed by electrospray ionisation triple quadrupole mass spectrometry (API 4000 QTRAP; Applied Biosystems). The molecular species of polar lipid were defined by the presence of a head-group fragment and the mass/charge of the intact lipid ion formed by ESI (Welti et al., 2002; Devaiah et al., 2006 with modifications described by Xiao et al. 2010). Such tandem ESI-MS/MS precursor and product ion scanning, based on head group fragment, do not determine the individual fatty acyl species. Instead, polar lipids are identified at the level of class, total acyl carbons, and total number of acyl carbon-carbon double bonds. Polar lipids were quantified in comparison with a series of polar lipid internal standards. Triacylglycerols (TAGs) measured after Krank et al. (2007) were defined by the presence of one acyl fragment and the mass/charge of the ion formed from the intact lipid (neutral loss profiling). This allows identification of one TAG acyl species and the total acyl carbons and total number of acyl double bonds in the other two chains. The procedure does not allow identification of the other two fatty acids individually nor the positions (sn-1, sn-2, or sn-3) that individual acyl chains occupy on the glycerol. TAGs were quantified in a manner similar to the polar lipids, including background subtraction, smoothing, integration, isotope deconvolution and comparison of sample peaks with those of the internal standard (using LipidView, Applied Biosystems). However, whereas polar lipids within a class exhibit similar mass spectral response factors, the mass spectral responses of various TAG species are variable, owing to differential ionization of individual molecular TAG species. In the data shown herein, no response corrections were applied to the data. The data were normalized to the internal standards tri15:0 and tri19:0

Results

Generation of Transgenic Algae Over-expressing Δ6-Desaturases.

The native coding OtD6 and codon-optimized for expression in *P. tricornutum* nucleotide sequences for *O. tauri* Δ6-desaturase were cloned into pPha-T1 vector, generating expression cassettes OtD6N and OtD6Pt respectively, and the resulted constructs were used to transform *P. tricornutum*.

Expression of OtD6N Construct 13 zeocin resistant colonies were obtained by transformation with OtD6N and selected for further screening. Selected colonies were transferred into liquid medium and several positive transformants containing OtD6N were identified. We have studied the effects of temperature and light on the production of EPA and total fatty acids in Wt and transgenic *P. tricornutum*. Cultures were grown at different temperatures (18° C. and 20° C.) under constant illumination in different light intensity (25 μmol and 60 μmol photons $m^{-2}$ $s^{-1}$). GC-MS analyses have been performed during the exponential (E) and stationary (S) phases of cell growth. Fatty acid profiling of WT and mutants showed that palmitoleic acid (16:1Δ$^9$), EPA (20:5 n31 3), palmitic acid (16:0) and myristic acid (14:0) were the major FAs detected in algal cells grown in both stages. Similarly to the results obtained by Tonon et al. (Tonon 2002) from the studies of *P. tricornutum* (CCAP 1052/1A) cell cultures grown at 18° C. with 240 μE $m^{-2}$ $s^{-1}$, there was decrease in the amount of EPA and DHA as the cells of *P. tricornutum* UTEXS 646 used in our study shifted from exponential to stationary phase. Fatty acid analysis revealed that in cells transformed with Otd6N and grown at 20° C. in light intensity 25 μmol and 60 μmol photons $m^{-2}$ $s^{-1}$ EPA and DHA decreased upon transition to stationary phase. However, the levels of EPA and DHA in Otd6N cells grown at 20° C., 60 μE $m^{-2}$ $s^{-1}$ in stationary phase were higher than those of WT *P. tricornutum* (21.2% of EPA and 1.8% of DHA in Otd6N compared to 18.5% of EPA and 1.3% of DHA in WT (Table III, FIG. 1). In contrast, we found that in transgenic Otd6N cells grown at 18° C., 25 μE $m^{-2}$ $s^{-1}$ levels of EPA and DHA increased in stationary phase compared to exponential phase and are significantly higher than in WT samples (30.2% of EPA and 1.8% of DHA in Otd6N compared to 16.5% of EPA and 0.9% of DHA in WT). Fatty acids profiles from Wt and Otd6N transgenic *P. tricornutum* showed no differences in Δ6-unsaturated fatty acids (GLA and SDA) composition, which were barely present.

Expression of OtD6PT Construct 4 zeocin resistant colonies obtained by transformation with OtD6PT were selected to inoculate cultures for further screening and GC-MS analysis. The same trend towards decreasing levels of EPA and DHA in the stationary phase was observed for transgenic Otd6Pt cells grown at different light intensity and temperatures (Table III, FIG. 1). Recombinant cells expressed higher levels of EPA (20.8% in the stationary phase at 20° C., 60 μE $m^{-2}$ $s^{-1}$ and 22.2% at 18° C., 25 μE $m^{-2}$ $s^{-1}$ compared to 18.5% and 16.8% in WT respectively). In addition to detection of higher levels of EPA we also observed an increase in DHA levels with minor variation between the two phases of growth (Table III, FIG. 1).

Generation of Transgenic Algae Over-expressing OtElo5

Figure 2A:
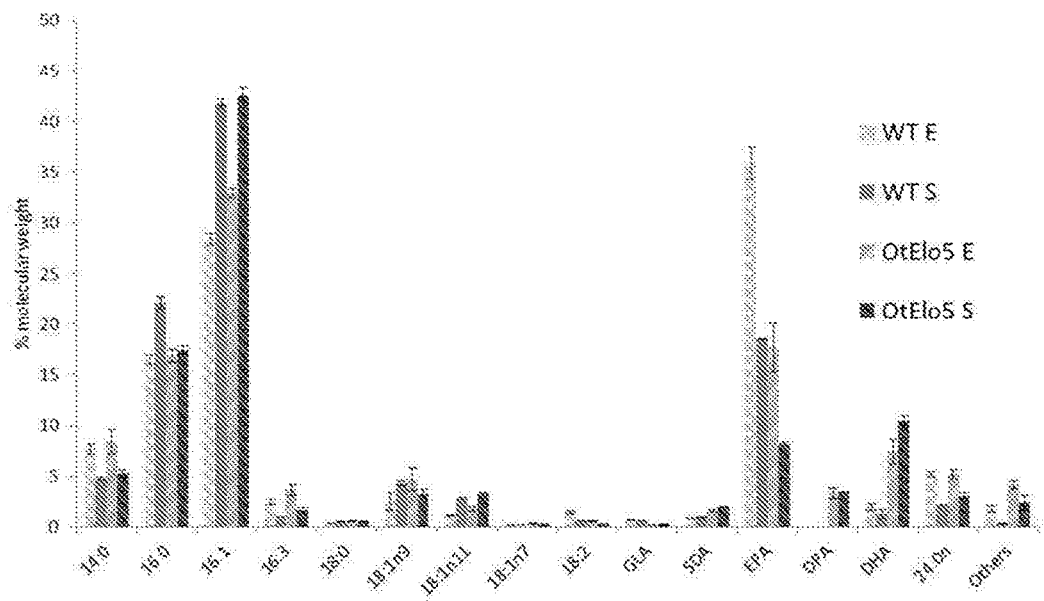
FIG. 2: Total fatty acid composition of WT and transgenic *P. tricornutum* cells expressing OtElo5 during the exponential (E) and stationary (S) phases. Cultures were grown at 20° C. under constant illumination 60 µmol photons $m^{-2}s^{-1}$ with agitation (FIG. 2a). Each value represents the mean±SD of 3 separate experiments. EPA, DPA and DHA content in WT and transgenic *P. tricornutum* expressing OtElO5 (FIG. 2b). Cultures were grown at 20° C. 60 µmol $m^{-2}s^{-1}$ under constant agitation at 70 rpm. Each measurement is the average of 3 biological replicates.
Figure 2B:
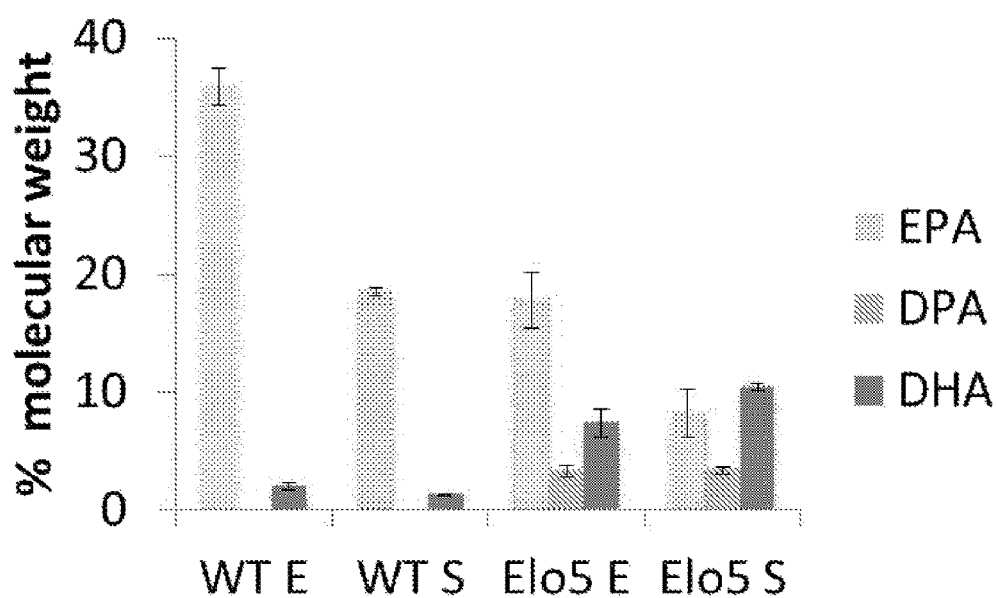

3 zeocin resistant clones obtained by transformation with OtElo5 were identified in an initial screen and used to inoculate cultures for further screening and GC-MS analysis. Cultures were grown at 20° C. under constant illumination in 60 μmol photons $m^{-2}$ $s^{-1}$. FAMEs analysis of *P. tricornutum* transformed with OtElo5 have been performed during the exponential (E) and stationary (S) phases of cell growth and revealed the presence of DPA in the range of 2.8-4.7% in transgenic clones which was not detected in WT cells (Table IV, FIG. 2a). Levels of EPA in transformed clones were decreased to an average of 17.7% compared to 35.9% in WT in the exponential phase of growth and to 8.2% in clones over-expressing the Elo5 gene compared to 18.5% in WT during the stationary phase of growth. A substantial increase in DHA was observed in all 3 transgenic clones averaging 7.4% in exponential phase and 10.4% in stationary phase compared to 2.0% and 1.3% respectively in WT. DHA accumulation has been increased upon transition to stationary phase.

Determination of Acyl-CoA Pool Composition

Figure 3A:
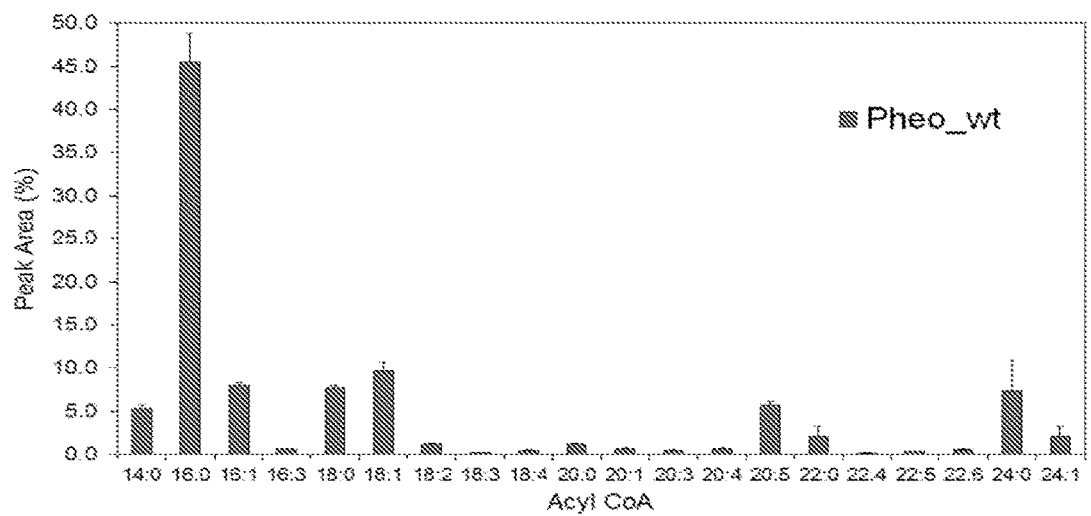
FIG. 3: The acyl-CoA profiles of WT (FIG. 3a) and transgenic (FIG. 3b) *P. tricornutum* expressing the *Ostreococcus* Elo5. The accumulation of LC-PUFA acyl-CoAs in B is boxed with a dotted line. The internal standard (istd) is 17:00 acyl-CoA.
Figure 3B:
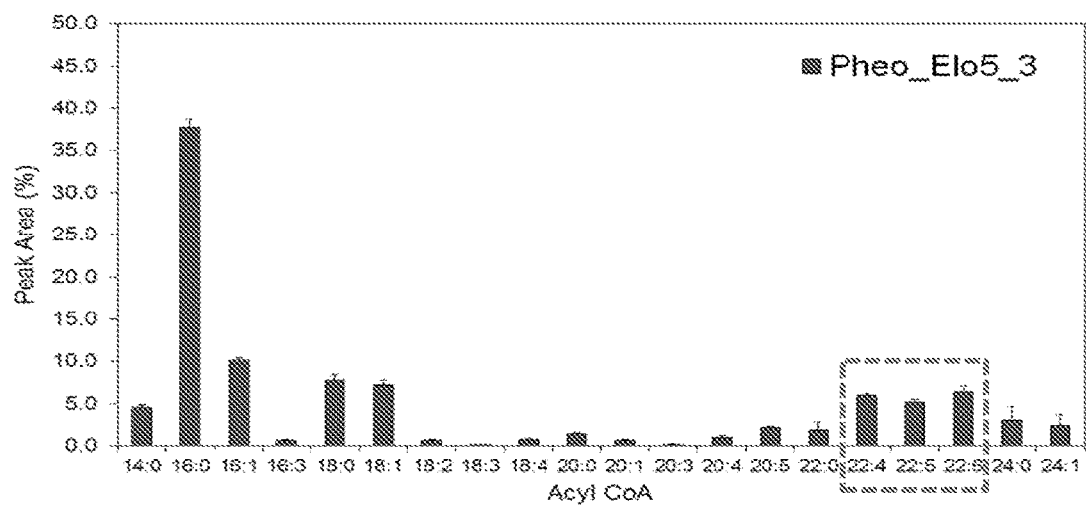
Figure 4A:
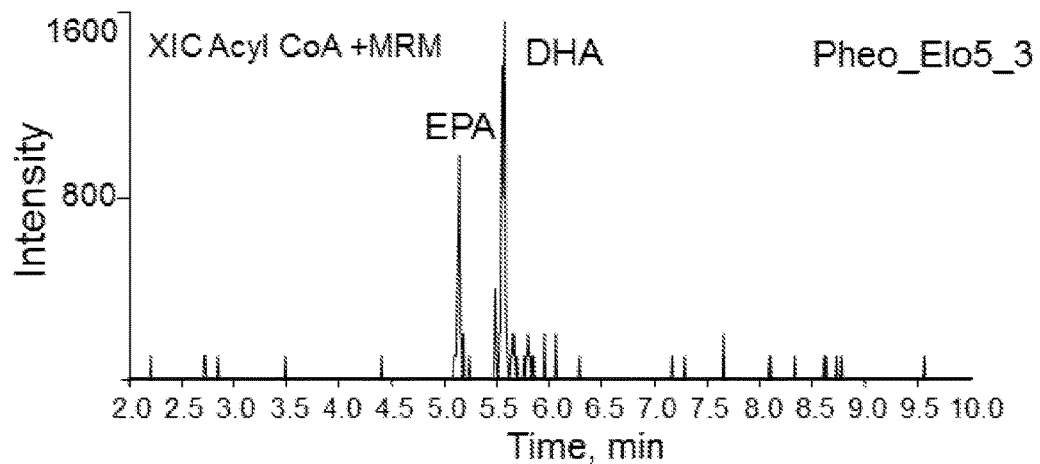
FIG. 4: EPA and DHA content in the total FA extracts of WT and transgenic OtElo5 *P. tricornutum* cells (FIG. 4a) and in exponential, late exponential and stationary phases (FIG. 4b).
Figure 4B:
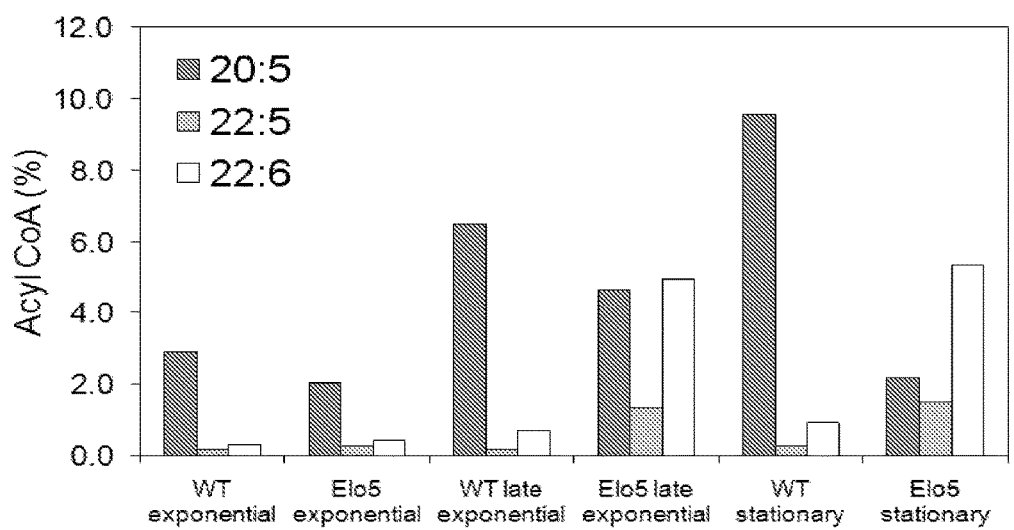

To better understand the processes of acyl desaturation in diatoms the composition of the acyl-CoA pool was determined for the wild-type (WT) and transgenic *P. tricornutum*, expressing OtElo5-elongase (FIG. 3). The study of acyl-CoA profile of WT *P. tricornutum* in the stationary phase of growth revealed that palmitic, palmitoleic, stearic, oleic and EPA-CoA were the most abundant, thus demonstrating the direct relationship between the levels of native fatty acids in the acyl-CoA pool vs the total fatty acids. EPA-CoA represented 5.7% of the acyl-CoA pool, indicating that this level of EPA-CoA could potentially act as an intermediate in the synthesis of DHA through elongation to 22:5n-3 and desaturation to 22:6n-3. Only traces (<1.0) of 22:4 n-6, 22:5 n-3 (DPA) and DHA were detected in the CoA pool of WT *P. tricornutum*. As can be seen in FIG. 3, similar analysis of transgenic *P. tricornutum* demonstrated a significant increase in the levels of 22:4 n-6, 22:5 n-3 (EPA) and DHA accompanying by the decrease in EPA levels. As shown in FIG. 4, detailed analysis of the composition of the acyl-CoA pool through different stages of cell growth revealed that EPA and DHA were accumulating progressively from exponential to stationary phase displaying maximum levels of 5.2% and 6.3% in stationary phase.

Profiling of TAG Molecular Species

In this study we identified and compared the molecular species of TAGs formed by WT and OtElo5 transgenic *P. tricornutum* and investigated changes in TAG synthesis in response to transition from exponential to stationary phase. Cultures were grown at 20° C. under constant illumination in 60 µmol photons m$^{-2}$ s$^{-1}$ and analysed using ESI-MS. The mass spectrum obtained from direct infusion ESI-MS of algal lipid extracts shows that a majority of the molecular ions are observed between 750 and 950 mass/charge (m/z). We detected 26 individual TAG species in WT *P. tricornutum*. The oil extracts of WT were predominantly composed of TAGs 46:1, 46:2 48:1, 48:2, and 48:3 and 50:3, having palmitic (16:0), palmitoleic (16:1), and myristic (14:0) acid substituents. TAG 48:1 (16:0/16:0/16:1) and 48:2 (16:0/16: 1/16:1) constitute the main TAG molecular species that is expressed throughout the time course analysis of *P. tricornutum* cells (FIGS. 5a and 5B). An increase in the diversity of TAG molecular species (with as much as 29 individual TAGs) was detected from cells expressing OtElo5-elongase. Specifically, new TAG species, 54:8, 54:9 and 56:8 were observed and transgenic cells show significantly higher levels of 54:7. DHA was incorporated in TAGs 52:7, 54:7, 54:8, 54:9 and 56:8. The time course (FIG. 6) also revealed that TAGs 54:7 and 56:8 appear to have more DHA incorporated into TAGs as the cells shift from the exponential growth phase to the stationary phase. TAGs molecular species 52:7, 54:8 and 54:9 demonstrated more or less constant DHA proportions when cultures were shifted from exponential to stationary phase. Levels of TAGs containing DHA averaged 12.5% in exponential stage and 10.5% in the stationary phase.

TABLE III

Fatty acid composition (molar %) of WT and transgenic *P. tricornutum* expressing O. tauri Δ6 desaturase under different growth conditions at two growth stage, where E is the exponential and S is the stationary growth phases. Each measurement is the average of three biological replicates.

| Cell strain | | 20° C. 60 µmol photons | | 20° C. 25 µmol photons | | 18° C. 25 µmol photons | |
|---|---|---|---|---|---|---|---|
| | | E | S | E | S | E | S |
| Otd6N | 14:0 | 6.3 ± 1.1 | 5.6 ± 1.6 | 11.5 ± 0.7 | 7.6 ± 1.5 | 13.0 ± 1.1 | 10.9 ± 1.0 |
| | 16:0 | 16.0 ± 0.5 | 21.0 ± 1.3 | 12.8 ± 0.9 | 16.8 ± 1.6 | 15.3 ± 0.8 | 16.6 ± 1.1 |
| | 16:1 | 28.3 ± 1.7 | 36.5 ± 1.6 | 32.8 ± 0.2 | 30.3 ± 1.9 | 35.1 ± 2.1 | 34.4 ± 2.5 |
| | 16:3 | 2.5 ± 0.2 | 0.9 ± 0.2 | 4.0 ± 0.6 | 0.9 ± 0.1 | 3.6 ± 0.0 | 2.7 ± 0.2 |
| | 18:0 | 0.5 ± 0.0 | 0.7 ± 0.0 | 0.3 ± 0.0 | 0.4 ± 0.0 | ND | ND |
| | 18:1 | 6.2 ± 1.4 | 8.6 ± 1.5 | 18.1 ± 0.0 | 24.9 ± 0.3 | 2.1 ± 0.2 | 2.5 ± 0.2 |
| | 18:2 n-6 | 1.5 ± 0.1 | 0.6 ± 0.0 | ND | ND | 1.4 ± 0.2 | 1.4 ± 0.2 |
| | 18:3 n-6 | 0.7 ± 0.3 | 1.3 ± 0.3 | ND | ND | ND | ND |
| | 18:4 n-3 | 0.8 ± 0.1 | 0.8 ± 0.1 | ND | 0.4 ± 0.0 | 1.0 ± 0.4 | 1.0 ± 0.4 |
| | 20:5 n-3 | 32.2 ± 3.6 | 21.2 ± 1.9 | 20.6 ± 1.1 | 17.8 ± 2.6 | 27.1 ± 2.7 | 30.2 ± 3.2 |
| | 22:6 n-3 | 2.3 ± 0.2 | 1.8 ± 0.3 | 1.4 ± 0.1 | 1.0 ± 0.1 | 1.4 ± 0.4 | 1.8 ± 0.3 |
| | Others | 6.89 ± 0.6 | 4.3 ± 0.6 | 12.2 ± 1.8 | 6.0 ± 0.2 | 5.7 ± 0.4 | 6.2 ± 0.6 |
| Otd6Pt | 14:0 | 7.0 ± 1.4 | 4.9 ± 1.0 | 5.6 ± 0.2 | 4.9 ± 0.2 | 12.8 ± 0.1 | 7.4 ± 0.4 |
| | 16:0 | 16.3 ± 1.3 | 20.2 ± 1.5 | 9.5 ± 0.3 | 16.8 ± 0.7 | 17.0 ± 0.9 | 20.4 ± 0.2 |
| | 16:1 | 27.1 ± 4.0 | 38.6 ± 3.6 | 24.5 ± 0.2 | 33.4 ± 7.9 | 28.3 ± 1.2 | 35.8 ± 2.6 |
| | 16:3 | 2.5 ± 0.2 | 1.1 ± 0.3 | 4.0 ± 0.6 | 1.4 ± 0.1 | 2.9 ± 0.0 | 5.2 ± 1.1 |
| | 18:0 | 0.5 ± 0.1 | 0.6 ± 0.1 | 0.3 ± 0.0 | 0.4 ± 0.0 | ND | ND |
| | 18:1 | 7.8 ± 0.2 | 8.7 ± 0.4 | 26.9 ± 5.4 | 24.9 ± 0.3 | 6.0 ± 0.9 | 8.5 ± 0.9 |
| | 18:2 n-6 | 1.1 ± 0.2 | 1.1 ± 0.1 | ND | ND | 1.2 ± 0.0 | 1.2 ± 0.0 |
| | 18:3 n-6 | 1.2 ± 0.2 | 0.8 ± 0.0 | 0.2 ± 0.0 | 0.2 ± 0.0 | ND | ND |
| | 18:4 n-3 | 1.1 ± 0.1 | 1.2 ± 0.1 | 0.6 ± 0.1 | 0.6 ± 0.0 | 1.5 ± 0.0 | 1.5 ± 0.0 |
| | 20:5 n-3 | 33.2 ± 1.4 | 20.8 ± 3.5 | 27.0 ± 4.0 | 16.6 ± 2.0 | 25.8 ± 0.1 | 22.2 ± 1.3 |
| | 22:6 n-3 | 1.7 ± 0.3 | 1.5 ± 0.4 | 1.3 ± 0.1 | 1.2 ± 0.6 | 1.1 ± 0.0 | 1.3 ± 0.2 |
| | Others | 9.2 ± 0.6 | 4.3 ± 0.9 | 12.3 ± 1.8 | 5.5 ± 3.6 | 7.3 ± 0.3 | 3.1 ± 0.3 |
| WT | 14:0 | 7.7 ± 0.5 | 4.8 ± 0.1 | 5.1 ± 0.2 | 4.8 ± 0.5 | 10.9 ± 0.5 | 7.9 ± 0.1 |
| | 16:0 | 16.5 ± 0.4 | 22.2 ± 0.6 | 11.0 ± 2.0 | 16.6 ± 3.2 | 19.7 ± 0.4 | 21.1 ± 1.3 |
| | 16:1 | 28.4 ± 0.6 | 41.8 ± 0.5 | 22.3 ± 1.1 | 32.2 ± 4.1 | 35.8 ± 0.6 | 42.1 ± 2.5 |
| | 16:3 | 2.4 ± 0.3 | 1.0 ± 0.1 | 2.6 ± 0.6 | 0.6 ± 0.1 | 2.4 ± 0.3 | 1.4 ± 0.0 |
| | 18:0 | 0.4 ± 0.0 | 0.5 ± 0.0 | 0.3 ± 0.1 | 0.3 ± 0.1 | ND | ND |
| | 18:1 | 3.8 ± 0.8 | 7.3 ± 0.2 | 28.9 ± 1.4 | 25.7 ± 4.9 | 6.1 ± 0.3 | 8.2 ± 0.1 |
| | 18:2 n-6 | 1.4 ± 0.1 | 0.6 ± 0.0 | ND | ND | 1.1 ± 0.1 | 0.8 ± 0.1 |
| | 18:3 n-6 | 0.7 ± 0.0 | 0.6 ± 0.0 | ND | ND | ND | ND |
| | 18:4 n-3 | 0.8 ± 0.0 | 1.0 ± 0.0 | 0.6 ± 0.0 | 0.4 ± 0.1 | 1.0 ± 0.7 | 0.6 ± 0.8 |
| | 20:5 n-3 | 35.9 ± 1.6 | 18.5 ± 0.4 | 27.6 ± 2.3 | 17.1 ± 2.5 | 22.2 ± 0.7 | 16.8 ± 2.8 |
| | 22:6 n-3 | 2.0 ± 0.3 | 1.3 ± 0.0 | 1.8 ± 0.1 | 1.3 ± 0.3 | 0.8 ± 0.1 | 0.9 ± 0.2 |
| | Others | 6.8 ± 0.3 | 2.4 ± 0.3 | 10.0 ± 0.9 | 5.1 ± 0.8 | 4.9 ± 0.5 | 2.9 ± 0.3 |

TABLE IV

Fatty acid composition (molar %) of WT and transgenic *P. tricornutum* expressing Ot Elo5 during exponential (E) and stationary (S) phases. Cultures were grown at 20° C. 60 µmol m$^{-2}$s$^{-1}$ under constant agitation at 70 rpm. Each measurement is the average of 3 biological replicates.

| Fatty acids | WT E | WT S | OtElo5 E | OtElo5 S |
|---|---|---|---|---|
| 14:0 | 7.7 ± 0.5 | 4.8 ± 0.5 | 8.4 ± 1.2 | 5.3 ± 1.6 |
| 16:0 | 16.5 ± 0.5 | 22.1 ± 0.6 | 16.8 ± 0.6 | 17.4 ± 1.3 |
| 16:1 | 28.4 ± 0.6 | 41.8 ± 0.5 | 32.9 ± 0.4 | 42.5 ± 1.6 |
| 16:3 | 2.4 ± 0.3 | 1.0 ± 0.0 | 3.6 ± 0.6 | 1.7 ± 0.6 |
| 18:0 | 0.4 ± 0.0 | 0.5 ± 0.0 | 0.6 ± 0.0 | 0.5 ± 0.0 |
| 18:1 | 3.8 ± 0.8 | 7.3 ± 0.2 | 6.8 ± 1.1 | 6.8 ± 1.5 |
| 18:2 n-6 | 1.4 ± 0.1 | 0.6 ± 0.0 | 0.6 ± 0.0 | 0.3 ± 0.0 |
| 18:3 n-6 | 0.7 ± 0.0 | 0.6 ± 0.0 | 0.2 ± 0.0 | 0.2 ± 0.2 |
| 18:4 n-3 | 0.8 ± 0.0 | 1.0 ± 0.0 | 1.6 ± 0.0 | 2.0 ± 0.1 |
| 20:5 n-3 | 35.9 ± 1.6 | 18.5 ± 0.4 | 17.7 ± 2.4 | 8.2 ± 2.0 |
| 22:5 n-3 | ND | ND | 3.3 ± 0.5 | 3.4 ± 1.2 |
| 22:6 n-3 | 2.0 ± 0.3 | 1.3 ± 0.1 | 7.4 ± 1.2 | 10.4 ± 0.3 |
| 24:0 | 5.2 ± 0.2 | 2.1 ± 0.0 | 5.2 ± 0.4 | 3.1 ± 0.4 |
| Others | 1.8 ± 0.3 | 0.3 ± 0.3 | 4.1 ± 0.4 | 2.4 ± 0.6 |

Discussion

Many marine microbes produce high levels of EPA and DHA but only few species have the ability to partition these fatty acids into storage lipids in the form of triacylglycerols (TAGs). The majority of algal species accumulate saturated and mono-unsaturated fatty acids in TAGs (Harwood, 1998; Roessler, 1990b). Partitioning of LC-PUFAs into TAGs have been observed in *Parietochloris incise* (Bigogno et al., 2002), the freshwater red microalga *Porphyridium cruentum* (Cohen et al., 2000), and marine microalgae *Nannochloropsis oculata*, *Phaeodactylum tricornutum*, *Thalassiosira pseudonana* and *Pavlova lutheri*, (Tonon et al., 2002). Thus these species are good candidates for further studies, in order to understand the processes responsible for the incorporation of LC-PUFAs into storage oils in microalgae.

At present it is generally accepted that oleaginous algae produce small quantities of TAG under optimal growth conditions (Hu et al. 2008). Among major factors affecting triacylglycerol accumulation and fatty acid composition in microalgae are temperature and light intensity. Generally, it is considered that fatty acid unsaturation increases with temperature decrease and low light favours the formation of PUFAs. For example, in *P. tricornutum* UTEXS 640 optimal culture temperature for EPA production was 21.5 to 23° C. (Yongmanitchai W. and Ward O., 1991). A temperature shift strategy has been employed to enhance the overall n-3 PUFAs (including EPA) production because the optimal temperature for microalgal growth is often higher than that for n-3 PUFAs formation (Jiang and Chen, 2000). Such a phenomenon has been observed in many different algal species including *P. cruentum* (Springer et al., 1994), *Nannochloropsis* sp. (Sukenik, 1991) and *P. irregular* (Stinson et al., 1991). However, Ohta et al. (1993) observed that the optimal temperature for growth of *P. purpureum* also yields a biomass with the highest EPA content. These results suggest that the effect of temperature on cell growth and n-3 PUFA production should be carefully studied for individual microalgal species.

Profiling of TAG species in *P. tricornutum* has been previously reported (Yongmanitchai and Ward 1993; Yu et al., 2009). We observed the same predominant fatty acids (i.e., 14:0, 16:0, 16:1, 16:3, and 20:5) incorporated in TAGs as described in these earlier studies. Yongmanitchai and Ward 1993 identified only 18 TAG molecular species via reverse-phase HPLC analysis. Due to the high resolution and sensitivity of ESI-MS, Yu et al., 2009 were able to detect twofold more species in algal oil extracts (14 of the 18 species they detected by HPLC, at comparable percentage composition. However, TAGs 48:7, 48:9, 48:12, and 54:10 were not detected which could be explained by the difference in the *P. tricornutum* strains and culture conditions.

Example 2

Identification and Characterization of New Activities for PUFAs Biosynthesis in Algae and Plants 2.1 Identification of a Δ6-Desaturase from the Microalga *Ostreococcus* RCC809

Genome of green alga *Ostreococcus* RCC809 was analysed with BLAST using already known N-terminal cytochrome b5-fusion desaturases as query. This analysis revealed the presence of several genes coding for putative PUFA desaturases. The deduced open reading frames were used as templates to chemically synthesise (Genscript Corporation, N.J.) codon-optimised nucleotide sequences for expression in diatoms.

Functional Characterization of Putative *Ostreococcus* RCC809 Δ6-Desaturase in Yeast.

The codon-optimised open reading frame of the putative Δ6-desaturase (SEQ ID No.s 7 to 10, hereafter designated Ost809Δ6) was inserted as KpnI-SacI fragment behind the galactose—inducible GAL1 promoter of the yeast expression vector pYES2 (Invitrogen, N.J.). Ost809Δ6

The *S. cerevisiae* strain W303-1A was transformed with plasmid DNA using a lithium acetate method. Cultures were grown at 22° C. in the presence of 2% (v/v) raffinose for 48 h, and expression of the transgene was induced by addition of galactose to 2% in the presence of 0.5 mM of linoleic acid (LA, 18:2n-6) and 1% (w/v) tergitol NP-40 (Sigma) as described (Sayanova et al., 2001).

The predicted function of the candidate desaturase Ost809Δ6 (predicted to encode a C18 Δ6-desaturase of 461 amino acids) was investigated by expression studies in *S. cerevisiae* in the presence of a range of potential fatty acid substrates. Total fatty acid methyl esters from yeast cells were then analysed by GC-FID and the identity of novel peaks confirmed by GC-MS and co-migration with authentic standards. As shown in FIG. 8, expression of a synthetic ORF encoding Ost809Δ6, confirmed the enzymatic capability to convert exogenously supplied substrate (α-Linolenic acid, ALA; C18:Δ9,12,15) to the Δ6-desaturated product SDA (18:4, n-3). In the absence of galactose, the exogenous substrate ALA is not converted to SDA. Thus, on the basis of these results, Ost809Δ6 was confirmed as a D6-desaturase. The substrate selectivity of Ost809Δ6 was determined by exogenously supplying equal quantities of LA and ALA in the growth media. As it is shown in FIG. 9, Ost809Δ6 only recognised the n-3 fatty acid ALA as a substrate, whereas the n-6 substrate was not desaturated. This is distinct from a Δ6-desaturase identified from *Ostreococcus tauri* (Domergue et al, 2005), which showed activity towards both LA and ALA as substrates. Thus Ost809Δ6 is superior and distinct for the exclusive production of Δ6-desaturated n-3 fatty acids.

Yeast cultures were supplemented with different potential FA substrates (listed in Table V) but desaturation activity of O809d6 was detected only in the presence of ALA.

2.2 Identification of Putative Δ4-Desaturase from O809

The genome sequence of *Ostreococcus* RCC809 http://genome.jgi-psf.org/OstRCC809_2/

OstRCC809_2.home.html was searched with previously functionally characterised sequences of Δ4-desaturases and the presence of an apparent candidate (JGI protein ID #40461) for a Δ4-desaturase was detected. The deduced open reading frame was used as a template to chemically synthesise (Genscript Corporation, N.J.) codon-optimised nucleotide sequences for expression in diatom *P. tricornutum* (SEQ ID No.s 15 to 18).

Functional Characterization of Putative Δ4-Desaturase from 0809 in Yeast.

The codon-optimised for expression in *P. tricornutum* open reading frame of the putative Δ4-desaturase was inserted as KpnI-SacI fragment behind the galactose—inducible GAL1 promoter of the yeast expression vector pYES2 (Invitrogen, N.J.).

As can be seen in FIG. 10, galactose-dependent expression of the Ost809 protein 40461 resulted in the Δ 4-desaturation of DPA to DHA, confirming the function of this ORF as a C22 Δ 4-desaturase and on this basis we designated this gene as Ost809Δ4. Note that in the absence of the inducer (galactose), no DHA is detected, nor in the absence of the Ost809Δ4 ORF.

2.3 Identification of a Δ6-Elongase from *Fragilariopsis cylindrus*

The publically available genome sequence of the marine diatom *Fragilariopsis cylindrus* (http://genome.jgi-psf.org/Fracy1/Fracy1.home.html) was analysed with BLAST using already known Δ6-elongase sequences (such as the Δ6-elongase from *C. elegans*—Beaudoin et al, 2000) as query and a candidate open reading frame (designated Frag #177742) was used as a template to chemically synthesise (Genscript Corporation, N.J.) codon-optimised nucleotide sequence for expression in *T. pseudonana*.

Functional Characterization of Fc Δ6-Elongase in Transgenic Yeast

Heterologous expression of Frag #177742 in *S. cerevisiae* was carried out exactly as described above, with the codon-optimised ORF cloned into the yeast expression vector pYES2. Galactose-mediated induction of this construct was used to confirm that this ORF functioned as a Δ 6-elongase, specifically elongating C18 Δ 6-unsaturated substrates such as GLA to a C20 form. As can be seen in FIG. 11, elongation of GLA to 20:3 only occurs in the presence of galactose and the ORF Frag #177742. On the basis of these results, this was redesignated FcELO6.

TABLE V

List of Substrates Tested:

Ost809D6
18:2, ALA, GLA, 18:2& 18:3, 20:4n-6 (ARA), 20:2, ERA, ETA, 22:5n-6 (DPA)
FcElo6
18:2, GLA, GLA & SDA
Ost809Δ4
DPA (Substrates underlined are those which worked)

TABLE VI

Fatty acid composition of yeast cells expressing Ost809Δ6, FcElo6 or Ost809Δ4 and substrate specificities of each of these
Fatty Acid Composition (molar %)
Construct

| FA | O809Δ6 Gal− | O809Δ6 Gal+ | O809Δ6 Gal− | O809Δ6 Gal+ | FcElo6 Gal− | FcElo6 Gal+ | O809d4 Gal− | O809d4 Gal+ | pYes2 BPX72 | pYes2 HP1 |
|---|---|---|---|---|---|---|---|---|---|---|
| 16:0 | 26.2 | 26.0 | 24.8 | 22.4 | 25.2 | 23.2 | 22.8 | 20.4 | 26.1 | 22.2 |
| 16:1 | 25.6 | 28.8 | 26.3 | 27.9 | 23.7 | 26.3 | 49.2 | 51.0 | 29.2 | 51.5 |
| 18:0 | ND | ND | ND | ND | ND | ND | 4.2 | 4.4 | ND | 3.9 |
| 18:1 | 15.2 | 16.3 | 13.6 | 15.4 | ND | ND | 20.2 | 21.6 | 17.5 | 19.7 |
| 18:2 | 5.8 | 6.8 | ND | ND | ND | ND | ND | ND | ND | ND |
| GLA | ND | ND | ND | ND | 38.7 | 22.8 | ND | ND | ND | ND |
| ALA | 25.6 | 11.9 | 32.9 | 15.7 | ND | ND | ND | ND | 27.2 | ND |
| SDA | 1.6 | 10.3 | 2.3 | 18.5 | ND | ND | ND | ND | ND | ND |
| DHGLA | ND | ND | ND | ND | ND | 14.1 | ND | ND | ND | ND |
| DPA | ND | ND | ND | ND | ND | ND | 2.9 | 2.3 | ND | 2.7 |
| DHA | ND | ND | ND | ND | ND | ND | ND | 0.4 | ND | ND |

TABLE VII

| Substrate Specificity | | |
|---|---|---|
| Construct | Substrate | % |
| Ost809Δ6 | 18:2 | 0.0 |
| Ost809Δ6 | 18:3 ALA | 54.1 |
| FcElo6 | 18:3 GLA | 38.1 |
| Ost809Δ4 | 22:5 DPA | 13.5 |

On the basis of the identification of novel forms of the Δ 6-desaturase (Ost809Δ6), Δ 4-desaturase (Ost809Δ4) and the Δ 6-elongase (FcELO6), it is very likely that these activities will prove useful in the heterologous reconstitution of the omega-3 long chain polyunsaturated fatty acid biosynthetic pathway in algae and plants. For example, the superior substrate-preference of the Ost809Δ6 enzyme distinguishes it from other *Ostreococcus* Δ 6-desaturases, and can be used to maximise the flux of substrate through the n-3 pathway. Similarly, the Ost809Δ4 activity will prove useful in the specific conversion of DPA to DHA in transgenic photosynthetic organisms, whilst the FcELO6 activity provides a means by which GLA can be elongated to 20:3n-3.

Example 3

Expression of Single Omega-3 LC-PUFA Biosynthetic Genes in *Pheaodactylum Tricornutum* can Increase the Endogenous Accumulation of DHA Materials and Methods
Strains and Growth Conditions

*P. tricornutum* UTEX 646 was grown in ESAW medium (Harrison et al., 1980) at 20° C. with moderate shaking under white fluorescent lights in constant illumination (100 μmol photons m$^{-2}$ s$^{-1}$). Analysis of the wild-type and transgenic algae have been performed during stationary growth phase.

Plasmid Design and Cloning

The coding sequence for Δ6-elongase FcElo6 (protein ID 177742) was used as a template to chemically synthesize (Genscript Corporation, N.J.) a codon-optimized nucleotide sequencea for expression in T. pseudonana. The codon-optimized sequence was inserted as EcoRV-SacI fragments, respectively, into pPha-T1 vector (Kroth, 2007; Zaslayskaia et al., 2000).

Results

Expression of FcElo6 resulted in increase of DHA levels up to 14-17% (FIG. 13).

Example 4

Co-expression of Two Genes

Material and Methods
Design of Double-gene Vector pPhOS2 and Transformation Cassettes The EcoRI-HindIII fragment of of pPha-T1 vector containing MCS was replaced by the synthetic sequence comprising of fcpA terminator and fcpA promoter flanked by 3 multiple cloning sites (MCSs) with unique restriction sites (FIG. 14). The coding sequences for O. tauri Δ5-elongase OtElo5 was inserted as KpnI-SacI fragment into position 1 of pPhOS vector generating pPhOS2.1.1 construct. The codon optimized for expression in P. tricornutum coding sequences for O. tauri Δ6-desaturase OtD6Pt was inserted as BamHI-XbaI fragment into position 2 of pPhOS2.1.1 generating pPhOS2.2.1 construct.

Results and Discussion
Multigene expression in transgenic P. tricornutum

Figure 1:
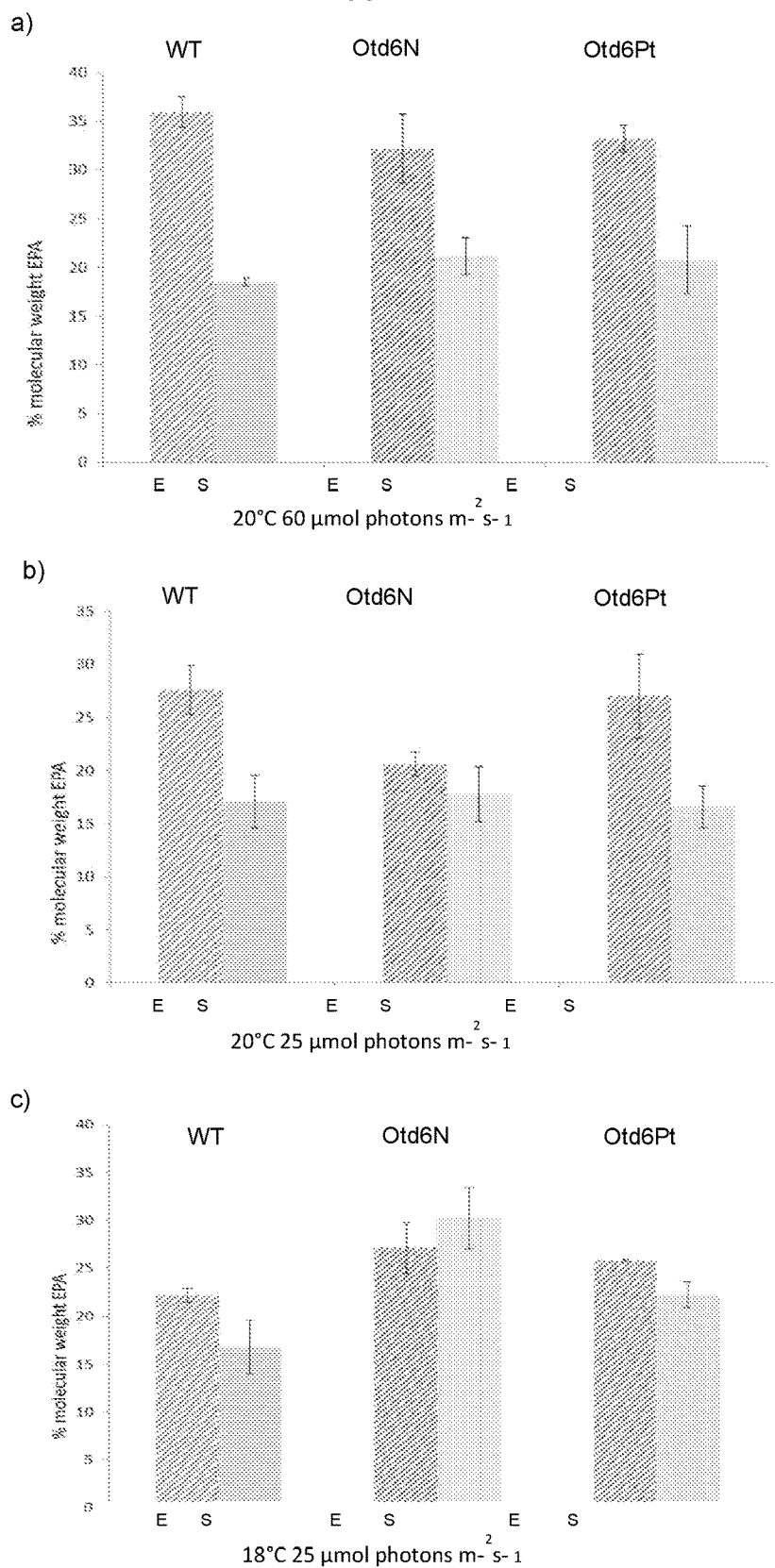
FIG. 1: EPA content in WT and transgenic *P. tricornutum* expressing *O. tauri* Δ6 desaturase under different growth conditions at two different growth stages: 20° C. 60 µmol photons $m^{-2}s^{-1}$ (FIG. 1a); 20° C. 25 µmol photons $m^{-2}s^{-1}$ (FIG. 1b); and 18° C. 25 µmol photons $m^{-2}s^{-1}$ (FIG. 1c).

To facilitate the expression of multiple heterologous genes in P. tricornutum, a new vector (designated pPhOS2— FIG. 14) was constructed. This vector is based on previously described pPha-T1 vector (Zaslayskaia et al., 2000) and contains two multiple cloning sites (MCS) with unique restriction sites for inserting genes of interest. Each of these MCS is flanked by the promoter and terminator regions of the FcpA gene (Zaslayskaia et al., 2000) to promote the co-expression of two inserted genes. The coding sequence for O. tauri Δ5-elongase OtElo5 was inserted into position 1 of pPhOS2 vector and the resulting construct pPhOS2.1.1 was used to transform P. tricornutum. Cultures were grown at 20° C. and 16° C. under constant illumination (60 μmol photons m$^{-2}$ s$^{-1}$). Multiple (5) independent zeocin-resistant colonies were obtained and used to inoculate cultures for further GC-MS analysis. The mean levels of DHA in analysed pPhOS2.1.1 strains was 9.0% (Table VIII; FIG. 1), similar to levels previously observed with OtElo5 expression in pPHa-T1, confirming the functionality of this modified vector. The codon-optimized coding sequences for O. tauri Δ6-desaturase OtD6Pt was subsequently inserted into position 2 of construct pPhOS2.1.1, generating the two-gene (plus the selectable marker gene ble) pPhOS2.2.1 vector. This expression plasmid was introduced into P. tricornutum via biolistics and multiple independent zeocin-resistant colonies were obtained and used to inoculate cultures for further screening. Cultures were grown at 16 and 20° C. under constant illumination (60 μmol photons m$^{-2}$ s$^{-1}$). FAMEs analysis of transgenic strains expressing either single or double gene constructs revealed a further increase in DHA levels in transgenic strains co-expressing both OtElo5 and OtD6Pt, indicating the here-demonstrated potential for iterative metabolic engineering in P. tricornutum for high value lipid traits (FIG. 15, Table VIII).

TABLE VIII

Fatty acid composition (Mol %) of wild-type (Pt_WT) and transgenic P. tricornutum expressing pPhOS2.1 and pPhOS2.2 at 16° C. and 20° C. Each measurement is the average of 3 biological replicates (±Standard Error).

| Fatty Acids | Pt_WT | | pPhOS2.1 | | pPhOS2.2 | |
| --- | --- | --- | --- | --- | --- | --- |
| | 16° C. | 20° C. | 16° C. | 20° C. | 16° C. | 20° C. |
| 14:0 | 5.3 ± 0.2 | 4.8 ± 0.1 | 5.1 ± 0.2 | 5.3 ± 0.3 | 6.7 ± 0.2 | 6.3 ± 0.1 |
| 16:0 | 22.3 ± 1.0 | 22.1 ± 0.4 | 19.2 ± 0.4 | 18.9 ± 1.4 | 17.7 ± 0.5 | 18.4 ± 0.3 |
| 16:1 | 39.2 ± 1.6 | 41.8 ± 0.3 | 39.0 ± 0.6 | 40.1 ± 1.7 | 43.6 ± 1.0 | 40.6 ± 0.5 |
| 16:3 | 0.8 ± 0.4 | 1.0 ± 0.1 | 1.2 ± 0.1 | 1.8 ± 0.4 | nd | 2.0 ± 0.1 |
| 18:0 | 0.5 ± 0.0 | 0.5 ± 0.1 | 0.6 ± 0.1 | 0.3 ± 0.1 | 0.5 ± 0.0 | 0.3 ± 0.1 |
| 18:1 n-9 | 6.8 ± 0.0 | 4.3 ± 0.1 | 2.6 ± 0.1 | 2.2 ± 0.4 | 1.2 ± 0.6 | 0.6 ± 0.4 |
| 18:1 n-11 | 2.2 ± 0.1 | 2.8 ± 0.1 | 2.1 ± 0.2 | 4.2 ± 0.3 | 2.7 ± 0.1 | 3.7 ± 1.0 |
| 18:4 n-7 | 1.0 ± 0.1 | 1.0 ± 0.1 | 1.7 ± 0.1 | 1.1 ± 0.1 | 1.6 ± 0.0 | 1.1 ± 0.1 |
| 20:5 n-3 | 20.3 ± 1.9 | 18.5 ± 0.1 | 10.4 ± 0.3 | 9.8 ± 1.0 | 10.0 ± 0.4 | 8.2 ± 0.1 |
| 22:5 n-3 | nd | nd | 3.4 ± 0.4 | 1.9 ± 0.3 | 5.5 ± 0.1 | 2.2 ± 0.3 |
| 22:6 n-3 | 1.5 ± 0.2 | 1.3 ± 0.1 | 9.0 ± 0.3 | 9.4 ± 1.0 | 10.3 ± 0.4 | 11.4 ± 0.2 |
| 24:0 | 2.9 ± 0.4 | 2.4 ± 0.1 | 3.2 ± 0.1 | 2.3 ± 0.2 | 3.3 ± 0.1 | 2.2 ± 0.8 |
| Others | 2.0 ± 0.5 | 1.9 ± 0.1 | 1.1 ± 0.1 | 2.9 ± 0.5 | 2.9 ± 0.3 | 3.2 ± 0.2 |

Example 5

Auxorophic Growth

Material and Methods
Design of Double-gene Vector pPhOS2 and Transformation Cassettes The EcoRI-HindIII fragment of of pPha-T1 vector containing MCS was replaced by the synthetic sequence comprising of fcpA terminator and fcpA promoter flanked by 3 multiple cloning sites (MCSs) with unique restriction sites (FIG. 16). The coding sequences for O. tauri Δ5-elongase OtElo5 was inserted as KpnI-SacI fragment into position 1 of pPhOS vector generating pPhOS2.1.1 construct. The codon optimized for expression in P. tricornutum coding sequences for glucose transporters from Physcomitrella patens (designated Ppglut1), and human erythrocytes (designated Hsglut1), were inserted as BamHI-XbaI fragments into position 2 of pPhOS2.1.1 generating pPhOS_Ppglut and pPhOS_HSglut constructs. The resulting constructs were used to transform P. tricornutum via biolistics.

Results

Multiple (>10) independent zeocin-resistant colonies were obtained by transformations with these two expression cassettes and used to inoculate cultures for further GC-MS analysis. Transgenic *P. tricornutum* strains expressing pPhOS_Ppglut and pPhOS_HSglut constructs accumulating DPA and elevated levels of DHA were selected for further analysis. (FIG. 16 and FIG. 17). The transformants were transferred to solid medium containing 0.5% of glucose, placed in complete darkness and monitored for growth (FIG. 18).

REFERENCES

Ahmann, K., Heilmann, M., Feussner, I., 2011. Identification of a D4-desaturase from the microalga *Ostreococcus lucimarinus*. Eur. J. Lipid Sci. Technol 113, 7, 832-840.

Arao, T., Kawaguchi, A., Yamada, M., 1987. Positional distribution of fatty acids in lipids of the marine diatom, *Phaeodactylum tricornutum*. Phytochemistry 26, 2573-2576.

Arao, T., Yamada, M., 1994. Biosynthesis of polyunsaturated fatty acids in the marine diatom, *Phaeodactylum tricornutum*. Phytochemistry 35, 1177-1181.

Bigogno, C., Khozin-Goldberg, I., Boussiba, S., Vonshak, A., Cohen, Z., 2002. Lipid and fatty acid composition of the green oleaginous alga *Parietochloris incisa*, the richest plant source of arachidonic acid. Phytochemistry 60, 497-503.

Blanchemain, A., Grizeau, D., 1999. Increased production of eicosapentaenoic acid by *Skeletonema costatum* cells after decantation at low temperature. Biotechnol. Tech 13. 497-501.

Calder, P. C., 2003. N-3 polyunsaturated fatty acids and inflammation: from molecular biology to the clinic. Lipids 38, 343-352.

Cohen, Z., Khozin-Goldberg, I., Adlrestein, D., Bigogno, C., 2000. The role of triacylglycerols as a reservoir of polyunsaturated fatty acids for the rapid production of chloroplastic lipids in certain microalgae. Biochem. Soc. Trans. 28, 740-743.

Das, U., N., 2002. The lipids that matter from infant nutrition to insulin resistance. Prostaglandins Leukot Essent Fatty Acids 67, 1-12.

Deviah, S. P., Roth M. R., Baughman E., Li M., Tamura P., Jeannotte R., Welti R., Wang X., 2006. Quantitative profiling of polar glycerolipid species from organs of wild-type *Arabidopsis* and a PHOSPHOLIPASE Da1 knockout mutant. Phytochemistry 67, 1907-1924.

Domergue F., Lerchl J., Zahringer U., Heinz E., 2002. Cloning and functional characterization of *Phaeodactylum tricornutum* front-end desaturases involved in eicosapentaenoic acid biosynthesis. Eur J Biochem 269, 4105-4113.

Domergue F, Abbadi A, Zahringer U, Moreau H, Heinz E, 2005. In vivo characterization of the first acyl-CoA Δ6-desaturase from a member of the plant kingdom, the microalgae *Ostreococcus tauri*. Biochem J 389, 483-490.

Garces, M., Mancha, R., 1993. One-Step Lipid Extraction and Fatty Acid Methyl Esters Preparation from Fresh Plant Tissues. Analytical Biochemistry 211, 139-143.

Harwood, J. L., Guschina I. A., 2009. The versatility of algae and their lipid metabolism. Biochemie. 91, 679-684.

Harrison, P. J., Waters R. E., Taylor. F. J. R., 1980. A broad spectrum artificial medium for coastal and open ocean phytoplankton. J. Phycol. 16, 28-35.

Haynes, C. A., Allegood, J. C., Sims, K., Wang, E. W., Cameron Sullards, M., Merril, A. H., 2008. Quantitation of fatty acyl-coenzyme As in mammalian cells by liquid chromatography-electrospray ionization tandem mass spectrometry, J. Lipid Res. 49, 1113-1125.

Harwood, J. L., 1998. Membrane lipids in algae. In Lipids in Photosynthesis: Structure, Function and Genetics (Siegenthaler, P. A. and Murata, N., eds). Dordrecht, The Netherlands: Kluwer Academic Publishers 53-64.

Hu, Q., Sommerfeld, M., Jarvis, E., Ghirardi, M., Posewitz, M., Seibert, M., Darzins, A., 2008. Microalgal triacylglycerols as feedstocks for biofuel production: perspectives and advances. Plant J. 54, 621-639.

Horrocks, L. A., Yeo, Y. K., 1999. Health benefits of DHA. Pharmacological Research 40, 211-225.

Jiang, Y., Chen F., 2000. Effects of temperature and temperature shift on docosahexaenoic acid production by the marine microalga *Crypthecodinium cohnii*. J. Am. Oil. Chem. Soc 77 613-617.

Kitano, M.; Matsukawa, R., Karube, I., 1997. Changes in eicosapentaenoic acid content of *Navicula saprophilla*, *Rhodomonas salina* and *Nitzschia* sp. under mixotrophic conditions. J. Appl. Phycol 9, 559-563.

Krank J., Murphy R. C., Barkley R. M., Duchoslav, E., McAnoy, A., 2007. Qualitative analysis and quantitative assessment of changes in neutral glycerol lipid molecular species within cells. Methods in Enyzmology 432, 1-20.

Kroth, P., 2007. Genetic transformation: a tool for study protein targeting in diatoms. Methods in Molecular Biology (Clifton, N.J.) 390, 257.

Kyle, D. J., Sicotte, V. J., Singer, J. and Reeb, S. E., 1992. Bioproduction of docosahexaenoic acid (DHA) by microalgae. In Industrial Applications of Single Cell Oils (Kyle, D. J. and Ratledge, C., eds). Champaign, Ill.: American Oil Chemists' Society. 287-300.

Larson, T. R. and Graham, I. A., 2001. A novel technique for the sensitive quantification of acyl CoA esters from plant tissues. Plant J. 25, 115-125.

Meyer A., Kirsch H, Domergue F, Abbadi A, Sperling P, Bauer J, Cirpus P, Zank T K, Moreau H, Roscoe T J, Zähringer U, Heinz E., 2004. Novel fatty acid elongases and their use for the reconstitution of docosahexaenoic acid biosynthesis. Journal of Lipid Research 45, 1899-1909.

Molina Grima, E., Sanchez Perez, J. A., Garcia Sanchez, J. L., Garcia Camacho, F. Lopez Alonso, D., 1992. EPA from *Isochrysis galbana*. Growth conditions and productivity. Process Biochem 27, 299-305.

Molina Grima, E., Robles Medina, A., Gimenez Gimenez, A., Ibanez Gonzalez, M. J. 1996. Gram-scale purification of eicosapentaenoic acid (EPA, 20: 5n-3) from wet *Phaeodactylum tricornutum* UTEX 640 biomass. J. Appl. Phycol. 8, 359-367.

Moreno, V. J., De Moreno, J. E. A., Brenner, R. R., 1979. Biosynthesis of unsaturated fatty acids in the diatom *Phaeodactylum tricornutum*. Lipids 14, 15-19.

Navarro, E., Esteve, M., Olivé, A., 2000. Abnormal fatty acid pattern in rheumatoid arthritis. A rationale for treatment with marine and botanical lipids. J Rheumatol. 27, 298-303.

Nugent, A. P., 2004. The metabolic syndrome, Nutr Bull, 29, 36-43.

Ohta S., Chang, T., Aozasa, O., Ikegami, N., Miyata, H., 1993. Alterations in fatty acid composition of marine red alga *Porphyridium purpureum* by environmental factors. Bot. March, 36, 103-107.

Qiang, H., Zhengyu, H., Cohen, Z., Richmond, A., 1997. Enhancement of eicosapentaenoic acid (EPA) and (I)³-linolenic acid (GLA) production by manipulating algal density of outdoor cultures of *Monodus subterraneus* (Eustigmatophyta) and *Spirulina platensis* (Cyanobacteria). Eur. J. Phycol 32, 81-86.

Qiu, X., Hong, H., MacKenzie, S. L., 2001. Identification of a ☐4 fatty acid desaturase from *Thraustochytrium* sp. involved in the biosynthesis of docosahexanoic acid by heterologous expression in *Saccharomyces cerevisiae* and *Brassica juncea*. J. Biol. Chem 276, 31561-6.

Radakovits, R., Eduafo, P., Posewitz M., 2011. Genetic engineering of fatty acid chain length in *Phaeodactylum tricornutum*. Metab. Eng 13, 89-95.

Renaud, S. M., Parry, D. L., Thinh, L. V., 1994. Microalgae for use in tropical aquaculture: I. Gross chemical and fatty acid composition of twelve species of microalgae from the North Territory, Australia. J. Appl. Phycol 6, 337-345.

Renaud, S. M., Thinh, L. V., Parry, D. L., 1999. The gross chemical composition and fatty acid composition of 18 species of tropical Australian microalgae for possible use in mariculture. Aquaculture 170, 147-159.

Roessler, P. G., 1990. Environmental control of glycerolipid metabolism in microalgae: commercial implications and future research directions. J. Phycol 26, 393-399.

Ruiz-Lopez N., Haslam R. P., Venegas-Caleron M., Li T., Bauer J., Napier J. A., 2012. Enhancing the accumulation of omega-3 long chain polyunsaturated fatty acids in transgenic *Arabidopsis thaliana* via iterative metabolic engineering and genetic crossing. Transgenic Res 18.

Sayanova, O., Smith, M. A., Lapinskas, P., Stobart, A. K., Dobson, G., Christie, W. W., Shewry, P. R., Napier, J. A., 1997. Expression of a borage desaturase cDNA containing an N-terminal cytochrome b5 domain results in the accumulation of high levels of Δ6-desaturated fatty acids in transgenic tobacco. Proc. Natl. Acad. Sci. USA 94, 4211-6.

Sayanova, O., Beaudoin, F., Michaelson, L., Shewry, P., Napier, J. A., 2003. Identification of *Primula* fatty acid $\Delta^6$-desaturases with n-3 substrate preferences. FEBS Lett 542, 100-104.

Sayanova O., Ruiz-Lopez N., Haslam R. P., Napier J. A., 2012. The role of Δ6-desaturase acyl-carrier specificity in the efficient synthesis of long-chain polyunsaturated fatty acids in transgenic plants. Plant Biotechnology Journal 10, 195-206.

Seto, A., Wang, H. L., Hesseltine C. W., 1984. Culture conditions affect eicosapentaenoic acid content of *Chlorella minutissima*. J. Am. Oil Chem. Soc 61, 892-894.

Siaut, M., Heijde, M., Mangogna, M., Montsant, A., Coesel, S., Allen, A., Manfredonia, A., Falciatore, A., Bowler, C., 2007. Molecular toolbox for studying diatombiology in *Phaeodactylum tricornutum*. Gene 406, 23-35.

Springer, M., Franke, H., Pulz, O., 1994. Increase of the content of polyunsaturated fatty adds in *Porphyridium cruentum* by low-temperature stress and acetate supply. J. Plant Physiology 143, 534-537.

Stinson, E. E., Kwoczak, R., Kurantz, M., 1991. Effect of culture conditions on production of eicosapentaenoic acid by *Pythium irregular* J. Ind. Microbiol 8, 171-178.

Sukenik A., 1991, Ecophysiological considerations in the optimization of eicosapentaenoic acid production by *Nannochloropsis* sp. (Eustigmatophyceae) Bioresour. Technol 35, 263-269.

Tan, C. K., Johns, M. R., 1996. Screening of diatoms for heterotrophic eicosapentaenoic acid production. J. Appl. Phycol 8, 59-64.

Tonon T., Harvey D., Tony R. Larson T. R. Graham I. A., 2002. Long chain polyunsaturated fatty acid production and partitioning to triacylglycerols in four microalgae. Phytochemistry 61, 15-24.

Venegas-Caleron M., Sayanova O., Napier J. A., 2010. An alternative to fish oils: metabolic engineering of oil-seed crops to produce omega-3 long chain polyunsaturated fatty acids. Prog Lipid Res 49, 108-119.

Voigt, R. G., Jensen, C. L. Fraley, J. K., Rozelle, J. C., Brown, F. R., Heird, W. C., 2000. Relationship between omega-3 long-chain polyunsaturated fatty acid status during early infancy and neurodevelopmental status at 1 year of age. J Hum Nutr Diet 15, 111-120.

Wagner. M., Hoppe, K., Czabany., T., Heilmann, M., Daum, G., Feussner, I., Fulda, M., 2010. Identification and characterization of an acyl-CoA:diacylglycerol acyltransferase 2 (DGAT2) gene from the microalga *O. tauri*. Plant Physiology and Biochemistry 48, 6, 407-416.

Welti, R., Li, W., Li, M., Sang, Y., Biesiada, H. Zhou, H. E., Rajashekar, C. B., Williams, T. D., Wang, X., 2002. Profiling membrane lipids in plant stress responses. Role of phospholipase D alpha in freezing-induced lipid changes in *Arabidopsis*. J Biol Chem. 30, 277, 35, 31994.

Wen, Z. Y., Chen, F. 2001. Optimization of nitrogen sources for heterotrophic production of eicosapentaenoic acid by the diatom *Nitzschia laevis*. Enzyme Microb. Technol 29, 341-347.

Xiao, S., Gao, W., Chen, Q. F., Chan, S. W., Zheng, S. X., Ma, J., Wang, M., Welti, R., Chye, M. L. 2010. Overexpression of *Arabidopsis* acyl-CoA binding protein ACBP3 promotes starvation-induced and age-dependent leaf senescence. Plant Cell 22, 5, 1463-82.

Yongmanitchai, W., Ward, O. P., 1989. Omega-3 fatty adds: alternative sources of production. Process Biochem 24, 117-125.

Yongmanitchai, W., Ward, O., 1991. Growth and omega-3 fatty acid production by the *Phaeodactylum tricornutum* under different culture conditions. Applied and Environmental Microbiology 419-425.

Yongmanitchai, W., Ward, O. P., 1993. Positional distribution of fatty acids, and molecular species of polar lipids, in the diatom *Phaeodactylum tricornutum*. J Gen Microbiol 139, 465-472.

Yu, E. T., Zendejas, F. J., Lane P. D., Gaucher, S., Simmons B. A., Lane, T. W., 2009. Triacylglycerol accumulation and profiling in the model diatoms *Thalassiosira pseudonana* and *Phaeodactulum tricornututm* (Baccilariophyseae) during starvation. J Appl Phycol 21, 669-681.

Zaslayskaia, L. A., Lippmeier, J. C., Kroth, P. G., Grossman, A. R., Apt, K. E., 2000. Transformation of the diatom *Phaeodactylum tricornutum* (*Bacillariophyceae*) with a variety of selectable marker and reporter genes. J. Phycol 36, 379-986.

SEQUENCE LISTING

Nucleic acids analogous to cDNA are shown.

```
Nucleic acid sequence OtElo5
                                                   SEQ ID No 1
atgagcgcctccggtgcgctgctgcccgcgatcgcgtccgccgcgtacgcgtacgcgacg tacgcctacgcctttgagtggtcgcacgcgaatggcatcgacaacgtcgacgcgcgcgag tggatcggtgcgctgtcgttgaggctcccggcgatcgcgacgacgatgtacctgttgttc tgcctggtcggaccgaggttgatggcgaagcgcgaggcgttcgacccgaaggggttcatg
```

-continued ctggcgtacaatgcgtatcagacggcgttcaacgtcgtcgtgctcgggatgttcgcgcga gagatctcggggctggggcagcccgtgtgggggtcaaccatgccgtggagcgatagaaaa tcgtttaagatcctcctcggggtgtggttgcactacaacaacaaatatttggagctattg gacactgtgttcatggttgcgcgcaagaagacgaagcagttgagcttcttgcacgtttat catcacgccctgttgatctgggcgtggtggttggtgtgtcacttgatggccacgaacgat tgtatcgatgcctacttcggcgcggcgtgcaactcgttcattcacatcgtgatgtactcg tattatctcatgtcggcgctcggcattcgatgcccgtggaagcgatacatcacccaggct caaatgctccaattcgtcattgtcttcgcgcacgccgtgttcgtgctgcgtcagaagcac tgcccggtcacccttccttgggcgcaaatgttcgtcatgacgaacatgctcgtgctcttc gggaacttctacctcaaggcgtactcgaacaagtcgcgcggcgacggcgcgagttccgtg aaaccagccgagaccacgcgcgcgcccagcgtgcgacgcacgcgatctcgaaaaattgac taa Amino acid sequence OtElo5
SEQ ID No 2
MSASGALLPAIASAAYAYATYAYAFEWSHANGIDNVDAREWIGALSLRLPAIATT

MYLLFCLVGPRLMAKREAFDPKGFMLAYNAYQTAFNVVVLGMFAREISGLGQPVW

GSTMPWSDRKSFKILLGVWLHYNNKYLELLDTVFMVARKKTKQLSFLHVYHHALL

IWAWWLVCHLMATNDCIDAYFGAACNSFIHIVMYSYYLMSALGIRCPWKRYITQA

QMLQFVIVFAHAVFVLRQKHCPVTLPWAQMFVMTNMLVLFGNFYLKAYSNKSRGD

GASSVKPAETTRAPSVRRTRSRKID*

OtD6 nucleic acid sequence
SEQ ID No 3
atgtgcgtggagacggaaaataacgatgggatccccacggtggagatcgcgttcgacggt gagcgcgagcgggcggaggcaaacgtgaagctgtccgcggagaagatggagccggcggcg ctggcgaagacgttcgcgaggcggtacgtcgtgatcgaggggtggagtacgatgtgacg gattttaagcacccgggaggaacggttattttctatgcgttgtcaaacaccggggcggac gcgacggaagcgttcaaggagtttcatcatcggtcgagaaaggcgaggaaagccttggcg gcgctcccgtctcgaccggccaagacggccaaggtggacgacgcggagatgctccaagat ttcgccaagtggcggaaagaattggagagagatggattcttcaagccctctccggcgcac gtggcgtatcgcttcgccgagctcgcggcgatgtacgctctcgggacgtacctgatgtac gctcgatacgtcgtctcctcggtgctcgtgtacgcttgcttttcggcgcccgatgcgt tgggtgcagcacgagggcggacacagctcgctgacgggcaacatttggtgggacaagcgc atccaggccttcacagccgggttcggtctcgccggtagcggcgacatgtggaactcgatg cacaacaagcatcacgcgacgcctcaaaaggttcgtcacgacatggatctggacaccacc cccgcggtggcgttcttcaacaccgcggtggaagacaatcgtccccgtggctttagcaag tactggttgcgccttcaggcgtggaccttcatcccgtgacgtccggcttggtgctcctt ttctggatgttttttcctccaccccctccaaggctttgaaggggtggcaagtacgaagagttg gtgtggatgctcgccgcgcacgtcatccgcacgtggacgatcaaggcggtgaccggattc accgcgatgcagtcctacggcttattttttggcgacgagctgggtgagcggctgctatctg tttgcacacttctccacgtcgcacacgcacctggatgtggtgcccgcggacgagcatctc tcctgggttcgatacgccgtcgatcacacgatcgacatcgatccgagtcaaggttgggtg aactggttgatgggctacctcaactgccaagtcatccaccacctctttccgagcatgccg -continued

```
cagttccgccagcccgaggtatctcgccgcttcgtcgcctttgcgaaaaagtggaacctc aactacaaggtcatgacctacgccggtgcgtggaaggcaacgctcggaaacctcgacaac gtgggtaagcactactacgtgcacggccaacactccggaaagacggcgtaa
```

OtD6 amino acid sequence
SEQ ID No 4

```
MCVETENNDGIPTVETAFDGERERAEANVKLSAEKMEPAALAKTFARRYVVIEGVEYDVT

DFKHPGGTVIFYALSNTGADATEAFKEFHHRSRKARKALAALPSRPAKTAKVDDAEMLQD

FAKWRKELERDGFFKPSPAHVAYRFAELAAMYALGTYLMYARYVVSSVLVYACFFGARCG

WVQHEGGHSSLTGNIWWDKRIQAFTAGFGLAGSGDMWNSMHNKHHATPQKVRHDMDLDTT

PAVAFFNTAVEDNRPRGFSKYWLRLQAWTFIPVTSGLVLLFWMFFLHPSKALKGGKYEEL

VWMLAAHVIRTWTIKAVTGFTAMQSYGLFLATSWVSGCYLFAHFSTSHTHLDVVPADEHL

SWVRYAVDHTIDIDPSQGWVNWLMGYLNCQVIHHLFPSMPQFRQPEVSRRFVAFAKKWNL

NYKVMTYAGAWKATLGNLDNVGKHYYVHGQHSGKTA*
```

OtD6Pt nucleic acid sequence optimised codon
SEQ ID No 5

```
ggtaccaagcttgatatcaccaaaatgtgtcgaaacggaaaacaacgatggaatccccacgg tcgaaattgcctttgatggagaacgcgaacgcgccgaagccaacgtcaagctctccgccgaaaa gatggaacccgccgccttggccaagaccttcgcccgtcgctacgtcgtcattgaaggtgtcgaa tacgatgtcaccgacttcaagcacccggaggtacggtcatcttttacgccctctccaacaccg gagccgacgccacggaagccttcaaggaatttcaccaccgttcccgcaaggcccgtaaggccct cgccgccttgccctcgcgcccggccaagaccgccaaggtcgacgatgccgaaatgcttcaggat ttcgccaagtggcgtaaggaactcgaacgcgacggcttcttttaagccctccccggcccacgtcg cctaccgttttgccgaactcgccgccatgtacgcccttggaacctacctcatgtacgcccgtta cgtcgtctcctcggtcttggtctacgcctgcttctttggtgcccgctgtggatgggtccagcac gaaggcggacactcctcgctcaccggaaacatttggtgggataagcgtatccaagccttcacgg ccggatttggtttggccggctccggagacatgtggaactcgatgcacaacaagcaccacgccac cccccagaaggtccgtcacgacatggatctcgacaccacgccggccgtcgccttctttaacacc gccgtcgaagataaccgtccccgcggattctccaagtactggcttcgtctccaagcctggacct tcattcccgtcacgtccggtttggtcctcttgttttggatgttctttcttcaccgtcgaaggc cctcaagggtggcaagtacgaagaattggtctggatgcttgccgcccacgtcattcgtacctgg acgatcaaggccgtcaccggtttcacggccatgcagtcctacggcttgtttcttgccacctcct gggtctcgggttgctacctcttcgcccacttttccacctcgcacacgcacttggatgtcgtccc cgccgacgaacacctttcctgggtccgctacgccgtcgaccacaccattgacattgacccgtcg cagggatgggtcaactggctcatgggttacttgaactgtcaagtcatccaccacctcttcccct ccatgccgcagtttcgtcaaccccgaagtctcgcgtcgcttcgtcgcctttgccaagaagtggaa cttgaactacaaggtcatgacctacgccggagcctggaaggccacgcttggaaaccttgataac gtcggaaagcactactacgtccacggccagcactcgggaaagaccgcctaagagctcggtaccc tcgag
```

OtD6 amino acid sequence optimised codon
SEQ ID No 6

```
MCVETENNDGIPTVETAFDGERERAEANVKLSAEKMEPAALAKTFARRYVVIEGVEYDVT

DFKHPGGTVIFYALSNTGADATEAFKEFHHRSRKARKALAALPSRPAKTAKVDDAEMLQD

FAKWRKELERDGFFKPSPAHVAYRFAELAAMYALGTYLMYARYVVSSVLVYACFFGARCG

WVQHEGGHSSLTGNIWWDKRIQAFTAGFGLAGSGDMWNSMHNKHHATPQKVRHDMDLDTT
```

PAVAFFNTAVEDNRPRGFSKYWLRLQAWTFIPVTSGLVLLFWMFFLHPSKALKGGKYEEL

VWMLAAHVIRTWTIKAVTGFTAMQSYGLFLATSWVSGCYLFAHFSTSHTHLDVVPADEHL

SWVRYAVDHTIDIDPSQGWVNWLMGYLNCQVIHHLFPSMPQFRQPEVSRRFVAFAKKWNL

NYKVMTYAGAWKATLGNLDNVGKHYYVHGQHSGKTA

Δ6-desaturase nucleic acid from *Ostreococcus* RCC809

SEQ ID No 7 atgcgcgtcgaaacggaggacgacaacgttccgacggtcaccgtcggactgtcggaggag agcgacgggatgaagggggcgagaaaccccggggcgcgggcgtggaaatcgacgctcgag ccgcacgcggtggccaagtcgttcgatcgacggtgggtcaaggttgacggcgtcgagtac gacgtcacggattttaagcatccgggtggatctgtgatttattacatgctgtcgaacacc ggagcggacgcgacggaggcgttcaaagagtttcattatcggtcgaaaaaggcgagaaag gcgttggcggcgttgccgcagcgcgagccggaggacgcgtcgccagtggaagacgcgaat atgttgaaggatttcgcgaaatggcgcaaagatttggagcgcgagggtttctttaaaccg tcgccggcgcacgtggcgtacagattcgcggaactcgcggccatgttcgcgctcgggacg gcgttgatgtacgctcgatggcacgccacctcagtcttcgtcaccgcgtgcttttcggc gcgcggtgcggttgggtgcaacacgagggtggtcacagctcgctgacggggagcatttgg tgggacaagcgaatccaagcgttcaccgccggtttcggattagcatcgagcggcgacatg tggaacctcatgcacaacaagcaccacgccactccgcaaaaggtgcgacacgacatggac ctcgacaccacgccggcggtggccttcttcaacactgcggtcgaggaaaaccgtccgcgc aagttcagtaagttatggttgcgcgtgcaggcgtggacgttcgtcccggtcacctctggt ttggtgttgctcgcctggatgtaccttgcatccgagacacattgctcgccgtaaaaac tacgaagaggctgcgtggatcgtcgccgcgcacgtcatccgcacgtcggtcatcaaagcc gtgaccggttactcctggatcacgtgctacggtttgttcttgtccaccatgtgggtgagc ggctgctacctctttgcgcacttctccacgtctcacacgcacctcgacgtcgttccgagc gataagcatctctcttgggtgcgatacgccgtcgaccacaccatcgacatcgacccgagc aagagcgtcgtcaactggttgatgggttacctgaactgccaggtcatccatcacttgttt ccggacatgcctcagttccgtcagcccgaagtctctcgccgcttcgtctcctttgcgaaa aagtggaacctcaattacaaggtcatgagctactacggcgcgtggaaggccaccttcggt aacttgaacgaggtcggcaagcactattacatccaaggttctcaaatcacgaagaagacg gtgtaa Δ6-desaturase amino acid from *Ostreococcus* RCC809

SEQ ID No 8

MRVETEDDNVPTVTVGLSEESDGMKGARNPGARAWKSTLEPHAVAKSFDRRWVKVDGVEYDVTD

FKHPGGSVIYYMLSNTGADATEAFKEFHYRSKKARKALAALPQREPEDASPVEDANMLKDFAKW

RKDLEREGFFKPSPAHVAYRFAELAAMFALGTALMYARWHATSVFVTACFFGARCGWVQHEGGH

SSLTGSIWWDKRIQAFTAGFGLASSGDMWNLMHNKHHATPQKVRHDMDLDTTPAVAFFNTAVEE

NRPRKFSKLWLRVQAWTFVPVTSGLVLLAWMYLLHPRHIARRKNYEEAAWIVAAHVIRTSVIKA

VTGYSWITCYGLFLSTMWVSGCYLFAHFSTSHTHLDVVPSDKHLSWVRYAVDHTIDIDPSKSVV

NWLMGYLNCQVIHHLFPDMPQFRQPEVSRRFVSFAKKWNLNYKVMSYYGAWKATFGNLNEVGKH

YYIQGSQITKKTV

-continued

Δ6-desaturase (Ost809Δ6) nucleic acid from *Ostreococcus* RCC809
codon optimised for expression in *T. pseudonana*
SEQ ID No 9 atgcgtgtggaaaccgaagacgataatgtgccaactgttactgtgggattgtcagaggagtccg atggaatgaagggagcaaggaaccccggagcacgtgcttggaagtcgacgttggagccgcacgc cgtggcaaagtcattcgatcgtaggtgggttaaggttgacggagtcgaatacgacgtaactgat ttcaagcatcccggaggatcagttatctactatatgctttctaacaccggagctgatgccactg aggctttcaaggaatttcactatcgtagtaagaaggccaggaaggcacttgctgccctcccaca acgtgagcctgaagacgcttcgccagtcgaggatgccaatatgctcaaggacttcgcaaagtgg cgtaaggatttggagagggaaggattctttaagccaagtcctgctcacgtggcctaccgtttcg ccgaactcgcagctatgtttgctttgggaactgcccttatgtatgcacgttggcatgctacgtc tgtcttcgtaacagcctgtttctttggagcaaggtgtggatgggtgcaacgagggaggacat tcttccttgaccggatccatctggtgggataagcgtattcaggcattcactgctggatttggac ttgccagttcgggagacatgtggaacctcatgcacaataagcaccatgcaacgccacaaaaagt taggcatgatatggacctcgataccactcctgcagtggctttctttaacacagctgttgaggaa aatcgtcctaggaagttctctaagttgtggcttcgtgtccaggcctggacctttgtgcccgtta cttccggattggtactcttggcatggatgtaccttctccacccgcgtcatatcgctcgtaggaa gaactatgaggaagccgcatggattgtggctgcccatgttatcaggacctccgtcattaaggct gtaacgggatacagttggatcacatgttatggactcttcttgtcgactatgtgggtctcaggat gctacctcttcgctcactttcaacgtctcacacacatttggacgtggttccatctgataagca cctttcctgggtgcgttacgccgttgatcataccatcgacattgatccttccaagagtgtcgta aactggctcatgggatatttgaactgtcaggttatccaccatttgttccccgacatgccgcaat ttcgtcagcccgaagtcagtcgtaggttcgtatcgtttgccaagaagtggaaccttaattacaa ggtcatgtcttactatggagcctggaaggcaaccttcggaaatctcaacgaagtcggaaagcac tactacatccaaggaagtcaaatcacaaagaagacggtttag

Δ6-desaturase amino acid from *Ostreococcus* RCC809
codon optimised
SEQ ID No 10

MRVETEDDNVPTVTVGLSEESDGMKGARNPGARAWKSTLEPHAVAKSFDRRWVKVDGVEY

DVTDFKHPGGSVIYYMLSNTGADATEAFKEFHYRSKKARKALAALPQREPEDASPVEDAN

MLKDFAKWRKDLEREGFFKPSPAHVAYRFAELAAMFALGTALMYARWHATSVFVTACFFG

ARCGWVQHEGGHSSLIGSIWWDKRIQAFTAGEGLASSGDMWNLMHNKHHATPQKVRHDMD

LDTTPAVAFFNTAVEENRPRKFSKLWLRVQAWTFVPVTSGLVLLAWMYLLHPRHIARRKN

YEEAAWIVAAHVIRTSVIKAVTGYSWITCYGLFLSTMWVSGCYLFAHFSTSHTHLDVVPS

DKHLSWVRYAVDHTIDIDPSKSVVNWLMGYLNCQVIHHLFPDMPQFRQPEVSRRFVSFAK

KWNLNYKVMSYYGAWKATFGNLNEVGKHYYIQGSQITKKTV

Δ4-desaturase from *E. huxleyi* (EhD4) codon-optimized for
expression in *Arabidopsis*
SEQ No. 11 atgggaggcgccggcgcgagcgaggctgaacggcccaagtggaccacgatccacgggcggcacg tcgatgtgtcaaagttccgccacccgggtgggaacatcatcgagctcttctatggcatggactc gacgagcgcgttcgagcagttccacggccaccacaagggcgcgtggaagatgctcaaggcgctg ccgaccaaggaggtcgaccccgccgacgtgccgcagcagccgcaggagcacgttgccgagatga cgcggctgatgacgtcgtggcgcgagcgcggcctcttttaagccgcgccccgtcgcctcgggcat ctacggtctcgccgtcgtcgctgccatcgtcgcgtgcatcgcctgcgcgccgcacgcgccggtg -continued

```
ctgagcgggatcgggctcggcagctgctgggcgcagtgcggcttcctgcagcacatgggcgggc accgcgagtgggggtgcggtactccttcctcctgcagcacttcttcgagggcctcctcaaggg cgggtccgcctcgtggtggcgcaaccgccacaacaagcatcacgcaaagactaacgtgctcggc gaggacggcgacctgcggacgactcccttcttcgcctgggacccgacgctcgccaagaaggttc cagactggtcgctcaagacgcaggccttcaccttcctcccgccctcggagcgtacgtctttgt ctttgccttcacgatccgcaagtatgccgtcgtcaagaagctctggcacgagctcgcactcatg atcgcgcactacgcgatgttctactacgcgctgcagctcgccggtgcgtcgctcggcagcggcc tcgccttttactgcaccggctacgcctggcaaggcatctacctcggcttcttcttcggcctgtc ccacttcgcggtcgagcgagtcccctccaccgccacctggctcgagtcgtccatgatcggcacc gtcgactggggaggctcctccgccttttgcggctacgtctccggcttcctcaacatccagatcg agcaccacatggcgccgcagatgccgatggagaacctgccagatccgcgccgactgcaaggc gagcgcggagaagctcgggcttccctatcgcgagctctccttcgccggcgcggtcaagctgatg atggtcggcctctggcgcacgggagggacgagctgcagctgcgctccgacaggcgcaagtact cgcgcacccaggcctacatggcggccgcctcggcggtggtggagaacctcaaggcggactag
```

Δ4-desaturases from *E. huxleyi* codon-optimized for expression in *Arabidopsis*

SEQ No. 12

MGNGNLPASTAQLKSTSKPQQQHEHRTISKSELAQHNTPKSAWCAVHSTPATDPSHSNNKQHAH

LVLDITDFASRHPGGDLILLASGKDASVLFETYHPRGVPTSLIQKLQIGVMEEEAFRDSFYSWT

DSDFYTVLKRRVVERLEERGLDRRGSKEIWIKALFLLVGFWYCLYKMYTTSDIDQYGIALAYSI

GMGTFAAFIGTCIQHDGNHGAFAQNKLLNKLAGWTLDMIGASAFTWELQHMLGHHPYTNVLDGV

EEERKERGEDVALEEKDQESDPDVESSFPLMRMHPHHTTSWYHKYQHLYAPPLFALMTLAKVFQ

QDFEVATSGRLYHIDANVRYGSVWNVMRFWAMKVITMGYMMGLPIYFHGVLRGVGLEVIGHLAC

GELLATMFIVNHVIEGVSYGTKDLVGGASHGDEKKIVKPITVLGDTPMEKTREEALKSNSNNNK

KKGEKNSVPSVPENDWAAVQCQTSVNWSPGSWFWNHFSGGLSHQIEHHLEPSICHTNYCHIQDV

VESTCAEYGVPYQSESNLEVAYGKMISHLKFLGKAKCE*

D4-desaturase from *Thalassiosira pseudonana* nucleic acid

SEQ ID No. 13

```
atgggcaacggcaacctcccagcatccaccgcacagctcaagtccacctcgaagcccagcagc aacatgagcatcgcaccatctccaagtccgagctcgcccaacacaacacgcccaaatcagcatg gtgtgccgtccactccactcccgccaccgacccatcccactccaacaacaaacaacacgcacac ctagtcctcgacattaccgactttgcgtcccgccatccaggggagacctcatcctcctcgctt ccggcaaagacgcctcggtgctgtttgaaacataccatccacgtggagttccgacgtctctcat tcaaaagctgcagattggagtgatggaggaggaggcgtttcgggattcgttttacagttggact gattctgacttttatactgtgttgaagaggagggttgtggagcggttggaggagaggggttgg acaggaggggatcgaaagagatttggatcaaggcttttgttcttgttggttggattttggtactg tttgtacaagatgtatactacgtcggatattgatcagtacggtattgccattgcctattctatt ggaatgggaacctttgcggcattcatcggcacgtgtattcaacacgatggaaatcacggtgcat tcgctcagaacaagttactcaacaagttggctgggtggacgttggatatgattggtgcgagtgc gtttacgtgggagcttcagcacatgctggggcatcatccatatacgaatgtgttggatggggtg gaggaggagaggaaggagaggggggaggatgttgctttggaagaaaaggatcaggaatcagatc cagacgtattctcctccttccctctcatgagaatgcatcccaccatacaacctcatggtatca taaataccaacacctctacgctccacccctctttgcattgatgacacttgccaaagtattccaa
```

-continued

```
caggattttgaagttgccacatccggacgattatatcatattgatgccaatgtacgttatggtt
cggtatggaatgtcatgaggttttgggctatgaaggtcattacgatgggatatatgatgggatt
accaatctactttcatggagtactgaggggagttggattgtttgttattgggcatttggcgtgt
ggagagttgttggcgacgatgtttattgtgaatcacgtcattgagggtgtgagttatggaacga
aggatttggttggtggtgcgagtcatggagatgagaagaagattgtcaagccaacgactgtatt
gggagatacaccaatgaaaagactcgcgaggaggcattgaaaagcaacagcaataacaacaag
aagaagggagagaagaactcggtaccatccgttccattcaacgactgggcagcagtccaatgcc
agacctccgtgaattggtctccaggctcatggttctggaatcacttttctgggggactctctca
tcagattgagcatcacttgttccccagcatttgtcatacaaactactgtcatatccaggatgtt
gtggagagtacgtgtgctgagtacggagttccgtatcagagtgagagtaatttgtttgttgctt
atggaaagatgattagtcatttgaagttttttgggtaaagccaagtgtgagtag
```

D4-desaturase from *Thalassiosira pseudonana* amino acid acid
SEQ ID No. 14

```
MGGAGASEAERPKWTTIHGRHVDVSKFRHPGGNIIELFYGMDSTSAFEQFHGHHKGAWKM
LKALPTKEVDPADVPQQPQEHVAEMTRLMTSWRERGLFKPRPVASGIYGLAVVAAIVACI
ACAPHAPVLSGIGLGSCWAQCGFLQHMGGHREWGVRYSFLLQHFFEGLLKGGSASWWRNR
HNKHHAKTNVLGEDGDLRTTPFFAWDPTLAKKVPDWSLKTQAFTFLPALGAYVFVFAFTI
RKYAVVKKLWHELALMIAHYAMFYYALQLAGASLGSGLAFYCTGYAWQGIYLGEFFGLSH
FAVERVPSTATWLESSMIGTVDWGGSSAFCGYVSGFLNIQIEHHMAPQMPMENLRQIRAD
CKASAEKLGLPYRELSFAGAVKLMMVGLWRTGRDELQLRSDRRKYSRTQAYMAAASAVVE
NLKAD*
```

Δ4-desaturase *Ostreococcus* RCC809 nucleic acid
SEQ ID No. 15

```
atgccgacgactcgatcgcgcgcgcgtgacgacgcccctcgcgagacgccgacgagagcga
acaccgtcgccgcgctcgatcccgagcgcaagtacacgcgcattcgcggcgtcgtgtacgacgt
cacggatttcgccagccgtcatccgggtggcgcgcaattgttatcgctgtgcgtggggagagac
gccaccatcctggtggagagtcatcaccttcgtccggaggtggtgcaaaagtacctgaagacgc
ttcccgtggtggagggcgcggcggggcgttcgggcccgaggagacgtttccgaaaccgctcga
ctcggatttgtaccgaaagattcaggggcgcgttcgtaaagagatcgtcgaaccgttgaagatg
acgcgcggacgcgagccgcacgggcgaggctggtgcgtgttggacgccggggtggtgttggctt
tcttcgcgttcgcgttgggagtctattggaagacgccgacggtggcgacggggtgcctgttggg
gctcgccgggtactggagcggcaccggattgcaacacacggcgaaccacggtggattggcgaag
agtgggttttggaatcagttttggggatggctcgggaacgacgtcgccatcgggaagagctcgg
tggagtggagatatcatcacatggtgagccaccactcgtattgcaacgacgcggacctcgatca
agacgtgtacaccgcgctgccgcttcttcgtttggacccgtcccaggagttgaagtggttccac
cgctaccaagcgttctacgcgccgctgatgtggccgatgttgtggctcgccgcgcagtttggcg
acgcgcaaaatattttagtggataaggcgtctccgggcgtcgagtacaagggcctcatgaagct
cgaagtcgcgctgtacgttctcggaaagttttttgcattttagcttgttgctcggcgtaccggcc
tacttgcacgggtttgcgaacgccatcgtgccgttcatcgcgtacggtgcgttcggttcgttcg
tcctgtgctggttttcatcgtcagtcacaacttggaggcgttgaccccaatcaatctgagcaa
atccacgaagaatgactggggcgcgtggcaaatcgaaacttccgcgtcctggggcaacggcttc
tggagcttttctccggcgggttgaatttgcaaatcgagcaccacttgttcccggggttgcgcgc
acaacttgtacccgaagatggttcccatcatcaaggaagagtgcgaaaaggctggcgtcacgta
```

-continued caccggttacggtgggtactttggtctccttcccatcactcgggacatgttcgcgtacttgtac aaaatgggccgacaaagcaaaaagtcggcgtaa Δ4-desaturase *Ostreococcus* RCC809 amino acid
SEQ ID No. 16

MPTIRSRARVITPPRETPTRANTVAALDPERKYTIRGVVYDVTDFASRHPGGAQLLSLCVGRD

ATILVESHHLRPEVVQKYLKTLPVVEGAAGAFGPEETFPKPLDSDLYRKIQGRVRKEIVEPLKM

TRGREPHGRGWCVLDAGVVLAFFAFALGVYWKIPTVATGCLLGLAGYWSGTGLQHTANHGGLAK

SGFWNQFWGWLGNDVAIGKSSVEWRYHHMVSHHSYCNDADLDQDVYTALPLLRLDPSQELKWFH

RYQAFYAPLMWPMLWLAAQFGDAQNILVDKASPGVEYKGLMKLEVALYVLGKFLHFSLLLGVPA

YLHGFANAIVPFIAYGAFGSFVLCWFFIVSHNLEALTPINLSKSTKNDWGAWQIETSASWGNGF

WSFFSGGLNLQIEHHLFPGCAHNLYPKMVPIIKEECEKAGVTYTGYGGYFGLLPITRDMFAYLY

KMGRQSKKSA*

Δ4-desaturase *Ostreococcus* RCC809 nucleic acid codon optimised acid for expression in Pt
SEQ ID No. 17 ggatccggtaccaagcttgatatcaccaaaatgccaactactcgttctcgtgctcgtgttacta ctccacctcgtgaaactcctactcgtgctaatactgttgctgctttagatccagaacgtaaata tacacgtattcgaggtgttgtatatgatgttactgattttgctagtcgacatccaggtggtgca caattattatctttatgtgttggtcgtgatgctacaattttagtagaatcacatcatttacgac cagaagttgtacaaaaatatttaaaaacattacctgttgtagaaggtgctgctggtgcatttgg tccagaagaaacttttccaaaaccttatagatagtgatttatatcgtaaaattcaaggtcgtgtt cgaaaagaaattgtagaaccattaaaaatgacacgtggtcgagaacctcatggtcgtggttggt gtgttttagatgctggtgttgtattagctttctttgcttttgcattaggtgtttattggaaaac accaactgtagctactggttgtttattaggtttagcaggttattggtctggtacaggtttacaa catactgctaatcatggtggtttagcaaaatcaggttttggaatcaattttggggttggttagg aaatgatgttgctattggtaaatcaagtgtagaatggcgttatcatcatatggttttcacatcat agttattgtaatgatgctgatttagatcaagatgtttatacagcattaccattattacgtttag atccttcacaagaattaaaatggtttcatcgttatcaagcattttatgcacctttaatgtggcc tatgttatggttagctgcacaatttggtgatgctcaaaatattttagttgataaagcaagtcca ggtgtagaatataaaggtttaatgaaattagaagttgctttatatgtattaggaaaatttta cattttctttattattaggtgttcctgcatatttacatggttttgctaatgcaattgtaccat ttattgcttatggtgcatttggttcatttgttttatgttggttttttcattgtaagtcataattt agaagcattaacaccaattaatttatctaaatcaactaaaaatgattggggtgcttggcaaatt gaaactagtgcatcttggggtaatggttttggtcattttctcaggtggtttaaatttacaaa ttgaacatcatttatttcctggttgtgctcataatttatatccaaaaatggttcctattattaa agaagaatgtgaaaagcaggtgttacatatactggttatggtggttattttggtttattacca attactcgtgatatgtttgcttatttatataaaatgggtcgtcaatctaaaaaatctgcttaag agctcggtaccctcgagtctaga Δ4-desaturase *Ostreococcus* RCC809 amino acid codon optimised acid for expression in Pt
SEQ ID No. 18

MPTIRSRARVITPPRETPTRANTVAALDPERKYTIRGVVYDVTDFASRHPGGAQLLSLCVGRD

ATILVESHHLRPEVVQKYLKTLPVVEGAAGAFGPEETFPKPLDSDLYRKIQGRVRKEIVEPLKM

TRGREPHGRGWCVLDAGVVLAFFAFALGVYWKTPTVATGCLLGLAGYWSGTGLQHTANHGGLAK

-continued

SGFWNQFWGWLGNDVAIGKSSVEWRYHHMVSHHSYCNDADLDQDVYTALPLLRLDPSQELKWFH

RYQAFYAPLMWPMLWLAAQFGDAQNILVDKASPGVEYKGLMKLEVALYVLGKFLHFSLLLGVPA

YLHGFANAIVPFIAYGAFGSFVLCWFFIVSHNLEALTPINLSKSTKNDWGAWQIETSASWGNGF

WSFFSGGLNLQIEHHLFPGCAHNLYPKMVPIIKEECEKAGVTYTGYGGYFGLLPITRDMFAYLY

KMGRQSKKSA*

Δ6-elongase from *Fragilariopsis cylindrus* nucleic acid
SEQ ID No. 19 ccatggggtaccgatatcaccaaaatggacgagtacaaagcaactcttgaatctgt tggggatgctatcatccaatgggcagatcctgaaagtcagttcaccgggttcacca agggatggttcttgacagatttcacatctgcgtttagtattgcacttgtatacgtc ttatttgtcatcattggttctcaagtgatgaaagtcttacctgctattgatccgta cccaatcaagttttttacaatgtatcacaaattatgctgtgtgcttacatgacga ttgaagcatgtctgttagcgtaccgtaacggatacactatcatgccatgtgtcgga tacaatagagatgatccagcaattggaaatcttttatggttattttatgtttcaaa agtttgggattttgggataccatctttatcgttttggggaagaagtggagacaac tttctttccttcacgtttaccatcataccaccatctttttgttctactggcttaac gcgaatgtcttttatgatggtgatatttatcttaccattgctctgaatggtttcat ccatactgttatgtacacatactactttatctgtatgcatactaaagacaagaaaa ctggaaaatcgcttcctatctggtggaaatcatctttgactttgttgcaattgttt cagttcattaccatgatgtcacagggcttatacct tatcatttttggttgtgaatc actttctatccgagtcactgcgacatacgttgtttacatattgtcacttttctttt tgtttgcgcaattcttcgttgcatcttacatgcaacctaagaaatcgaagactgcc taagagctcggtaccttaattaa Δ6-elongase from *Fragilariopsis cylindrus* amino acid
SEQ ID No. 20

MDEYKATLESVGDAIIQWADPESQFTGFTKGWFLTDFTSAFSIALVYVLFVIIGSQVMKVLPAI

DPYPIKFFYNVSQIMLCAYMTIEACLLAYRNGYTIMPCVGYNRDDPAIGNLLWLFYVSKVWDFW

DTIFIVLGKKWRQLSFLHVYHHTTIFLFYWLNANVFYDGDIYLTIALNGFIHTVMYTYYFICMH

TKDKKTGKSLPIWWKSSLTLLQLFQFITMMSQGLYLIIFGCESLSIRVTATYVVYILSLFFLFA

QFFVASYMQPKKSKTA

Δ5-desurase from *Fragilariopsis cylindrus* nucleic acid
SEQ ID No. 21

1 ATGGCACCCGACGCCGATCACAAGCTGAGACAGCGCCGTCTAAAAGGCGACGAAGTTTGT

61 ATCGATGGAATTATCTATGATATATCATCCTTCGAGCATCCGGGTGGTGATACTATCAAC

121 GTATTTGGTGGAAACGATGCAACAATTCAGTACAAAATGATTCACCCGTACCATACCACG

181 AAGCATTTAGAAAAAATGAAGGTAGTTGGTAAAGTTCCAGACTACTACTCAGAATACAAA

241 TGGGATACACCCTTCGAACGTGAAATGAAACGTGAGGTATTTAAAATTGTACGACGTGGA

301 CAAGAATTTGGTACAAATGGATATTTTTTCCGTGCCATTTCGTATATTGCTATGTTTTTT

361 TATCTGCAATATTTATGGATGCAAGAATCTTCCTACACGTTAGCCATCGTATACGGGATT

421 AGTATGGGATTGATTGGACTGAATGTCCAGCATGATGCGAACCACGGAGCTGCATCGAAA

481 AAAGTGTGGGTGAATGACCTCCTAGGATTGGGAGCAGACTTTATCGGAGGATCGAAATGG

541 TTGTGGATGGAAAAACATTGGACGCATCATGCTTTTACAAACCATCGAGAAAAGGATCCA

601 GATGGGTTAGCAGCGGAACCTTTCCTATTGTTCAACGACTACGACTTGTCGAGTTCCAAA

661 CGTGCTGGATATCATGCATACCAAGGAATTTATTTAGTCCTATTATTGTGTGGGTATTGG

-continued

```
 721 CTTTCGGCAATTATTGATATACCTGTAATTTGGAATCTACAAGATCGTGGTGCCCTTACG
 781 GTAGGAATCCAGCTGGATAACGATTGGATTGCTAGTCGAAGAAAGTACGCGGTTAGTCTT
 841 CGAATCTTATACCTCTTTTGTAACATCGTCGTTCCTCTCTATAACAATTTCTCCTGGACA
 901 ACCGTGAGTCATATCAATGTAATGGGAATTTGTGGTAGCCTTACATTAGGACTACTTTTT
 961 ACCTTGTCGCACAATTTTGAGAATGTAGATCGAGATCCTACCAATCTGAACTTAAATGAA
1021 ACAGAAGAACCTGTTTGCTGGTTCAAATCTCAAGTAGAAACTTCTTCAACATACGGGGGC
1081 ATGATATCCGGATGGTTAACCGGCGGATTAAACTTTCAGGTTGAGCACCATTTATTCCCG
1141 AGAATGTCTAGTGCTTGGTATCCATTTATTGCACCAAAAGTTCGTGAAATTTGCAAAAAG
1201 CACGGAGTTCGTTACGTATACTATCCATGGTTGTTGCAAAATATGTATTCGACGTTGAAG
1261 TACACCCACGAGGTTGGTGTCGGCTCACATTGGAAGGATAATCCTTTTAAGGGTGAAATG
1321 TAG
```

Δ5-desurase from *Fragilariopsis cylindrus* amino acid

SEQ ID No. 22

```
  1 MAPDADHKLRQRRLKGDEVCIDGITYDISSFEHPGGDTINVFGGNDATIQYKMIHPYHTT
 61 KHLEKMKVVGKVPDYYSEYKWDTPFEREMKREVFKIVRRGQEFGTNGYFFRAISYIAMFF
121 YLQYLWMQESSYTLAIVYGISMGLIGLNVQHDANHGAASKKVWVNDLLGLGADFIGGSKW
181 LWMEKHWTHHAFTNHREKDPDGLAAEPFLLFNDYDLSSSKRAGYHAYQGIYLVLLLCGYW
241 LSAIIDIPVIWNLQDRGALTVGIQLDNDWIASRRKYAVSLRILYLFCNIVVPLYNNFSWT
301 TVSHINVMGICGSLTLGLLFTLSHNFENVDRDPTNLNLNETEEPVCWFKSQVETSSTYGG
361 MISGWLTGGLNFQVEHHLFPRMSSAWYPFIAPKVREICKKHGVRYVYYPWLLQNMYSTLK
421 YTHEVGVGSHWKDNPFKGEM-
```

*P. patens* PpHUP1L codon-optimised for expression in *Phaeodactylum tricornutum*

SEQ ID No. 23

```
   1 ATGGCAGGGGGGGTGTCGTTACGGCGGGGGAGATCAAGCACTACCCCGGCCGAACAACC
  61 TTCTTTGTGATTATGGTCTGTATAGTGGCGGCATCCGGAGGTCTCATGTTCGGATACGAT
 121 GTCGGAATTTCAGGGGGTGTCACGTCTATGGACGAATTTTTGGCGAAATTTTTTCCTGCG
 181 GTGTTGGCGAAGAAGCGAGCAGAGGCAGCTTCGGAGAGCGCCTACTGCAAGTATGATGAC
 241 CAGAAGCTGCAAGCCTTCACATCGTCGCTGTACATTTCCGCACTCGTGTCGACATTCTTC
 301 TCGTCGTACACCACCAGGCACTACGGCCGTAAATTTACCATGCTCATAGCTGGTTTCGCC
 361 TTCTGCTTCGGCGTCATCTTCACCGCCGCTGCGCAAGAAATCATCATGCTAATCATAGGG
 421 CGCGTCCTCCTGGGTTGGGGTGTCGGATTCGCTAACCAGGCTGTTCCGTTGTACCTCTCC
 481 GAAATGGCACCCTCCAAGTGGCGAGGTGCGCTCAACATCCTCTTCCAATTGGCGGTGACC
 541 ATTGGCATCCTGTTCGCCAGTCTCGTGAACTACGGCACAGAGAAGATGGCTCGCAACGGG
 601 TGGCGTGTTTCCCTCGCCATCGCCGGCCTGCCTGCGATCTTCATCACCCTCGGAGGATTA
 661 CTCCTGCCAGACACACCGAATTCCCTCGTGCAACGCGGCAAGCACGAGAGCGCCCGCCAG
 721 GTCCTACGCAGGATTCGTGGCGTCGACAACATTGAGGAAGAGTTCGACGACATCCTCATT
 781 GCCAGTAACGAAGCCGCCTCCGTGAAGCACCCCTTCCGCAATATCTTGAAACGCCGCAAC
 841 CGCCCTCAGCTGGTCATCTCCATGGCTCTTCAGTTTTTCCAGCAATTCACTGGAATTAAT
 901 GCTATTATGTTTTACGCGCCTGTCTTGTTCCAGACGCTGGGATTCGGGAGTTCCGCTTCA
 961 CTTTACTCTGCTGTCATCGTTGGAGCCGTGAATGTGCTGGCCACTTGCGTCGCTATCGCT
1021 GTTGTGGATCGATTCGGTCGACGATGGTTGCTCTTGGAAGCTTGCATCCAAATGTTCTTA
1081 GCACAGACGGCGATTGCAATTATCCTGGCGGCGGGATTGAAGGGGACCGAGATGCCGGAG
```

-continued

```
1141 TATCTGGGATGGATCGCGGTGGTATTGATTTGCGTGTACGTGTCTTCTTTCGCGTGGTCT

1201 TGGGGTCCACTTGGATGGTTGATTCCAAGTGAGATTTTCCCCTTGGAGACGCGTTCAGCA

1261 GGGCAAGCCATCACGGTGTCGACCAACATGGTCTTCACCTTCCTCATCGCGCAAGTGTTC

1321 CTGTCAATGTTGTGCGCGTTCAAGTGGGGCATCTTCCTCTTCTTCGCCGCGTGGGTGGTG

1381 GTGATGTTCCTTTTTACGTACTTTTTAATTCCCGAGACGAAGGGCATCCCCATCGAGGAG

1441 ATGGATCTCGTGTGGACCAAGCACTGGTTCTGGAAGCGCTACGTCCCCTACCCTGAGACT

1501 CTCGCTCACACCAGCGGCATCCCCATGGGAGATATGAAGGTCAGCAAGCTGGAGAATGGC

1561 TCCGCAAATGGCCACAAACTGTAA
```

Deduced polypeptide sequence of PpHUP1L

SEQ ID No. 24

```
  1 MAGGGVVTAGEIKHYPGRTTFFVIMVCIVAASGGLMFGYDVGISGGVTSMDEFLAKFFPA

61 VLAKKRAEAASESAYCKYDDQKLQAFTSSLYISALVSIFFSSYTTRHYGRKFTMLIAGFA

121 FCFGVIFTAAAQEIIMLIIGRVLLGWGVGFANQAVPLYLSEMAPSKWRGALNILFQLAVT

181 IGILFASLVNYGTEKMARNGWRVSLAIAGLPAIFITLGGLLLPDTPNSLVQRGKHESARQ

241 VLRRIRGVDNIEEEFDDILIASNEAASVKHPFRNILKRRNRPQLVISMALQFFQQFTGIN

301 AIMFYAPVLFQTLGFGSSASLYSAVIVGAVNVLATCVAIAVVDRFGRRWLLLEACIQMFL

361 AQTAIAIILAAGLKGTEMPEYLGWIAVVLICVYVSSFAWSWGPLGWLIPSEIFPLETRSA

421 GQAITVSTNMVFTFLIAQVFLSMLCAFKWGIFLFFAAWVVVMFLFTYFLIPETKGIPIEE

481 MDLVWTKHWFWKRYVPYPETLAHTSGIPMGDMKVSKLENGSANGHKL-
```

Homo sapiens HsGLUT1 codon-optimised for expression in Phaeodactylum tricornutum SEQ ID No. 25

```
   1 ATGGAGCCCAGCAGCAAGAAGCTGACGGGTCGCCTCATGCTGGCTGTGGGAGGAGCAGTG

61 CTTGGCTCCCTGCAGTTTGGCTACAACACTGGAGTCATCAATGCCCCCCAGAAGGTGATC

121 GAGGAGTTCTACAACCAGACATGGGTCCACCGCTATGGGGAGAGCATCCTGCCCACCACG

181 CTCACCACGCTCTGGTCCCTCTCAGTGGCCATCTTTTCTGTTGGGGGCATGATTGGCTCC

241 TTCTCTGTGGGCCTTTTCGTTAACCGCTTTGGCCGGCGGAATTCAATGCTGATGATGAAC

301 CTGCTGGCCTTCGTGTCCGCCGTGCTCATGGGCTTCTCGAAACTGGGCAAGTCCTTTGAG

361 ATGCTGATCCTGGGCCGCTTCATCATCGGTGTGTACTGCGGCCTGACCACAGGCTTCGTG

421 CCCATGTATGTGGGTGAAGTGTCACCCACAGCCTTTCGTGGGGCCCTGGGCACCCTGCAC

481 CAGCTGGGCATCGTCGTCGGCATCCTCATCGCCCAGGTGTTCGGCCTGGACTCCATCATG

541 GGCAACAAGGACCTGTGGCCCCTGCTGCTGAGCATCATCTTCATCCCGGCCCTGCTGCAG

601 TGCATCGTGCTGCCCTTCTGCCCCGAGAGTCCCCGCTTCCTGCTCATCAACCGCAACGAG

661 GAGAACCGGGCCAAGAGTGTGCTAAAGAAGCTGCGCGGGACAGCTGACGTGACCCATGAC

721 CTGCAGGAGATGAAGGAAGAGAGTCGGCAGATGATGCGGGAGAAGAAGGTCACCATCCTG

781 GAGCTGTTCCGCTCCCCCGCCTACCGCCAGCCCATCCTCATCGCTGTGGTGCTGCAGCTG

841 TCCCAGCAGCTGTCTGGCATCAACGCTGTCTTCTATTACTCCACGAGCATCTTCGAGAAG

901 GCGGGGGTGCAGCAGCCTGTGTATGCCACCATTGGCTCCGGTATCGTCAACACGGCCTTC

961 ACTGTCGTGTCGCTGTTTGTGGTGGAGCGAGCAGGCCGGCGGACCCTGCACCTCATAGGC

1021 CTCGCTGGCATGGCGGGTTGTGCCATACTCATGACCATCGCGCTAGCACTGCTGGAGCAG

1081 CTACCCTGGATGTCCTATCTGAGCATCGTGGCCATCTTTGGCTTTGTGGCCTTCTTTGAA

1141 GTGGGTCCTGGCCCCATCCCATGGTTCATCGTGGCTGAACTCTTCAGCCAGGGTCCACGT

1201 CCAGCTGCCATTGCCGTTGCAGGCTTCTCCAACTGGACCTCAAATTTCATTGTGGGCATG
```

```
1261 TGCTTCCAGTATGTGGAGCAACTGTGTGGTCCCTACGTCTTCATCATCTTCACTGTGCTC

1321 CTGGTTCTGTTCTTCATCTTCACCTACTTCAAAGTTCCTGAGACTAAAGGCCGGACCTTC

1381 GATGAGATCGCTTCCGGCTTCCGGCAGGGGGGAGCCAGCCAAAGTGATAAGACACCCGAG

1441 GAGCTGTTCCATCCCCTGGGGGCTGATTCCCAAGTGTGA
```

Deduced polypeptide sequence of HsGLUT1
SEQ ID No. 26

```
  1 MEPSSKKLTGRLMLAVGGAVLGSLQFGYNTGVINAPQKVIEEFYNQTWVHRYGESILPTT

61 LTTLWSLSVAIFSVGGMIGSFSVGLFVNRFGRRNSMLMMNLLAFVSAVLMGFSKLGKSFE

121 MLILGRFIIGVYCGLTTGFVPMYVGEVSPTAFRGALGTLHQLGIVVGILIAQVFGLDSIM

181 GNKDLWPLLLSIIFIPALLQCIVLPFCPESPRFLLINRNEENRAKSVLKKLRGTADVIHD

241 LQEMKEESRQMMREKKVTILELFRSPAYRQPILIAVVLQLSQQLSGINAVFYYSTSIFEK

301 AGVQQPVYATIGSGIVNTAFTVVSLFVVERAGRRTLHLIGLAGMAGCAILMTIALALLEQ

361 LPWMSYLSIVAIFGFVAFFEVGPGPIPWFIVAELFSQGPRPAAIAVAGFSNWTSNFIVGM

421 CFQYVEQLCGPYVFIIFTVLLVLFFIFTYFKVPETKGRTFDEIASGFRQGGASQSDKTPE

481 ELFHPLGADSQV-
```

---

The invention claimed is:

1. A transgenic microalgae with increased production of at least one omega-3 long chain polyunsaturated fatty acid (LC-PUFA) compared to a control microalgae,
wherein the transgenic microalgae overexpresses a nucleic acid encoding a Δ5-elongase and/or Δ6-desaturase, wherein the nucleic acid encoding the Δ5-elongase is selected from SEQ ID NO:1 and a sequence that encodes a Δ5-elongase that has at least 75% homology to SEQ ID NO:2, and wherein the nucleic acid encoding a Δ6-desaturase is selected from SEQ ID NO:3; a sequence that encodes a Δ6-desaturase that has at least 75% homology to SEQ ID NO:4; SEQ ID NO:5; SEQ ID NO:7; a sequence that encodes a Δ6-desaturase that has at least 75% homology to SEQ ID NO:8; SEQ NO:9 and a sequence that encodes a Δ6-desaturase that has at least 75% homology to SEQ ID NO:10;
wherein the omega-3 LC-PUFA is EPA and/or DHA, and wherein, when the omega-3 LC-PUFA is EPA, the increase is to at least 20% of the total fatty acid content, and when the omega-3 LC-PUFA is DHA, the increase is to at least 7% of the total fatty acid content; and
wherein the transgenic microalgae is selected from *Phaeodactylum*, *Nannochloropsis*, *Thraustochytrium*, *Schizochytrium*, or *Thalassiosira*.

2. A transgenic microalgae of claim 1, wherein the nucleic acid further comprises a regulatory sequence.

3. A method for producing transgenic microalgae with an increased omega-3 LC-PUFA content compared to a control microalgae, the method comprising transforming a microalgae with a nucleic acid encoding a Δ5-elongase in order to increase the content of DHA or a nucleic acid encoding Δ6-desaturase in order to increase the content of EPA, wherein said nucleic acid encoding a Δ5-elongase is selected from SEQ ID NO:1 and a sequence that encodes a Δ5-elongase that has at least 75% homology to SEQ ID NO:2, and wherein the nucleic acid encoding a Δ6-desaturase is selected from SEQ NO:3; a sequence that encodes a Δ6-desaturase that has at least 75% homology to SEQ ID NO:4; SEQ ID NO:5; SEQ ID NO:7; a sequence that encodes a Δ6-desaturase that has at least 75% homology to SEQ ID NO:8; SEQ ID NO:9 and a sequence that encodes a Δ6-desaturase that has at least 75% homology to SEQ ID NO:10.

4. A method for increasing production of one or more omega-3 LC-PUFAs in microalgae, the method comprising
a) cultivating a transgenic microalgae of claim 1 under conditions which allow for the production of one or more omega-3 LC-PUFAs and
b) obtaining the one or more omega-3 LC-PUFAs from the transgenic microalgae.

5. A method of claim 4, wherein the omega-3 LC-PUFA is DHA.

6. A method of claim 4, wherein the omega-3 LC-PUFA is EPA.

7. A composition comprising a transgenic microalgae of claim 1.

8. A method for making a feedstuff, the method comprising
a) cultivating a transgenic microalgae of claim 1 under conditions allow for the production of one or more omega-3 LC-PUFAs;
b) obtaining one or more omega-3 LC-PUFAs from the transgenic microalgae; and
c) making a feedstuff from the one or more omega-3 LC-PUFAs.

9. The transgenic microalgae of claim 1, wherein the control microalgae has not been genetically modified to alter the content of omega-3 LC-PUFAs therein.

10. The transgenic microalgae of claim 1, wherein the transgenic microalgae is *Phaeodactylum*.

11. The transgenic microalgae of claim 1, wherein the omega-3 LC-PUFA is DHA and wherein the increase to at least 10% of the total fatty acid content is in the stationary phase.

12. The transgenic microalgae of claim 1, wherein the omega-3 LC-PUFA is EPA and wherein the increase to at least 20% of the total fatty acid content is in the stationary phase.

\* \* \* \* \*

SEQUENCE LISTING

<160> NUMBER OF SEQ ID NOS: 26

<210> SEQ ID NO 1
<211> LENGTH: 903
<212> TYPE: DNA
<213> ORGANISM: Ostreococcus tauri

<400> SEQUENCE: 1

```
atgagcgcct ccggtgcgct gctgcccgcg atcgcgtccg ccgcgtacgc gtacgcgacg      60
tacgcctacg cctttgagtg gtcgcacgcg aatggcatcg acaacgtcga cgcgcgcgag     120
tggatcggtg cgctgtcgtt gaggctcccg gcgatcgcga cgacgatgta cctgttgttc     180
tgcctggtcg gaccgaggtt gatggcgaag gcgaggcgt tcgacccgaa ggggttcatg      240
ctggcgtaca atgcgtatca gacggcgttc aacgtcgtcg tgctcgggat gttcgcgcga     300
gagatctcgg ggctggggca gcccgtgtgg gggtcaacca tgccgtggag cgatagaaaa     360
tcgtttaaga tcctcctcgg ggtgtggttg cactacaaca caaatatttt ggagctattg     420
gacactgtgt tcatggttgc gcgcaagaag acgaagcagt tgagcttctt gcacgtttat     480
catcacgccc tgttgatctg ggcgtggtgg ttggtgtgtc acttgatggc cacgaacgat     540
tgtatcgatg cctacttcgg cgcggcgtgc aactcgttca ttcacatcgt gatgtactcg     600
tattatctca tgtcggcgct cggcattcga tgcccgtgga agcgatacat cacccaggct     660
caaatgctcc aattcgtcat tgtcttcgcg cacgccgtgt tcgtgctgcg tcagaagcac     720
tgcccggtca cccttccttg ggcgcaaatg ttcgtcatga cgaacatgct cgtgctcttc     780
gggaacttct acctcaaggc gtactcgaac aagtcgcgcg cgacggcgc gagttccgtg      840 aaaccagccg agaccacgcg cgcgcccagc gtgcgacgca cgcgatctcg aaaaattgac     900
taa                                                                   903
```

<210> SEQ ID NO 2
<211> LENGTH: 300
<212> TYPE: PRT
<213> ORGANISM: Ostreococcus tauri

<400> SEQUENCE: 2

```
Met Ser Ala Ser Gly Ala Leu Leu Pro Ala Ile Ala Ser Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
                100                 105                 110

Thr Met Pro Trp Ser Asp Arg Lys Ser Phe Lys Ile Leu Leu Gly Val
            115                 120                 125

Trp Leu His Tyr Asn Asn Lys Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
        275                 280                 285

Pro Ser Val Arg Arg Thr Arg Ser Arg Lys Ile Asp
    290                 295                 300
```

<210> SEQ ID NO 3
<211> LENGTH: 1371
<212> TYPE: DNA
<213> ORGANISM: Ostreococcus tauri

<400> SEQUENCE: 3

```
atgtgcgtgg agacggaaaa taacgatggg atccccacgg tggagatcgc gttcgacggt      60
gagcgcgagc gggcggaggc aaacgtgaag ctgtccgcgg agaagatgga gccgcggcg     120 ctggcgaaga cgttcgcgag gcggtacgtc gtgatcgagg gggtggagta cgatgtgacg    180
gattttaagc acccgggagg aacggttatt ttctatgcgt tgtcaaacac cggggcggac    240
gcgacggaag cgttcaagga gtttcatcat cggtcgagaa aggcgaggaa agccttggcg    300
gcgctcccgt ctcgaccggc caagacggcc aaggtggacg acgcggagat gctccaagat    360
```

```
ttcgccaagt ggcggaaaga attggagaga gatggattct tcaagccctc tccggcgcac     420
gtggcgtatc gcttcgccga gctcgcggcg atgtacgctc tcgggacgta cctgatgtac     480
gctcgatacg tcgtctcctc ggtgctcgtg tacgcttgct ttttcggcgc ccgatgcggt     540
tgggtgcagc acgagggcgg acacagctcg ctgacgggca acatttggtg ggacaagcgc     600
atccaggcct tcacagccgg gttcggtctc gccggtagcg gcgacatgtg aactcgatg      660 cacaacaagc atcacgcgac gcctcaaaag gttcgtcacg acatggatct ggacaccacc     720
cccgcggtgg cgttcttcaa caccgcggtg gaagacaatc gtccccgtgg ctttagcaag     780
tactggttgc gccttcaggc gtggaccttc atccccgtga cgtccggctt ggtgctcctt     840
ttctggatgt ttttcctcca cccctccaag gctttgaagg gtggcaagta cgaagagttg     900
gtgtggatgc tcgccgcgca cgtcatccgc acgtggacga tcaaggcggt gaccggattc     960
accgcgatgc agtcctacgg cttattttg gcgacgagct gggtgagcgg ctgctatctg    1020
tttgcacact tctccacgtc gcacacgcac ctggatgtgg tgcccgcgga cgagcatctc    1080
tcctgggttc gatacgccgt cgatcacacg atcgacatcg atccgagtca aggttgggtg    1140
aactggttga tgggctacct caactgccaa gtcatccacc acctctttcc gagcatgccg    1200
cagttccgcc agcccgaggt atctcgccgc ttcgtcgcct ttgcgaaaaa gtggaacctc    1260
aactacaagg tcatgaccta cgccggtgcg tggaaggcaa cgctcggaaa cctcgacaac    1320
gtgggtaagc actactacgt gcacggccaa cactccggaa agacggcgta a             1371
```

<210> SEQ ID NO 4
<211> LENGTH: 456
<212> TYPE: PRT
<213> ORGANISM: Ostreococcus tauri

<400> SEQUENCE: 4

```
Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
                20                  25                  30

Ala Glu Lys Met Glu Pro Ala Ala Leu Ala Lys Thr Phe Ala Arg Arg
            35                  40                  45

Tyr Val Ile Glu Gly Val Glu Tyr Asp Val Thr Asp Phe Lys His
        50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190
```

-continued

```
Gly Asn Ile Trp Trp Asp Lys Arg Ile Gln Ala Phe Thr Ala Gly Phe
            195                 200                 205
Gly Leu Ala Gly Ser Gly Asp Met Trp Asn Ser Met His Asn Lys His
        210                 215                 220
His Ala Thr Pro Gln Lys Val Arg His Asp Met Asp Leu Asp Thr Thr
225                 230                 235                 240
Pro Ala Val Ala Phe Phe Asn Thr Ala Val Glu Asp Asn Arg Pro Arg
                245                 250                 255
Gly Phe Ser Lys Tyr Trp Leu Arg Leu Gln Ala Trp Thr Phe Ile Pro
            260                 265                 270
Val Thr Ser Gly Leu Val Leu Leu Phe Trp Met Phe Phe Leu His Pro
        275                 280                 285
Ser Lys Ala Leu Lys Gly Gly Lys Tyr Glu Glu Leu Val Trp Met Leu
    290                 295                 300
Ala Ala His Val Ile Arg Thr Trp Thr Ile Lys Ala Val Thr Gly Phe
305                 310                 315                 320
Thr Ala Met Gln Ser Tyr Gly Leu Phe Leu Ala Thr Ser Trp Val Ser
                325                 330                 335
Gly Cys Tyr Leu Phe Ala His Phe Ser Thr Ser His Thr His Leu Asp
            340                 345                 350
Val Val Pro Ala Asp Glu His Leu Ser Trp Val Arg Tyr Ala Val Asp
        355                 360                 365
His Thr Ile Asp Ile Asp Pro Ser Gln Gly Trp Val Asn Trp Leu Met
    370                 375                 380
Gly Tyr Leu Asn Cys Gln Val Ile His His Leu Phe Pro Ser Met Pro
385                 390                 395                 400
Gln Phe Arg Gln Pro Glu Val Ser Arg Arg Phe Val Ala Phe Ala Lys
                405                 410                 415
Lys Trp Asn Leu Asn Tyr Lys Val Met Thr Tyr Ala Gly Ala Trp Lys
            420                 425                 430
Ala Thr Leu Gly Asn Leu Asp Asn Val Gly Lys His Tyr Tyr Val His
        435                 440                 445
Gly Gln His Ser Gly Lys Thr Ala
    450                 455

<210> SEQ ID NO 5
<211> LENGTH: 1413
<212> TYPE: DNA
<213> ORGANISM: Ostreococcus tauri

<400> SEQUENCE: 5
ggtaccaagc ttgatatcac caaaatgtgt gtcgaaacgg aaaacaacga tggaatcccc      60
acggtcgaaa ttgcctttga tggagaacgc gaacgcgccg aagccaacgt caagctctcc     120
gccgaaaaga tggaacccgc cgccttggcc aagaccttcg cccgtcgcta cgtcgtcatt     180
gaaggtgtcg aatacgatgt caccgacttc aagcacccgg aggtacggt catcttttac      240
gccctctcca caccggagc cgacgccacg gaagccttca aggaatttca ccaccgttcc      300
cgcaaggccc gtaaggccct cgccgccttg ccctcgcgcc cggccaagac cgccaaggtc     360
gacgatgccg aaatgcttca ggatttcgcc aagtggcgta aggaactcga acgcgacggc     420
ttctttaagc cctccccggc ccacgtcgcc taccgttttg ccgaactcgc cgccatgtac     480
gcccttggaa cctacctcat gtacgcccgt tacgtcgtct cctcggtctt ggtctacgcc     540
tgcttctttg gtgcccgctg tggatgggtc cagcacgaag gcggacactc ctcgctcacc     600
```

```
ggaaacattt ggtgggataa gcgtatccaa gccttcacgg ccggatttgg tttggccggc    660
tccggagaca tgtggaactc gatgcacaac aagcaccacg ccaccccca gaaggtccgt     720
cacgacatgg atctcgacac cacgccggcc gtcgccttct taacaccgc cgtcgaagat    780
aaccgtcccc gcggattctc caagtactgg cttcgtctcc aagcctggac cttcattccc    840
gtcacgtccg gtttggtcct cttgttttgg atgttctttc ttcacccgtc gaaggccctc    900
aagggtggca agtacgaaga attggtctgg atgcttgccg cccacgtcat tcgtacctgg    960
acgatcaagg ccgtcaccgg tttcacggcc atgcagtcct acggcttgtt cttgccacc    1020
tcctgggtct cggggttgcta cctcttcgcc cactttttcca cctcgcacac gcacttggat   1080
gtcgtccccg ccgacgaaca cctttcctgg gtccgctacg ccgtcgacca caccattgac    1140
attgacccgt cgcagggatg ggtcaactgg ctcatgggtt acttgaactg tcaagtcatc    1200
caccacctct tccctccat gccgcagttt cgtcaacccg aagtctcgcg tcgcttcgtc    1260
gcctttgcca agaagtggaa cttgaactac aaggtcatga cctacgccgg agcctggaag    1320
gccacgcttg gaaaccttga taacgtcgga aagcactact acgtccacgg ccagcactcg    1380
ggaaagaccg cctaagagct cggtaccctc gag                                  1413
```

<210> SEQ ID NO 6
<211> LENGTH: 456
<212> TYPE: PRT
<213> ORGANISM: Ostreococcus tauri

<400> SEQUENCE: 6

```
Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
```

```
                225                 230                 235                 240
Pro Ala Val Ala Phe Phe Asn Thr Ala Val Glu Asp Asn Arg Pro Arg
                    245                 250                 255
Gly Phe Ser Lys Tyr Trp Leu Arg Leu Gln Ala Trp Thr Phe Ile Pro
                260                 265                 270
Val Thr Ser Gly Leu Val Leu Phe Trp Met Phe Phe Leu His Pro
            275                 280                 285
Ser Lys Ala Leu Lys Gly Gly Lys Tyr Glu Glu Leu Val Trp Met Leu
        290                 295                 300
Ala Ala His Val Ile Arg Thr Trp Thr Ile Lys Ala Val Thr Gly Phe
305                 310                 315                 320
Thr Ala Met Gln Ser Tyr Gly Leu Phe Leu Ala Thr Ser Trp Val Ser
                325                 330                 335
Gly Cys Tyr Leu Phe Ala His Phe Ser Thr Ser His Thr His Leu Asp
                340                 345                 350
Val Val Pro Ala Asp Glu His Leu Ser Trp Val Arg Tyr Ala Val Asp
            355                 360                 365
His Thr Ile Asp Ile Asp Pro Ser Gln Gly Trp Val Asn Trp Leu Met
370                 375                 380
Gly Tyr Leu Asn Cys Gln Val Ile His His Leu Phe Pro Ser Met Pro
385                 390                 395                 400
Gln Phe Arg Gln Pro Glu Val Ser Arg Arg Phe Val Ala Phe Ala Lys
                405                 410                 415
Lys Trp Asn Leu Asn Tyr Lys Val Met Thr Tyr Ala Gly Ala Trp Lys
                420                 425                 430
Ala Thr Leu Gly Asn Leu Asp Asn Val Gly Lys His Tyr Tyr Val His
            435                 440                 445
Gly Gln His Ser Gly Lys Thr Ala
        450                 455

<210> SEQ ID NO 7
<211> LENGTH: 1386
<212> TYPE: DNA
<213> ORGANISM: Ostreococcus RCC809

<400> SEQUENCE: 7
atgcgcgtcg aaacggagga cgacaacgtt ccgacggtca ccgtcggact gtcggaggag    60
agcgacggga tgaaggggc gagaaacccc ggggcgcggg cgtggaaatc gacgctcgag   120
ccgcacgcgt tggccaagtc gttcgatcga cggtgggtca aggttgacgg cgtcgagtac   180
gacgtcacgg attttaagca tccgggtgga tctgtgattt attacatgct gtcgaacacc   240
ggagcggacg cgacggaggc gttcaaagag tttcattatc ggtcgaaaaa ggcgagaaag   300
gcgttggcgg cgttgccgca gcgcgagccg gaggacgcgt cgccagtgga agacgcgaat   360
atgttgaagg atttcgcgaa atggcgcaaa gatttggagc gcgagggttt ctttaaaccg   420
tcgccggcgc acgtggcgta cagattcgcg gaactcgcgg ccatgttcgc gctcgggacg   480
gcgttgatgt acgctcgatg gcacgccacc tcagtcttcg tcaccgcgtg cttttttcggc   540 gcgcggtgcg gttgggtgca acacgagggt ggtcacagct cgctgacggg gagcattttgg   600 tgggacaagc gaatccaagc gttcaccgcc ggtttcggat agcatcgag cggcgacatg   660 tggaacctca tgcacaacaa gcaccacgcc actccgcaaa aggtgcgaca cgacatggac   720
ctcgacacca cgccggcggt ggccttcttc aacactgcgg tcgaggaaaa ccgtccgcgc   780
aagttcagta agttatggtt gcgcgtgcag gcgtggacgt tcgtcccggt cacctctggt   840
```

```
ttggtgttgc tcgcctggat gtacctcttg catccgagac acattgctcg ccgtaaaaac      900
tacgaagagg ctgcgtggat cgtcgccgcg cacgtcatcc gcacgtcggt catcaaagcc      960
gtgaccggtt actcctggat cacgtgctac ggtttgttct tgtccaccat gtgggtgagc     1020
ggctgctacc tctttgcgca cttctccacg tctcacacgc acctcgacgt cgttccgagc     1080
gataagcatc tctcttgggt gcgatacgcc gtcgaccaca ccatcgacat cgacccgagc     1140
aagagcgtcg tcaactggtt gatgggttac ctgaactgcc aggtcatcca tcacttgttt     1200
ccggacatgc tcagttccg tcagcccgaa gtctctcgcc gcttcgtctc ctttgcgaaa      1260
aagtggaacc tcaattacaa ggtcatgagc tactacggcg cgtggaaggc caccttcggt     1320
aacttgaacg aggtcggcaa gcactattac atccaaggtt ctcaaatcac gaagaagacg     1380
gtgtaa                                                                1386
```

<210> SEQ ID NO 8
<211> LENGTH: 461
<212> TYPE: PRT
<213> ORGANISM: Ostreococcus RCC809

<400> SEQUENCE: 8

```
Met Arg Val Glu Thr Glu Asp Asp Asn Val Pro Thr Val Thr Val Gly
1               5                   10                  15

Leu Ser Glu Glu Ser Asp Gly Met Lys Gly Ala Arg Asn Pro Gly Ala
            20                  25                  30

Arg Ala Trp Lys Ser Thr Leu Glu Pro His Ala Val Ala Lys Ser Phe
        35                  40                  45

Asp Arg Arg Trp Val Lys Val Asp Gly Val Glu Tyr Asp Val Thr Asp
    50                  55                  60

Phe Lys His Pro Gly Gly Ser Val Ile Tyr Tyr Met Leu Ser Asn Thr
65                  70                  75                  80

Gly Ala Asp Ala Thr Glu Ala Phe Lys Glu Phe His Tyr Arg Ser Lys
                85                  90                  95

Lys Ala Arg Lys Ala Leu Ala Ala Leu Pro Gln Arg Glu Pro Glu Asp
            100                 105                 110

Ala Ser Pro Val Glu Asp Ala Asn Met Leu Lys Asp Phe Ala Lys Trp
        115                 120                 125

Arg Lys Asp Leu Glu Arg Glu Gly Phe Phe Lys Pro Ser Pro Ala His
    130                 135                 140

Val Ala Tyr Arg Phe Ala Glu Leu Ala Ala Met Phe Ala Leu Gly Thr
145                 150                 155                 160

Ala Leu Met Tyr Ala Arg Trp His Ala Thr Ser Val Phe Val Thr Ala
                165                 170                 175

Cys Phe Phe Gly Ala Arg Cys Gly Trp Val Gln His Glu Gly Gly His
            180                 185                 190

Ser Ser Leu Thr Gly Ser Ile Trp Trp Asp Lys Arg Ile Gln Ala Phe
        195                 200                 205

Thr Ala Gly Phe Gly Leu Ala Ser Ser Gly Asp Met Trp Asn Leu Met
    210                 215                 220

His Asn Lys His His Ala Thr Pro Gln Lys Val Arg His Asp Met Asp
225                 230                 235                 240

Leu Asp Thr Thr Pro Ala Val Ala Phe Phe Asn Thr Ala Val Glu Glu
                245                 250                 255

Asn Arg Pro Arg Lys Phe Ser Lys Leu Trp Leu Arg Val Gln Ala Trp
            260                 265                 270
```

```
Thr Phe Val Pro Val Thr Ser Gly Leu Val Leu Ala Trp Met Tyr
        275                 280                 285
Leu Leu His Pro Arg His Ile Ala Arg Arg Lys Asn Tyr Glu Glu Ala
        290                 295                 300
Ala Trp Ile Val Ala Ala His Val Ile Arg Thr Ser Val Ile Lys Ala
305                 310                 315                 320
Val Thr Gly Tyr Ser Trp Ile Thr Cys Tyr Gly Leu Phe Leu Ser Thr
                325                 330                 335
Met Trp Val Ser Gly Cys Tyr Leu Phe Ala His Phe Ser Thr Ser His
        340                 345                 350
Thr His Leu Asp Val Val Pro Ser Asp Lys His Leu Ser Trp Val Arg
        355                 360                 365
Tyr Ala Val Asp His Thr Ile Asp Ile Asp Pro Ser Lys Ser Val Val
        370                 375                 380
Asn Trp Leu Met Gly Tyr Leu Asn Cys Gln Val Ile His His Leu Phe
385                 390                 395                 400
Pro Asp Met Pro Gln Phe Arg Gln Pro Glu Val Ser Arg Arg Phe Val
                405                 410                 415
Ser Phe Ala Lys Lys Trp Asn Leu Asn Tyr Lys Val Met Ser Tyr Tyr
        420                 425                 430
Gly Ala Trp Lys Ala Thr Phe Gly Asn Leu Asn Glu Val Gly Lys His
        435                 440                 445
Tyr Tyr Ile Gln Gly Ser Gln Ile Thr Lys Lys Thr Val
        450                 455                 460
```

<210> SEQ ID NO 9
<211> LENGTH: 1386
<212> TYPE: DNA
<213> ORGANISM: Ostreococcus RCC809

<400> SEQUENCE: 9

```
atgcgtgtgg aaaccgaaga cgataatgtg ccaactgtta ctgtgggatt gtcagaggag     60
tccgatggaa tgaagggagc aaggaacccc ggagcacgtg cttggaagtc gacgttggag    120
ccgcacgccg tggcaaagtc attcgatcgt aggtgggtta aggttgacgg agtcgaatac    180
gacgtaactg atttcaagca tcccggagga tcagttatct actatatgct ttctaacacc    240
ggagctgatg ccactgaggc tttcaaggaa tttcactatc gtagtaagaa ggccaggaag    300
gcacttgctg ccctcccaca acgtgagcct gaagacgctt cgccagtcga ggatgccaat    360
atgctcaagg acttcgcaaa gtggcgtaag gatttggaga gggaaggatt ctttaagcca    420
agtcctgctc acgtggccta ccgtttcgcc gaactcgcag ctatgtttgc tttgggaact    480
gcccttatgt atgcacgttg gcatgctacg tctgtcttcg taacagcctg tttctttgga    540
gcaaggtgtg gatgggtgca acacgaggga ggacattctt ccttgaccgg atccatctgg    600
tgggataagc gtattcaggc attcactgct ggatttggac ttgccagttc gggagacatg    660
tggaacctca tgcacaataa gcaccatgca acgccacaaa agttaggca tgatatggac    720
ctcgatacca ctcctgcagt ggctttcttt aacacagctg ttgaggaaaa tcgtcctagg    780
aagttctcta agttgtggct tcgtgtccag gcctggacct ttgtgcccgt acttccggaa    840
ttggtactct tggcatggat gtaccttctc cacccgcgtc atatcgctcg taggaagaac    900
tatgaggaag ccgcatggat tgtggctgcc catgttatca ggacctccgt cattaaggct    960
gtaacgggat acagttggat cacatgttat ggactcttct tgtcgactat gtgggtctca   1020
```

```
ggatgctacc tcttcgctca cttttcaacg tctcacacac atttggacgt ggttccatct    1080
gataagcacc tttcctgggt gcgttacgcc gttgatcata ccatcgacat tgatccttcc    1140
aagagtgtcg taaactggct catgggatat ttgaactgtc aggttatcca ccatttgttc    1200
cccgacatgc cgcaatttcg tcagcccgaa gtcagtcgta ggttcgtatc gtttgccaag    1260
aagtggaacc ttaattacaa ggtcatgtct tactatggag cctggaaggc aaccttcgga    1320
aatctcaacg aagtcggaaa gcactactac atccaaggaa gtcaaatcac aaagaagacg    1380
gtttag                                                                1386
```

<210> SEQ ID NO 10
<211> LENGTH: 461
<212> TYPE: PRT
<213> ORGANISM: Ostreococcus RCC809

<400> SEQUENCE: 10

```
Met Arg Val Glu Thr Glu Asp Asn Val Pro Thr Val Thr Val Gly
1               5                   10                  15

Leu Ser Glu Glu Ser Asp Gly Met Lys Gly Ala Arg Asn Pro Gly Ala
            20                  25                  30

Arg Ala Trp Lys Ser Thr Leu Glu Pro His Ala Val Ala Lys Ser Phe
        35                  40                  45

Asp Arg Arg Trp Val Lys Val Asp Gly Val Glu Tyr Asp Val Thr Asp
    50                  55                  60

Phe Lys His Pro Gly Gly Ser Val Ile Tyr Tyr Met Leu Ser Asn Thr
65                  70                  75                  80

Gly Ala Asp Ala Thr Glu Ala Phe Lys Glu Phe His Tyr Arg Ser Lys
                85                  90                  95

Lys Ala Arg Lys Ala Leu Ala Ala Leu Pro Gln Arg Glu Pro Glu Asp
            100                 105                 110

Ala Ser Pro Val Glu Asp Ala Asn Met Leu Lys Asp Phe Ala Lys Trp
        115                 120                 125

Arg Lys Asp Leu Glu Arg Glu Gly Phe Phe Lys Pro Ser Pro Ala His
    130                 135                 140

Val Ala Tyr Arg Phe Ala Glu Leu Ala Ala Met Phe Ala Leu Gly Thr
145                 150                 155                 160

Ala Leu Met Tyr Ala Arg Trp His Ala Thr Ser Val Phe Val Thr Ala
                165                 170                 175

Cys Phe Phe Gly Ala Arg Cys Gly Trp Val Gln His Glu Gly Gly His
            180                 185                 190

Ser Ser Leu Thr Gly Ser Ile Trp Trp Asp Lys Arg Ile Gln Ala Phe
        195                 200                 205

Thr Ala Gly Phe Gly Leu Ala Ser Ser Gly Asp Met Trp Asn Leu Met
    210                 215                 220

His Asn Lys His His Ala Thr Pro Gln Lys Val Arg His Asp Met Asp
225                 230                 235                 240

Leu Asp Thr Thr Pro Ala Val Ala Phe Phe Asn Thr Ala Val Glu Glu
                245                 250                 255

Asn Arg Pro Arg Lys Phe Ser Lys Leu Trp Leu Arg Val Gln Ala Trp
            260                 265                 270

Thr Phe Val Pro Val Thr Ser Gly Leu Val Leu Leu Ala Trp Met Tyr
        275                 280                 285

Leu Leu His Pro Arg His Ile Ala Arg Arg Lys Asn Tyr Glu Glu Ala
    290                 295                 300
```

```
Ala Trp Ile Val Ala Ala His Val Ile Arg Thr Ser Val Ile Lys Ala
305                 310                 315                 320

Val Thr Gly Tyr Ser Trp Ile Thr Cys Tyr Gly Leu Phe Leu Ser Thr
            325                 330                 335

Met Trp Val Ser Gly Cys Tyr Leu Phe Ala His Phe Ser Thr Ser His
            340                 345                 350

Thr His Leu Asp Val Val Pro Ser Asp Lys His Leu Ser Trp Val Arg
        355                 360                 365

Tyr Ala Val Asp His Thr Ile Asp Ile Asp Pro Ser Lys Ser Val Val
    370                 375                 380

Asn Trp Leu Met Gly Tyr Leu Asn Cys Gln Val Ile His His Leu Phe
385                 390                 395                 400

Pro Asp Met Pro Gln Phe Arg Gln Pro Glu Val Ser Arg Arg Phe Val
            405                 410                 415

Ser Phe Ala Lys Lys Trp Asn Leu Asn Tyr Lys Val Met Ser Tyr Tyr
            420                 425                 430

Gly Ala Trp Lys Ala Thr Phe Gly Asn Leu Asn Glu Val Gly Lys His
            435                 440                 445

Tyr Tyr Ile Gln Gly Ser Gln Ile Thr Lys Lys Thr Val
    450                 455                 460
```

<210> SEQ ID NO 11
<211> LENGTH: 1278
<212> TYPE: DNA
<213> ORGANISM: Emiliania huxleyi

<400> SEQUENCE: 11

```
atgggaggcg ccggcgcgag cgaggctgaa cggcccaagt ggaccacgat ccacgggcgg      60
cacgtcgatg tgtcaaagtt ccgccacccg ggtgggaaca tcatcgagct cttctatggc     120
atggactcga cgagcgcgtt cgagcagttc cacggccacc acaagggcgc gtggaagatg     180
ctcaaggcgc tgccgaccaa ggaggtcgac ccgccgacg tgccgcagca gccgcaggag      240
cacgttgccg agatgacgcg gctgatgacg tcgtggcgcg agcgcggcct ctttaagccg     300
cgccccgtcg cctcgggcat ctacggtctc gccgtcgtcg ctgccatcgt cgcgtgcatc     360
gcctgcgcgc cgcacgcgcc ggtgctgagc gggatcgggc tcggcagctg ctgggcgcag     420
tgcggcttcc tgcagcacat gggcgggcac cgcgagtggg gggtgcggta ctccttcctc     480
ctgcagcact tcttcgaggg cctcctcaag gcgggtccg cctcgtggtg cgcaaccgc       540
cacaacaagc atcacgcaaa gactaacgtg ctcggcgagg acggcgacct gcggacgact     600
cccttcttcg cctgggaccc gacgctcgcc aagaaggttc cagactggtc gctcaagacg     660
caggccttca ccttcctccc cgccctcgga gcgtacgtct ttgtctttgc cttcacgatc     720
cgcaagtatg ccgtcgtcaa gaagctctgg cacgagctcg cactcatgat cgcgcactac     780
gcgatgttct actacgcgct gcagctcgcc ggtgcgtcgc tcggcagcgg cctcgccttt     840
tactgcaccg gctacgcctg gcaaggcatc tacctcggct tcttcttcgg cctgtcccac     900
ttcgcggtcg agcgagtccc ctccaccgcc acctggctcg agtcgtccat gatcggcacc     960
gtcgactggg gaggctcctc cgccttttgc ggctacgtct ccggcttcct caacatccag    1020
atcgagcacc acatggcgcc gcagatgccg atggagaacc tgcgccagat ccgcgccgac    1080
tgcaaggcga gcgcggagaa gctcgggctt ccctatcgcg agctctcctt cgccggcgcg    1140
gtcaagctga tgatggtcgg cctctggcgc acggggaggg acgagctgca gctgcgctcc    1200
gacaggcgca agtactcgcg cacccaggcc tacatggcgg ccgcctcggc ggtggtggag    1260
```
aacctcaagg cggactag                                    1278

<210> SEQ ID NO 12
<211> LENGTH: 550
<212> TYPE: PRT
<213> ORGANISM: Emiliania huxleyi

<400> SEQUENCE: 12

| | | | | | | | | | | | | | | |
|---|---|---|---|---|---|---|---|---|---|---|---|---|---|---|
| Met | Gly | Asn | Gly | Asn | Leu | Pro | Ala | Ser | Thr | Ala | Gln | Leu | Lys | Ser | Thr |
| 1 | | | | 5 | | | | | 10 | | | | | 15 | |
| Ser | Lys | Pro | Gln | Gln | Gln | His | Glu | His | Arg | Thr | Ile | Ser | Lys | Ser | Glu |
| | | | 20 | | | | | 25 | | | | | 30 | | |
| Leu | Ala | Gln | His | Asn | Thr | Pro | Lys | Ser | Ala | Trp | Cys | Ala | Val | His | Ser |
| | | | | 35 | | | | | 40 | | | | | 45 | |
| Thr | Pro | Ala | Thr | Asp | Pro | Ser | His | Ser | Asn | Asn | Lys | Gln | His | Ala | His |
| | 50 | | | | | 55 | | | | | 60 | | | | |
| Leu | Val | Leu | Asp | Ile | Thr | Asp | Phe | Ala | Ser | Arg | His | Pro | Gly | Gly | Asp |
| 65 | | | | | 70 | | | | | 75 | | | | | 80 |
| Leu | Ile | Leu | Leu | Ala | Ser | Gly | Lys | Asp | Ala | Ser | Val | Leu | Phe | Glu | Thr |
| | | | | 85 | | | | | 90 | | | | | 95 | |
| Tyr | His | Pro | Arg | Gly | Val | Pro | Thr | Ser | Leu | Ile | Gln | Lys | Leu | Gln | Ile |
| | | | | 100 | | | | | 105 | | | | | 110 | |
| Gly | Val | Met | Glu | Glu | Ala | Phe | Arg | Asp | Ser | Phe | Tyr | Ser | Trp | Thr | |
| | | | 115 | | | | | 120 | | | | | 125 | | |
| Asp | Ser | Asp | Phe | Tyr | Thr | Val | Leu | Lys | Arg | Arg | Val | Glu | Arg | Leu | |
| | 130 | | | | | 135 | | | | | 140 | | | | |
| Glu | Glu | Arg | Gly | Leu | Asp | Arg | Arg | Gly | Ser | Lys | Glu | Ile | Trp | Ile | Lys |
| 145 | | | | | 150 | | | | | 155 | | | | | 160 |
| Ala | Leu | Phe | Leu | Leu | Val | Gly | Phe | Trp | Tyr | Cys | Leu | Tyr | Lys | Met | Tyr |
| | | | | 165 | | | | | 170 | | | | | 175 | |
| Thr | Thr | Ser | Asp | Ile | Asp | Gln | Tyr | Gly | Ile | Ala | Ile | Ala | Tyr | Ser | Ile |
| | | | 180 | | | | | 185 | | | | | 190 | | |
| Gly | Met | Gly | Thr | Phe | Ala | Ala | Phe | Ile | Gly | Thr | Cys | Ile | Gln | His | Asp |
| | | 195 | | | | | 200 | | | | | 205 | | | |
| Gly | Asn | His | Gly | Ala | Phe | Ala | Gln | Asn | Lys | Leu | Leu | Asn | Lys | Leu | Ala |
| | 210 | | | | | 215 | | | | | 220 | | | | |
| Gly | Trp | Thr | Leu | Asp | Met | Ile | Gly | Ala | Ser | Ala | Phe | Thr | Trp | Glu | Leu |
| 225 | | | | | 230 | | | | | 235 | | | | | 240 |
| Gln | His | Met | Leu | Gly | His | His | Pro | Tyr | Thr | Asn | Val | Leu | Asp | Gly | Val |
| | | | 245 | | | | | 250 | | | | | 255 | | |
| Glu | Glu | Glu | Arg | Lys | Glu | Arg | Gly | Asp | Val | Ala | Leu | Glu | Glu | Lys | |
| | | | 260 | | | | | 265 | | | | | 270 | | |
| Asp | Gln | Glu | Ser | Asp | Pro | Asp | Val | Phe | Ser | Ser | Phe | Pro | Leu | Met | Arg |
| | | | 275 | | | | | 280 | | | | | 285 | | |
| Met | His | Pro | His | His | Thr | Thr | Ser | Trp | Tyr | His | Lys | Tyr | Gln | His | Leu |
| | | | 290 | | | | | 295 | | | | | 300 | | |
| Tyr | Ala | Pro | Pro | Leu | Phe | Ala | Leu | Met | Thr | Leu | Ala | Lys | Val | Phe | Gln |
| 305 | | | | | 310 | | | | | 315 | | | | | 320 |
| Gln | Asp | Phe | Glu | Val | Ala | Thr | Ser | Gly | Arg | Leu | Tyr | His | Ile | Asp | Ala |
| | | | | 325 | | | | | 330 | | | | | 335 | |
| Asn | Val | Arg | Tyr | Gly | Ser | Val | Trp | Asn | Val | Met | Arg | Phe | Trp | Ala | Met |
| | | | 340 | | | | | 345 | | | | | 350 | | |
| Lys | Val | Ile | Thr | Met | Gly | Tyr | Met | Met | Gly | Leu | Pro | Ile | Tyr | Phe | His |
| | | | | 355 | | | | | 360 | | | | | 365 | |

```
Gly Val Leu Arg Gly Val Gly Leu Phe Val Ile Gly His Leu Ala Cys
    370                 375                 380
Gly Glu Leu Leu Ala Thr Met Phe Ile Val Asn His Val Ile Glu Gly
385                 390                 395                 400
Val Ser Tyr Gly Thr Lys Asp Leu Val Gly Gly Ala Ser His Gly Asp
            405                 410                 415
Glu Lys Lys Ile Val Lys Pro Thr Thr Val Leu Gly Asp Thr Pro Met
        420                 425                 430
Glu Lys Thr Arg Glu Glu Ala Leu Lys Ser Asn Ser Asn Asn Asn Lys
            435                 440                 445
Lys Lys Gly Glu Lys Asn Ser Val Pro Ser Val Pro Phe Asn Asp Trp
    450                 455                 460
Ala Ala Val Gln Cys Gln Thr Ser Val Asn Trp Ser Pro Gly Ser Trp
465                 470                 475                 480
Phe Trp Asn His Phe Ser Gly Gly Leu Ser His Gln Ile Glu His His
            485                 490                 495
Leu Phe Pro Ser Ile Cys His Thr Asn Tyr Cys His Ile Gln Asp Val
        500                 505                 510
Val Glu Ser Thr Cys Ala Glu Tyr Gly Val Pro Tyr Gln Ser Glu Ser
            515                 520                 525
Asn Leu Phe Val Ala Tyr Gly Lys Met Ile Ser His Leu Lys Phe Leu
    530                 535                 540
Gly Lys Ala Lys Cys Glu
545                 550
```

<210> SEQ ID NO 13
<211> LENGTH: 1653
<212> TYPE: DNA
<213> ORGANISM: Thalassiosira pseudonana

<400> SEQUENCE: 13

```
atgggcaacg gcaacctccc agcatccacc gcacagctca agtccacctc gaagccccag      60
cagcaacatg agcatcgcac catctccaag tccgagctcg cccaacacaa cacgcccaaa     120
tcagcatggt gtgccgtcca ctccactccc gccaccgacc catcccactc caacaacaaa     180
caacacgcac acctagtcct cgacattacc gactttgcgt cccgccatcc aggggagac      240
ctcatcctcc tcgcttccgg caagacgcc tcggtgctgt ttgaaacata ccatccacgt      300
ggagttccga cgtctctcat tcaaaagctg cagattggag tgatggagga ggaggcgttt     360
cgggattcgt tttacagttg gactgattct gacttttata ctgtgttgaa gaggaggggtt    420
gtggagcggt tggaggagag ggggttggac aggagggat cgaaagagat ttggatcaag      480
gctttgttct tgttggttgg atttggtac tgtttgtaca agatgtatac tacgtcggat     540
attgatcagt acggtattgc cattgcctat tctattggaa tgggaacctt tgcggcattc     600
atcggcacgt gtattcaaca cgatggaaat cacggtgcat cgctcagaa caagttactc      660
aacaagttgg ctgggtggac gttggatatg attggtgcga gtgcgtttac gtgggagctt     720
cagcacatgc tggggcatca tccatatacg aatgtgttgg atggggtgga ggaggagagg     780
aaggagaggg gggaggatgt tgctttggaa gaaaaggatc aggaatcaga tccagacgta     840
ttctcctcct tccctctcat gagaatgcat ccccaccata caacctcatg gtatcataaa     900
taccaacacc tctacgctcc acccctcttt gcattgatga cacttgccaa agtattccaa     960
caggattttg aagttgccac atccggacga ttatatcata ttgatgccaa tgtacgttat    1020
```

-continued

```
ggttcggtat ggaatgtcat gaggttttgg gctatgaagg tcattacgat gggatatatg    1080
atgggattac caatctactt tcatggagta ctgaggggag ttggattgtt tgttattggg    1140
catttggcgt gtggagagtt gttggcgacg atgtttattg tgaatcacgt cattgagggt    1200
gtgagttatg aacgaagga tttggttggt ggtgcgagtc atggagatga aagaagatt     1260 gtcaagccaa cgactgtatt gggagataca ccaatggaaa agactcgcga ggaggcattg    1320
aaaagcaaca gcaataacaa caagaagaag gagagaaga actcggtacc atccgttcca    1380
ttcaacgact gggcagcagt ccaatgccag acctccgtga attggtctcc aggctcatgg    1440
ttctggaatc acttttctgg gggactctct catcagattg agcatcactt gttccccagc    1500
atttgtcata caaactactg tcatatccag gatgttgtgg agagtacgtg tgctgagtac    1560
ggagttccgt atcagagtga gagtaatttg tttgttgctt atggaaagat gattagtcat    1620
ttgaagtttt tgggtaaagc caagtgtgag tag                                 1653
```

<210> SEQ ID NO 14
<211> LENGTH: 425
<212> TYPE: PRT
<213> ORGANISM: Thalassiosira pseudonana

<400> SEQUENCE: 14

```
Met Gly Gly Ala Gly Ala Ser Glu Ala Glu Arg Pro Lys Trp Thr Thr
 1               5                  10                  15

Ile His Gly Arg His Val Asp Val Ser Lys Phe Arg His Pro Gly Gly
            20                  25                  30

Asn Ile Ile Glu Leu Phe Tyr Gly Met Asp Ser Thr Ser Ala Phe Glu
        35                  40                  45

Gln Phe His Gly His His Lys Gly Ala Trp Lys Met Leu Lys Ala Leu
    50                  55                  60

Pro Thr Lys Glu Val Asp Pro Ala Asp Val Pro Gln Gln Pro Gln Glu
65                  70                  75                  80

His Val Ala Glu Met Thr Arg Leu Met Thr Ser Trp Arg Glu Arg Gly
                85                  90                  95

Leu Phe Lys Pro Arg Pro Val Ala Ser Gly Ile Tyr Gly Leu Ala Val
            100                 105                 110

Val Ala Ala Ile Val Ala Cys Ile Ala Cys Ala Pro His Ala Pro Val
        115                 120                 125

Leu Ser Gly Ile Gly Leu Gly Ser Cys Trp Ala Gln Cys Gly Phe Leu
    130                 135                 140

Gln His Met Gly Gly His Arg Glu Trp Gly Val Arg Tyr Ser Phe Leu
145                 150                 155                 160

Leu Gln His Phe Phe Glu Gly Leu Leu Lys Gly Gly Ser Ala Ser Trp
                165                 170                 175

Trp Arg Asn Arg His Asn Lys His His Ala Lys Thr Asn Val Leu Gly
            180                 185                 190

Glu Asp Gly Asp Leu Arg Thr Thr Pro Phe Phe Ala Trp Asp Pro Thr
        195                 200                 205

Leu Ala Lys Lys Val Pro Asp Trp Ser Leu Lys Thr Gln Ala Phe Thr
    210                 215                 220

Phe Leu Pro Ala Leu Gly Ala Tyr Val Phe Val Phe Ala Phe Thr Ile
225                 230                 235                 240

Arg Lys Tyr Ala Val Val Lys Lys Leu Trp His Glu Leu Ala Leu Met
                245                 250                 255

Ile Ala His Tyr Ala Met Phe Tyr Tyr Ala Leu Gln Leu Ala Gly Ala
```

```
             260                 265                 270
Ser Leu Gly Ser Gly Leu Ala Phe Tyr Cys Thr Gly Tyr Ala Trp Gln
            275                 280                 285

Gly Ile Tyr Leu Gly Phe Phe Phe Gly Leu Ser His Phe Ala Val Glu
            290                 295                 300

Arg Val Pro Ser Thr Ala Thr Trp Leu Glu Ser Ser Met Ile Gly Thr
305                 310                 315                 320

Val Asp Trp Gly Gly Ser Ser Ala Phe Cys Gly Tyr Val Ser Gly Phe
                    325                 330                 335

Leu Asn Ile Gln Ile Glu His His Met Ala Pro Gln Met Pro Met Glu
            340                 345                 350

Asn Leu Arg Gln Ile Arg Ala Asp Cys Lys Ala Ser Ala Glu Lys Leu
            355                 360                 365

Gly Leu Pro Tyr Arg Glu Leu Ser Phe Ala Gly Ala Val Lys Leu Met
            370                 375                 380

Met Val Gly Leu Trp Arg Thr Gly Arg Asp Glu Leu Gln Leu Arg Ser
385                 390                 395                 400

Asp Arg Arg Lys Tyr Ser Arg Thr Gln Ala Tyr Met Ala Ala Ala Ser
                    405                 410                 415

Ala Val Val Glu Asn Leu Lys Ala Asp
            420                 425

<210> SEQ ID NO 15
<211> LENGTH: 1377
<212> TYPE: DNA
<213> ORGANISM: Ostreococcus RCC809

<400> SEQUENCE: 15
```

| | | | | | |
|---|---|---|---|---|---|
| atgccgacga | ctcgatcgcg | cgcgcgcgtg | acgacgcccc | ctcgcgagac | gccgacgaga | 60 |
| gcgaacaccg | tcgccgcgct | cgatcccgag | cgcaagtaca | cgcgcattcg | cggcgtcgtg | 120 |
| tacgacgtca | cggatttcgc | cagccgtcat | ccgggtggcg | cgcaattgtt | atcgctgtgc | 180 |
| gtggggagag | acgccaccat | cctggtggag | agtcatcacc | ttcgtccgga | ggtggtgcaa | 240 |
| aagtacctga | agacgcttcc | cgtggtggag | ggcgcggcgg | gggcgttcgg | gcccgaggag | 300 |
| acgtttccga | aaccgctcga | ctcggatttg | taccgaaaga | ttcaggggcg | cgttcgtaaa | 360 |
| gagatcgtcg | aaccgttgaa | gatgacgcgc | ggacgcgagc | cgcacgggcg | aggctggtgc | 420 |
| gtgttggacg | ccggggtggt | gttggctttc | ttcgcgttcg | cgttgggagt | ctattggaag | 480 |
| acgccgacgg | tggcgacggg | gtgcctgttg | ggctcgccg | gtactggag | cggcaccgga | 540 |
| ttgcaacaca | cggcgaacca | cggtggattg | gcgaagagtg | ggttttggaa | tcagttttgg | 600 |
| ggatggctcg | ggaacgacgt | cgccatcggg | aagagctcgg | tggagtggag | atatcatcac | 660 |
| atggtgagcc | accactcgta | ttgcaacgac | gcggacctcg | atcaagacgt | gtacaccgcg | 720 |
| ctgccgcttc | ttcgtttgga | cccgtcccag | gagttgaagt | ggttccaccg | ctaccaagcg | 780 |
| ttctacgcgc | cgctgatgtg | gccgatgttg | tggctcgccg | cgcagtttgg | cgacgcgcaa | 840 |
| aatatttag | tggataaggc | gtctccgggc | gtcgagtaca | agggcctcat | gaagctcgaa | 900 |
| gtcgcgctgt | acgttctcgg | aaagttttg | cattttagct | tgttgctcgg | cgtaccggcc | 960 |
| tacttgcacg | ggtttgcgaa | cgccatcgtg | ccgttcatcg | cgtacggtgc | gttcggttcg | 1020 |
| ttcgtcctgt | gctggttttt | catcgtcagt | cacaacttgg | aggcgttgac | cccaatcaat | 1080 |
| ctgagcaaat | ccacgaagaa | tgactggggc | gcgtggcaaa | tcgaaacttc | gcgtcctgg | 1140 |
| ggcaacggct | tctggagctt | tttctccggc | gggttgaatt | tgcaaatcga | gcaccacttg | 1200 |

```
ttcccgggtt gcgcgcacaa cttgtacccg aagatggttc ccatcatcaa ggaagagtgc    1260
gaaaaggctg gcgtcacgta caccggttac ggtgggtact ttggtctcct tcccatcact    1320
cgggacatgt tcgcgtactt gtacaaaatg ggccgacaaa gcaaaaagtc ggcgtaa       1377
```

<210> SEQ ID NO 16
<211> LENGTH: 458
<212> TYPE: PRT
<213> ORGANISM: Ostreococcus RCC809

<400> SEQUENCE: 16

```
Met Pro Thr Thr Arg Ser Arg Ala Arg Val Thr Thr Pro Pro Arg Glu
1               5                   10                  15

Thr Pro Thr Arg Ala Asn Thr Val Ala Ala Leu Asp Pro Glu Arg Lys
            20                  25                  30

Tyr Thr Arg Ile Arg Gly Val Val Tyr Asp Val Thr Asp Phe Ala Ser
        35                  40                  45

Arg His Pro Gly Gly Ala Gln Leu Leu Ser Leu Cys Val Gly Arg Asp
    50                  55                  60

Ala Thr Ile Leu Val Glu Ser His His Leu Arg Pro Glu Val Val Gln
65                  70                  75                  80

Lys Tyr Leu Lys Thr Leu Pro Val Val Glu Gly Ala Ala Gly Ala Phe
                85                  90                  95

Gly Pro Glu Glu Thr Phe Pro Lys Pro Leu Asp Ser Asp Leu Tyr Arg
            100                 105                 110

Lys Ile Gln Gly Arg Val Arg Lys Glu Ile Val Glu Pro Leu Lys Met
        115                 120                 125

Thr Arg Gly Arg Glu Pro His Gly Arg Gly Trp Cys Val Leu Asp Ala
    130                 135                 140

Gly Val Val Leu Ala Phe Phe Ala Phe Ala Leu Gly Val Tyr Trp Lys
145                 150                 155                 160

Thr Pro Thr Val Ala Thr Gly Cys Leu Leu Gly Leu Ala Gly Tyr Trp
                165                 170                 175

Ser Gly Thr Gly Leu Gln His Thr Ala Asn His Gly Gly Leu Ala Lys
            180                 185                 190

Ser Gly Phe Trp Asn Gln Phe Trp Gly Trp Leu Gly Asn Asp Val Ala
        195                 200                 205

Ile Gly Lys Ser Ser Val Glu Trp Arg Tyr His His Met Val Ser His
    210                 215                 220

His Ser Tyr Cys Asn Asp Ala Asp Leu Asp Gln Asp Val Tyr Thr Ala
225                 230                 235                 240

Leu Pro Leu Leu Arg Leu Asp Pro Ser Gln Glu Leu Lys Trp Phe His
                245                 250                 255

Arg Tyr Gln Ala Phe Tyr Ala Pro Leu Met Trp Pro Met Leu Trp Leu
            260                 265                 270

Ala Ala Gln Phe Gly Asp Ala Gln Asn Ile Leu Val Asp Lys Ala Ser
        275                 280                 285

Pro Gly Val Glu Tyr Lys Gly Leu Met Lys Leu Glu Val Ala Leu Tyr
    290                 295                 300

Val Leu Gly Lys Phe Leu His Phe Ser Leu Leu Gly Val Pro Ala
305                 310                 315                 320

Tyr Leu His Gly Phe Ala Asn Ala Ile Val Pro Phe Ile Ala Tyr Gly
                325                 330                 335

Ala Phe Gly Ser Phe Val Leu Cys Trp Phe Phe Ile Val Ser His Asn
```

```
                   340                 345                 350
Leu Glu Ala Leu Thr Pro Ile Asn Leu Ser Lys Ser Thr Lys Asn Asp
            355                 360                 365

Trp Gly Ala Trp Gln Ile Glu Thr Ser Ala Ser Trp Gly Asn Gly Phe
        370                 375                 380

Trp Ser Phe Phe Ser Gly Gly Leu Asn Leu Gln Ile Glu His His Leu
385                 390                 395                 400

Phe Pro Gly Cys Ala His Asn Leu Tyr Pro Lys Met Val Pro Ile Ile
                405                 410                 415

Lys Glu Glu Cys Glu Lys Ala Gly Val Thr Tyr Thr Gly Tyr Gly Gly
            420                 425                 430

Tyr Phe Gly Leu Leu Pro Ile Thr Arg Asp Met Phe Ala Tyr Leu Tyr
        435                 440                 445

Lys Met Gly Arg Gln Ser Lys Lys Ser Ala
    450                 455

<210> SEQ ID NO 17
<211> LENGTH: 1430
<212> TYPE: DNA
<213> ORGANISM: Ostreococcus RCC809

<400> SEQUENCE: 17
ggatccggta ccaagcttga tatcaccaaa atgccaacta ctcgttctcg tgctcgtgtt      60
actactccac ctcgtgaaac tcctactcgt gctaatactg ttgctgcttt agatccagaa     120 cgtaaaatata cacgtattcg aggtgttgta tatgatgtta ctgattttgc tagtcgacat     180
ccaggtggtg cacaattatt atctttatgt gttggtcgtg atgctacaat tttagtagaa     240
tcacatcatt tacgaccaga agttgtacaa aaatatttaa aaacattacc tgttgtagaa     300
ggtgctgctg gtgcatttgg tccagaagaa acttttccaa acctttaga tagtgattta     360 tatcgtaaaa ttcaaggtcg tgttcgaaaa gaaattgtag aaccattaaa aatgacacgt     420
ggtcgagaac ctcatggtcg tggttggtgt gttttagatg ctggtgttgt attagctttc     480
tttgcttttg cattaggtgt ttattggaaa acaccaactg tagctactgg ttgtttatta     540
ggtttagcag gttattggtc tggtacaggt ttacaacata ctgctaatca tggtggttta     600
gcaaaatcag gttttggaat caattttggg gttggttagg aaatgatgtt gctattggta     660
aatcaagtgt agaatggcgt tatcatcata tggtttcaca tcatagttat tgtaatgatg     720
ctgatttaga tcaagatgtt tatacagcat taccattatt acgtttagat ccttcacaag     780
aattaaaatg gtttcatcgt tatcaagcat tttatgcacc tttaatgtgg cctatgttat     840
ggttagctgc acaatttggt gatgctcaaa atattttagt tgataaagca agtccaggtg     900
tagaatataa aggtttaatg aaattagaag ttgcttata tgtattagga aaattttttac     960 attttttcttt attattaggt gttcctgcat atttacatgg ttttgctaat gcaattgtac    1020
catttattgc ttatggtgca tttggttcat tgtttttatg ttggttttc attgtaagtc    1080 ataaatttaga agcattaaca ccaattaatt tatctaaatc aactaaaaat gattggggtg    1140
cttggcaaat tgaaactagt gcatcttggg gtaatggttt ttggtcattt ttctcaggtg    1200
gtttaaattt acaaattgaa catcattat ttcctggttg tgctcataat ttatatccaa    1260
aaatggttcc tattattaaa gaagaatgtg aaaaagcagg tgttacatat actggttatg    1320
gtggttattt tggtttatta ccaattactc gtgatatgtt tgcttattta tataaaatgg    1380
gtcgtcaatc taaaaaatct gcttaagagc tcggtaccct cgagtctaga                1430
```

<210> SEQ ID NO 18
<211> LENGTH: 458
<212> TYPE: PRT
<213> ORGANISM: Ostreococcus RCC809

<400> SEQUENCE: 18

```
Met Pro Thr Thr Arg Ser Arg Ala Arg Val Thr Thr Pro Pro Arg Glu
1               5                   10                  15

Thr Pro Thr Arg Ala Asn Thr Val Ala Ala Leu Asp Pro Glu Arg Lys
            20                  25                  30

Tyr Thr Arg Ile Arg Gly Val Val Tyr Asp Val Thr Asp Phe Ala Ser
        35                  40                  45

Arg His Pro Gly Gly Ala Gln Leu Leu Ser Leu Cys Val Gly Arg Asp
    50                  55                  60

Ala Thr Ile Leu Val Glu Ser His His Leu Arg Pro Glu Val Val Gln
65                  70                  75                  80

Lys Tyr Leu Lys Thr Leu Pro Val Val Glu Gly Ala Ala Gly Ala Phe
                85                  90                  95

Gly Pro Glu Glu Thr Phe Pro Lys Pro Leu Asp Ser Asp Leu Tyr Arg
            100                 105                 110

Lys Ile Gln Gly Arg Val Arg Lys Glu Ile Val Glu Pro Leu Lys Met
        115                 120                 125

Thr Arg Gly Arg Glu Pro His Gly Arg Gly Trp Cys Val Leu Asp Ala
    130                 135                 140

Gly Val Val Leu Ala Phe Phe Ala Phe Ala Leu Gly Val Tyr Trp Lys
145                 150                 155                 160

Thr Pro Thr Val Ala Thr Gly Cys Leu Leu Gly Leu Ala Gly Tyr Trp
                165                 170                 175

Ser Gly Thr Gly Leu Gln His Thr Ala Asn His Gly Gly Leu Ala Lys
            180                 185                 190

Ser Gly Phe Trp Asn Gln Phe Trp Gly Trp Leu Gly Asn Asp Val Ala
        195                 200                 205

Ile Gly Lys Ser Ser Val Glu Trp Arg Tyr His His Met Val Ser His
    210                 215                 220

His Ser Tyr Cys Asn Asp Ala Asp Leu Asp Gln Asp Val Tyr Thr Ala
225                 230                 235                 240

Leu Pro Leu Leu Arg Leu Asp Pro Ser Gln Glu Leu Lys Trp Phe His
                245                 250                 255

Arg Tyr Gln Ala Phe Tyr Ala Pro Leu Met Trp Pro Met Leu Trp Leu
            260                 265                 270

Ala Ala Gln Phe Gly Asp Ala Gln Asn Ile Leu Val Asp Lys Ala Ser
        275                 280                 285

Pro Gly Val Glu Tyr Lys Gly Leu Met Lys Leu Glu Val Ala Leu Tyr
    290                 295                 300

Val Leu Gly Lys Phe Leu His Phe Ser Leu Leu Leu Gly Val Pro Ala
305                 310                 315                 320

Tyr Leu His Gly Phe Ala Asn Ala Ile Val Pro Phe Ile Ala Tyr Gly
                325                 330                 335

Ala Phe Gly Ser Phe Val Leu Cys Trp Phe Ile Val Ser His Asn
            340                 345                 350

Leu Glu Ala Leu Thr Pro Ile Asn Leu Ser Lys Ser Thr Lys Asn Asp
        355                 360                 365

Trp Gly Ala Trp Gln Ile Glu Thr Ser Ala Ser Trp Gly Asn Gly Phe
    370                 375                 380
```

Trp Ser Phe Phe Ser Gly Gly Leu Asn Leu Gln Ile Glu His His Leu
385                 390                 395                 400

Phe Pro Gly Cys Ala His Asn Leu Tyr Pro Lys Met Val Pro Ile Ile
            405                 410                 415

Lys Glu Glu Cys Glu Lys Ala Gly Val Thr Tyr Thr Tyr Gly Gly
            420                 425                 430

Tyr Phe Gly Leu Leu Pro Ile Thr Arg Asp Met Phe Ala Tyr Leu Tyr
        435                 440                 445

Lys Met Gly Arg Gln Ser Lys Lys Ser Ala
        450                 455

<210> SEQ ID NO 19
<211> LENGTH: 863
<212> TYPE: DNA
<213> ORGANISM: Fragilariopsis cylindrus

<400> SEQUENCE: 19

```
ccatggggta ccgatatcac caaaatggac gagtacaaag caactcttga atctgttggg      60
gatgctatca tccaatgggc agatcctgaa agtcagttca ccgggttcac caagggatgg     120
ttcttgacag atttcacatc tgcgtttagt attgcacttg tatacgtctt atttgtcatc     180
attggttctc aagtgatgaa agtcttacct gctattgatc cgtacccaat caagtttttt     240
tacaatgtat cacaaattat gctgtgtgct tacatgacga ttgaagcatg tctgttagcg     300
taccgtaacg gatacactat catgccatgt gtcggataca atagagatga tccagcaatt     360
ggaaatcttt tatggttatt ttatgtttca aaagtttggg attttgggga taccatcttt     420
atcgttttgg ggaagaagtg gagacaactt tctttccttc acgttaccat catacccacc     480
atctttttgt tctactggct taacgcgaat gtcttttatg atggtgatat ttatcttacc     540
attgctctga atggtttcat ccatactgtt atgtacacat actactttat ctgtatgcat     600
actaaagaca agaaaactgg aaaatcgctt cctatctggt ggaaatcatc tttgactttg     660
ttgcaattgt ttcagttcat taccatgatg tcacagggct tataccttat cattttttggt    720
tgtgaatcac tttctatccg agtcactgcg acatacgttg tttacatatt gtcactttc     780
ttttttgtttg cgcaattctt cgttgcatct tacatgcaac ctaagaaatc gaagactgcc     840
taagagctcg gtaccttaat taa                                              863
```

<210> SEQ ID NO 20
<211> LENGTH: 272
<212> TYPE: PRT
<213> ORGANISM: Fragilariopsis cylindrus

<400> SEQUENCE: 20

Met Asp Glu Tyr Lys Ala Thr Leu Glu Ser Val Gly Asp Ala Ile Ile
1               5                   10                  15

Gln Trp Ala Asp Pro Glu Ser Gln Phe Thr Gly Phe Thr Lys Gly Trp
            20                  25                  30

Phe Leu Thr Asp Phe Thr Ser Ala Phe Ser Ile Ala Leu Val Tyr Val
        35                  40                  45

Leu Phe Val Ile Ile Gly Ser Gln Val Met Lys Val Leu Pro Ala Ile
        50                  55                  60

Asp Pro Tyr Pro Ile Lys Phe Phe Tyr Asn Val Ser Gln Ile Met Leu
65                  70                  75                  80

Cys Ala Tyr Met Thr Ile Glu Ala Cys Leu Leu Ala Tyr Arg Asn Gly
            85                  90                  95

```
Tyr Thr Ile Met Pro Cys Val Gly Tyr Asn Arg Asp Asp Pro Ala Ile
            100                 105                 110

Gly Asn Leu Leu Trp Leu Phe Tyr Val Ser Lys Val Trp Asp Phe Trp
            115                 120                 125

Asp Thr Ile Phe Ile Val Leu Gly Lys Lys Trp Arg Gln Leu Ser Phe
        130                 135                 140

Leu His Val Tyr His His Thr Thr Ile Phe Leu Phe Tyr Trp Leu Asn
145                 150                 155                 160

Ala Asn Val Phe Tyr Asp Gly Asp Ile Tyr Leu Thr Ile Ala Leu Asn
                165                 170                 175

Gly Phe Ile His Thr Val Met Tyr Thr Tyr Tyr Phe Ile Cys Met His
            180                 185                 190

Thr Lys Asp Lys Lys Thr Gly Lys Ser Leu Pro Ile Trp Trp Lys Ser
            195                 200                 205

Ser Leu Thr Leu Leu Gln Leu Phe Gln Phe Ile Thr Met Met Ser Gln
        210                 215                 220

Gly Leu Tyr Leu Ile Ile Phe Gly Cys Glu Ser Leu Ser Ile Arg Val
225                 230                 235                 240

Thr Ala Thr Tyr Val Val Tyr Ile Leu Ser Leu Phe Phe Leu Phe Ala
                245                 250                 255

Gln Phe Phe Val Ala Ser Tyr Met Gln Pro Lys Lys Ser Lys Thr Ala
            260                 265                 270

<210> SEQ ID NO 21
<211> LENGTH: 1323
<212> TYPE: DNA
<213> ORGANISM: Fragilariopsis cylindrus

<400> SEQUENCE: 21
atggcacccg acgccgatca caagctgaga cagcgccgtc taaaaggcga cgaagtttgt      60
atcgatggaa ttatctatga tatatcatcc ttcgagcatc cgggtggtga tactatcaac     120
gtatttggtg gaaacgatgc aacaattcag tacaaaatga ttcacccgta ccataccacg     180
aagcatttag aaaaaatgaa ggtagttggt aaagttccag actactactc agaatacaaa     240
tgggatacac ccttcgaacg tgaaatgaaa cgtgaggtat ttaaaattgt acgacgtgga     300
caagaatttg gtacaaatgg atattttttc cgtgccattt cgtatattgc tatgtttttt     360
tatctgcaat atttatggat gcaagaatct tcctacacgt tagccatcgt atacgggatt     420
agtatgggat tgattggact gaatgtccag catgatgcga accacggagc tgcatcgaaa     480
aaagtgtggg tgaatgacct cctaggattg ggagcagact ttatcggagg atcgaaatgg     540
ttgtggatgg aaaaacattg gacgcatcat gctttacaa accatcgaga aaaggatcca     600
gatgggttag cagcggaacc tttcctattg ttcaacgact acgacttgtc gagttccaaa     660
cgtgctggat tcatgcata ccaaggaatt tatttagtcc tattattgtg tgggtattgg     720
ctttcggcaa ttattgatat acctgtaatt tggaatctac aagatcgtgg tgcccttacg     780
gtaggaatcc agctggataa cgattggatt gctagtcgaa gaaagtacgc ggttagtctt     840
cgaatcttat acctcttttg taacatcgtc gttcctctct ataacaattt ctcctggaca     900
accgtgagtc atatcaatgt aatgggaatt tgtggtagcc ttacattagg actacttttt     960
accttgtcgc acaattttga gaatgtagat cgagatccta ccaatctgaa cttaaatgaa    1020
acagaagaac ctgtttgctg gttcaaatct caagtagaaa cttcttcaac atacgggggc    1080
atgatatccg gatggttaac cggcggatta aactttcagg ttgagcacca tttattcccg    1140
```

```
agaatgtcta gtgcttggta tccatttatt gcaccaaaag ttcgtgaaat ttgcaaaaag    1200
cacggagttc gttacgtata ctatccatgg ttgttgcaaa atatgtattc gacgttgaag    1260
tacacccacg aggttggtgt cggctcacat tggaaggata atccttttaa gggtgaaatg    1320
tag                                                                 1323

<210> SEQ ID NO 22
<211> LENGTH: 440
<212> TYPE: PRT
<213> ORGANISM: Fragilariopsis cylindrus

<400> SEQUENCE: 22

Met Ala Pro Asp Ala Asp His Lys Leu Arg Gln Arg Leu Lys Gly
1               5                   10                  15

Asp Glu Val Cys Ile Asp Gly Ile Ile Tyr Asp Ile Ser Ser Phe Glu
            20                  25                  30

His Pro Gly Gly Asp Thr Ile Asn Val Phe Gly Gly Asn Asp Ala Thr
        35                  40                  45

Ile Gln Tyr Lys Met Ile His Pro Tyr His Thr Thr Lys His Leu Glu
    50                  55                  60

Lys Met Lys Val Val Gly Lys Val Pro Asp Tyr Tyr Ser Glu Tyr Lys
65                  70                  75                  80

Trp Asp Thr Pro Phe Glu Arg Glu Met Lys Arg Glu Val Phe Lys Ile
                85                  90                  95

Val Arg Arg Gly Gln Glu Phe Gly Thr Asn Gly Tyr Phe Phe Arg Ala
            100                 105                 110

Ile Ser Tyr Ile Ala Met Phe Phe Tyr Leu Gln Tyr Leu Trp Met Gln
        115                 120                 125

Glu Ser Ser Tyr Thr Leu Ala Ile Val Tyr Gly Ile Ser Met Gly Leu
    130                 135                 140

Ile Gly Leu Asn Val Gln His Asp Ala Asn His Gly Ala Ala Ser Lys
145                 150                 155                 160

Lys Val Trp Val Asn Asp Leu Leu Gly Leu Gly Ala Asp Phe Ile Gly
                165                 170                 175

Gly Ser Lys Trp Leu Trp Met Glu Lys His Trp Thr His His Ala Phe
            180                 185                 190

Thr Asn His Arg Glu Lys Asp Pro Asp Gly Leu Ala Ala Glu Pro Phe
        195                 200                 205

Leu Leu Phe Asn Asp Tyr Asp Leu Ser Ser Lys Arg Ala Gly Tyr
    210                 215                 220

His Ala Tyr Gln Gly Ile Tyr Leu Val Leu Leu Cys Gly Tyr Trp
225                 230                 235                 240

Leu Ser Ala Ile Ile Asp Ile Pro Val Ile Trp Asn Leu Gln Asp Arg
                245                 250                 255

Gly Ala Leu Thr Val Gly Ile Gln Leu Asp Asn Asp Trp Ile Ala Ser
            260                 265                 270

Arg Arg Lys Tyr Ala Val Ser Leu Arg Ile Leu Tyr Leu Phe Cys Asn
        275                 280                 285

Ile Val Val Pro Leu Tyr Asn Asn Phe Ser Trp Thr Thr Val Ser His
    290                 295                 300

Ile Asn Val Met Gly Ile Cys Gly Ser Leu Thr Leu Gly Leu Leu Phe
305                 310                 315                 320

Thr Leu Ser His Asn Phe Glu Asn Val Asp Arg Asp Pro Thr Asn Leu
                325                 330                 335
```

```
Asn Leu Asn Glu Thr Glu Pro Val Cys Trp Phe Lys Ser Gln Val
            340                 345                 350
Glu Thr Ser Ser Thr Tyr Gly Gly Met Ile Ser Gly Trp Leu Thr Gly
355                 360                 365
Gly Leu Asn Phe Gln Val Glu His His Leu Phe Pro Arg Met Ser Ser
    370                 375                 380
Ala Trp Tyr Pro Phe Ile Ala Pro Lys Val Arg Glu Ile Cys Lys Lys
385                 390                 395                 400
His Gly Val Arg Tyr Val Tyr Tyr Pro Trp Leu Leu Gln Asn Met Tyr
                405                 410                 415
Ser Thr Leu Lys Tyr Thr His Glu Val Gly Val Gly Ser His Trp Lys
            420                 425                 430
Asp Asn Pro Phe Lys Gly Glu Met
            435                 440

<210> SEQ ID NO 23
<211> LENGTH: 1584
<212> TYPE: DNA
<213> ORGANISM: Phaeodactylum tricornutum

<400> SEQUENCE: 23
```

| | | | | | |
|---|---|---|---|---|---|
| atggcagggg | ggggtgtcgt | tacggcgggg | gagatcaagc | actacccccgg | ccgaacaacc | 60 |
| ttctttgtga | ttatggtctg | tatagtggcg | gcatccggag | gtctcatgtt | cggatacgat | 120 |
| gtcggaattt | caggggggtgt | cacgtctatg | gacgaatttt | tggcgaaatt | ttttcctgcg | 180 |
| gtgttggcga | agaagcgagc | agaggcagct | tcggagagcg | cctactgcaa | gtatgatgac | 240 |
| cagaagctgc | aagccttcac | atcgtcgctg | tacatttccg | cactcgtgtc | gacattcttc | 300 |
| tcgtcgtaca | ccaccaggca | ctacggccgt | aaatttacca | tgctcatagc | tggtttcgcc | 360 |
| ttctgcttcg | gcgtcatctt | caccgccgct | gcgcaagaaa | tcatcatgct | aatcataggg | 420 |
| cgcgtcctcc | tgggttgggg | tgtcggattc | gctaaccagg | ctgttccgtt | gtacctctcc | 480 |
| gaaatggcac | cctccaagtg | gcgaggtgcg | ctcaacatcc | tcttccaatt | ggcggtgacc | 540 |
| attggcatcc | tgttcgccag | tctcgtgaac | tacggcacag | agaagatggc | tcgcaacggg | 600 |
| tggcgtgttt | ccctcgccat | cgccggcctg | cctgcgatct | tcatcaccct | cggaggatta | 660 |
| ctcctgccag | acacaccgaa | ttccctcgtg | caacgcggca | agcacgagag | cgcccgccag | 720 |
| gtcctacgca | ggattcgtgg | cgtcgacaac | attgaggaag | agttcgacga | catcctcatt | 780 |
| gccagtaacg | aagccgcctc | cgtgaagcac | cccttccgca | atatcttgaa | cgccgcaaac | 840 |
| cgccctcagc | tggtcatctc | catggctctt | cagttttttcc | agcaattcac | tggaattaat | 900 |
| gctattatgt | tttacgcgcc | tgtcttgttc | cagacgctgg | gattcgggag | ttccgcttca | 960 |
| ctttactctg | ctgtcatcgt | tggagccgtg | aatgtgctgg | ccacttgcgt | cgctatcgct | 1020 |
| gttgtggatc | gattcggtcg | acgatggttg | ctcttggaag | cttgcatcca | aatgttctta | 1080 |
| gcacagacgg | cgattgcaat | tatcctggcg | gcgggattga | aggggaccga | gatgccggag | 1140 |
| tatctgggat | ggatcgcggt | ggtattgatt | tgcgtgtacg | tgtcttcttt | cgcgtggtct | 1200 |
| tggggtccac | ttggatggtt | gattccaagt | gagattttcc | ccttggagac | gcgttcagca | 1260 |
| gggcaagcca | tcacggtgtc | gaccaacatg | gtcttcacct | tcctcatcgc | gcaagtgttc | 1320 |
| ctgtcaatgt | tgtgcgcgtt | caagtggggc | atcttcctct | tcttcgccgc | gtgggtggtg | 1380 |
| gtgatgttcc | ttttttacgta | cttttttaatt | cccgagacga | agggcatccc | catcgaggag | 1440 |
| atggatctcg | tgtggaccaa | gcactggttc | tggaagcgct | acgtccccta | ccctgagact | 1500 |

```
ctcgctcaca ccagcggcat ccccatggga gatatgaagg tcagcaagct ggagaatggc    1560
tccgcaaatg gccacaaact gtaa                                            1584
```

<210> SEQ ID NO 24
<211> LENGTH: 527
<212> TYPE: PRT
<213> ORGANISM: Phaeodactylum tricornutum

<400> SEQUENCE: 24

```
Met Ala Gly Gly Val Val Thr Ala Gly Glu Ile Lys His Tyr Pro
1               5                   10                  15

Gly Arg Thr Thr Phe Phe Val Ile Met Val Cys Ile Val Ala Ala Ser
                20                  25                  30

Gly Gly Leu Met Phe Gly Tyr Asp Val Gly Ile Ser Gly Val Thr
            35                  40                  45

Ser Met Asp Glu Phe Leu Ala Lys Phe Phe Pro Ala Val Leu Ala Lys
50                  55                  60

Lys Arg Ala Glu Ala Ala Ser Glu Ser Ala Tyr Cys Lys Tyr Asp Asp
65                  70                  75                  80

Gln Lys Leu Gln Ala Phe Thr Ser Ser Leu Tyr Ile Ser Ala Leu Val
                85                  90                  95

Ser Thr Phe Phe Ser Ser Tyr Thr Thr Arg His Tyr Gly Arg Lys Phe
            100                 105                 110

Thr Met Leu Ile Ala Gly Phe Ala Phe Cys Phe Gly Val Ile Phe Thr
        115                 120                 125

Ala Ala Ala Gln Glu Ile Ile Met Leu Ile Ile Gly Arg Val Leu Leu
    130                 135                 140

Gly Trp Gly Val Gly Phe Ala Asn Gln Ala Val Pro Leu Tyr Leu Ser
145                 150                 155                 160

Glu Met Ala Pro Ser Lys Trp Arg Gly Ala Leu Asn Ile Leu Phe Gln
                165                 170                 175

Leu Ala Val Thr Ile Gly Ile Leu Phe Ala Ser Leu Val Asn Tyr Gly
            180                 185                 190

Thr Glu Lys Met Ala Arg Asn Gly Trp Arg Val Ser Leu Ala Ile Ala
        195                 200                 205

Gly Leu Pro Ala Ile Phe Ile Thr Leu Gly Gly Leu Leu Pro Asp
    210                 215                 220

Thr Pro Asn Ser Leu Val Gln Arg Gly Lys His Glu Ser Ala Arg Gln
225                 230                 235                 240

Val Leu Arg Arg Ile Arg Gly Val Asp Asn Ile Glu Glu Glu Phe Asp
                245                 250                 255

Asp Ile Leu Ile Ala Ser Asn Glu Ala Ala Ser Val Lys His Pro Phe
            260                 265                 270

Arg Asn Ile Leu Lys Arg Arg Asn Arg Pro Gln Leu Val Ile Ser Met
        275                 280                 285

Ala Leu Gln Phe Phe Gln Gln Phe Thr Gly Ile Asn Ala Ile Met Phe
    290                 295                 300

Tyr Ala Pro Val Leu Phe Gln Thr Leu Gly Phe Gly Ser Ser Ala Ser
305                 310                 315                 320

Leu Tyr Ser Ala Val Ile Val Gly Ala Val Asn Val Leu Ala Thr Cys
                325                 330                 335

Val Ala Ile Ala Val Val Asp Arg Phe Gly Arg Arg Trp Leu Leu Leu
            340                 345                 350
```

| | | | | | | | | | | | |
|---|---|---|---|---|---|---|---|---|---|---|---|
| Glu | Ala | Cys | Ile | Gln | Met | Phe | Leu | Ala | Gln | Thr | Ala | Ile | Ala | Ile | Ile |

Glu Ala Cys Ile Gln Met Phe Leu Ala Gln Thr Ala Ile Ala Ile Ile
        355                 360                 365

Leu Ala Ala Gly Leu Lys Gly Thr Glu Met Pro Glu Tyr Leu Gly Trp
        370                 375                 380

Ile Ala Val Val Leu Ile Cys Val Tyr Val Ser Ser Phe Ala Trp Ser
385                 390                 395                 400

Trp Gly Pro Leu Gly Trp Leu Ile Pro Ser Glu Ile Phe Pro Leu Glu
                405                 410                 415

Thr Arg Ser Ala Gly Gln Ala Ile Thr Val Ser Thr Asn Met Val Phe
                420                 425                 430

Thr Phe Leu Ile Ala Gln Val Phe Leu Ser Met Leu Cys Ala Phe Lys
        435                 440                 445

Trp Gly Ile Phe Leu Phe Phe Ala Ala Trp Val Val Met Phe Leu
    450                 455                 460

Phe Thr Tyr Phe Leu Ile Pro Glu Thr Lys Gly Ile Pro Ile Glu Glu
465                 470                 475                 480

Met Asp Leu Val Trp Thr Lys His Trp Phe Trp Lys Arg Tyr Val Pro
                485                 490                 495

Tyr Pro Glu Thr Leu Ala His Thr Ser Gly Ile Pro Met Gly Asp Met
                500                 505                 510

Lys Val Ser Lys Leu Glu Asn Gly Ser Ala Asn Gly His Lys Leu
        515                 520                 525

<210> SEQ ID NO 25
<211> LENGTH: 1479
<212> TYPE: DNA
<213> ORGANISM: Homo sapiens

<400> SEQUENCE: 25

```
atggagccca gcagcaagaa gctgacgggt cgcctcatgc tggctgtggg aggagcagtg      60
cttggctccc tgcagtttgg ctacaacact ggagtcatca tgcccccca gaaggtgatc     120
gaggagttct acaaccagac atgggtccac cgctatgggg agagcatcct gcccaccacg     180
ctcaccacgc tctggtccct ctcagtggcc atctttttctg ttgggggcat gattggctcc     240
ttctctgtgg gccttttcgt taaccgcttt ggccggcgga attcaatgct gatgatgaac     300
ctgctggcct tcgtgtccgc cgtgctcatg gcttctcga aactgggcaa gtcctttgag     360
atgctgatcc tgggccgctt catcatcggt gtgtactgcg gcctgaccac aggcttcgtg     420
cccatgtatg tgggtgaagt gtcacccaca gcctttcgtg gggccctggg caccctgcac     480
cagctgggca tcgtcgtcgg catcctcatc gcccaggtgt tcggcctgga ctccatcatg     540
ggcaacaagg acctgtggcc cctgctgctg agcatcatct tcatccccgg cctgctgcag     600
tgcatcgtgc tgcccttctg ccccgagagt cccgcttcc tgctcatcaa cgcaacgag     660
gagaaccggg ccaagagtgt gctaaagaag ctgcgcggga cagctgacgt gacccatgac     720
ctgcaggaga tgaaggaaga gagtcggcag atgatgcggg agaagaaggt caccatcctg     780
gagctgttcc gctcccccgc ctaccgccag cccatcctca tcgctgtggt gctgcagctg     840
tcccagcagc tgtctggcat caacgctgtc ttctattact ccacgagcat cttcgagaag     900
gcgggggtgc agcagcctgt gtatgccacc attggctccg gtatcgtcaa cacggccttc     960
actgtcgtgt cgctgtttgt ggtggagcga gcaggccggc ggaccctgca cctcatagcc    1020
ctcgctggca tggcgggttg tgccatactc atgaccatcg cgctagcact gctggagcag    1080
ctaccctgga tgtcctatct gagcatcgtg gccatctttg gctttgtggc cttcttgaa    1140
```

-continued

```
gtgggtcctg gccccatccc atggttcatc gtggctgaac tcttcagcca gggtccacgt    1200
ccagctgcca ttgccgttgc aggcttctcc aactggacct caaatttcat tgtgggcatg    1260
tgcttccagt atgtggagca actgtgtggt ccctacgtct tcatcatctt cactgtgctc    1320
ctggttctgt tcttcatctt cacctacttc aaagttcctg agactaaagg ccggaccttc    1380
gatgagatcg cttccggctt ccggcagggg ggagccagcc aaagtgataa gacacccgag    1440
gagctgttcc atccctggg ggctgattcc caagtgtga                            1479
```

<210> SEQ ID NO 26
<211> LENGTH: 492
<212> TYPE: PRT
<213> ORGANISM: Homo sapiens

<400> SEQUENCE: 26

```
Met Glu Pro Ser Ser Lys Lys Leu Thr Gly Arg Leu Met Leu Ala Val
  1               5                  10                  15

Gly Gly Ala Val Leu Gly Ser Leu Gln Phe Gly Tyr Asn Thr Gly Val
             20                  25                  30

Ile Asn Ala Pro Gln Lys Val Ile Glu Glu Phe Tyr Asn Gln Thr Trp
         35                  40                  45

Val His Arg Tyr Gly Glu Ser Ile Leu Pro Thr Thr Leu Thr Thr Leu
     50                  55                  60

Trp Ser Leu Ser Val Ala Ile Phe Ser Val Gly Gly Met Ile Gly Ser
 65                  70                  75                  80

Phe Ser Val Gly Leu Phe Val Asn Arg Phe Gly Arg Arg Asn Ser Met
                 85                  90                  95

Leu Met Met Asn Leu Leu Ala Phe Val Ser Ala Val Leu Met Gly Phe
            100                 105                 110

Ser Lys Leu Gly Lys Ser Phe Glu Met Leu Ile Leu Gly Arg Phe Ile
        115                 120                 125

Ile Gly Val Tyr Cys Gly Leu Thr Thr Gly Phe Val Pro Met Tyr Val
    130                 135                 140

Gly Glu Val Ser Pro Thr Ala Phe Arg Gly Ala Leu Gly Thr Leu His
145                 150                 155                 160

Gln Leu Gly Ile Val Gly Ile Leu Ile Ala Gln Val Phe Gly Leu
                165                 170                 175

Asp Ser Ile Met Gly Asn Lys Asp Leu Trp Pro Leu Leu Leu Ser Ile
            180                 185                 190

Ile Phe Ile Pro Ala Leu Leu Gln Cys Ile Val Leu Pro Phe Cys Pro
        195                 200                 205

Glu Ser Pro Arg Phe Leu Leu Ile Asn Arg Asn Glu Glu Asn Arg Ala
    210                 215                 220

Lys Ser Val Leu Lys Lys Leu Arg Gly Thr Ala Asp Val Thr His Asp
225                 230                 235                 240

Leu Gln Glu Met Lys Glu Glu Ser Arg Gln Met Met Arg Glu Lys Lys
                245                 250                 255

Val Thr Ile Leu Glu Leu Phe Arg Ser Pro Ala Tyr Arg Gln Pro Ile
            260                 265                 270

Leu Ile Ala Val Val Leu Gln Leu Ser Gln Gln Leu Ser Gly Ile Asn
        275                 280                 285

Ala Val Phe Tyr Tyr Ser Thr Ser Ile Phe Glu Lys Ala Gly Val Gln
    290                 295                 300

Gln Pro Val Tyr Ala Thr Ile Gly Ser Gly Ile Val Asn Thr Ala Phe
305                 310                 315                 320
```

```
Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
            340                 345                 350

Ile Ala Leu Ala Leu Leu Glu Gln Leu Pro Trp Met Ser Tyr Leu Ser
        355                 360                 365

Ile Val Ala Ile Phe Gly Phe Val Ala Phe Phe Glu Val Gly Pro Gly
    370                 375                 380

Pro Ile Pro Trp Phe Ile Val Ala Glu Leu Phe Ser Gln Gly Pro Arg
385                 390                 395                 400

Pro Ala Ala Ile Ala Val Ala Gly Phe Ser Asn Trp Thr Ser Asn Phe
            405                 410                 415

Ile Val Gly Met Cys Phe Gln Tyr Val Glu Gln Leu Cys Gly Pro Tyr
            420                 425                 430

Val Phe Ile Ile Phe Thr Val Leu Leu Val Leu Phe Phe Ile Phe Thr
        435                 440                 445

Tyr Phe Lys Val Pro Glu Thr Lys Gly Arg Thr Phe Asp Glu Ile Ala
    450                 455                 460

Ser Gly Phe Arg Gln Gly Gly Ala Ser Gln Ser Asp Lys Thr Pro Glu
465                 470                 475                 480

Glu Leu Phe His Pro Leu Gly Ala Asp Ser Gln Val
            485                 490
```